US011833216B2

United States Patent
Hooper et al.

(10) Patent No.: US 11,833,216 B2
(45) Date of Patent: Dec. 5, 2023

(54) ANTI-EDB ANTIBODIES AND ANTIBODY-DRUG CONJUGATES

(71) Applicant: Pfizer Inc., New York, NY (US)

(72) Inventors: Andrea Therese Hooper, Port Chester, NY (US); Kimberly Ann Marquette, Somerville, MA (US); Chakrapani Subramanyam, South Glastonbury, CT (US); Hans-Peter Gerber, San Carlos, CA (US); Chad Michael May, Belmont, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 18/166,774

(22) Filed: Feb. 9, 2023

(65) Prior Publication Data

US 2023/0241235 A1 Aug. 3, 2023

Related U.S. Application Data

(63) Continuation of application No. 16/342,275, filed as application No. PCT/IB2017/056093 on Oct. 3, 2017.

(60) Provisional application No. 62/409,081, filed on Oct. 17, 2016.

(51) Int. Cl.
*A61K 47/68* (2017.01)
*A61P 35/00* (2006.01)
*C07K 16/18* (2006.01)
*A61K 38/08* (2019.01)

(52) U.S. Cl.
CPC ...... *A61K 47/6803* (2017.08); *A61K 47/6843* (2017.08); *A61P 35/00* (2018.01); *C07K 16/18* (2013.01); *A61K 38/08* (2013.01); *A61K 47/6811* (2017.08); *C07K 2317/21* (2013.01); *C07K 2317/33* (2013.01); *C07K 2317/52* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 5,663,149 | A | 9/1997 | Pettit et al. |
|---|---|---|---|
| 5,952,329 | A | 9/1999 | Cincotta et al. |
| 7,273,924 | B1 | 9/2007 | Neri et al. |
| 7,314,622 | B2 | 1/2008 | Arlen et al. |
| 8,097,254 | B2 | 1/2012 | Neri et al. |
| 8,263,041 | B2 | 9/2012 | Rybak et al. |
| 8,481,681 | B2 | 7/2013 | Rybak et al. |
| 8,491,906 | B2 | 7/2013 | Borsi et al. |
| 8,679,488 | B2 | 3/2014 | Kaspar et al. |
| 8,703,143 | B2 | 4/2014 | Neri et al. |
| 8,828,401 | B2 | 9/2014 | Doroski et al. |
| 8,945,571 | B2 | 2/2015 | Mössner et al. |
| 9,096,670 | B2 | 8/2015 | Neri et al. |
| 9,138,486 | B2 | 9/2015 | Doroski et al. |
| 9,181,347 | B2 | 11/2015 | Rybak et al. |
| 9,198,979 | B2 | 12/2015 | Giulio |
| 9,249,186 | B2 | 2/2016 | Doroski et al. |
| 9,446,124 | B2 | 9/2016 | Kaspar et al. |
| 2002/0197262 | A1 | 12/2002 | Hasan et al. |
| 2003/0032995 | A1 | 2/2003 | Handy et al. |
| 2015/0030536 | A1 | 1/2015 | Neri et al. |
| 2017/0028080 | A1 | 2/2017 | Casi et al. |
| 2017/0151341 | A1 | 6/2017 | Ma et al. |
| 2017/0216452 | A1 | 8/2017 | Ma et al. |

FOREIGN PATENT DOCUMENTS

| CA | 2937731 | 7/2015 | |
|---|---|---|---|
| CN | 103649114 A | 3/2014 | |
| WO | 97/45544 A1 | 12/1997 | |
| WO | 99/58570 A2 | 11/1999 | |
| WO | 01/62298 A2 | 8/2001 | |
| WO | 01/62800 A1 | 8/2001 | |
| WO | 03/055917 A2 | 7/2003 | |
| WO | 2004/012735 A2 | 2/2004 | |
| WO | 2006/119897 A2 | 11/2006 | |
| WO | 2007/128557 A1 | 11/2007 | |
| WO | 2010/093395 A1 | 8/2010 | |
| WO | 2012/059882 A2 | 5/2012 | |
| WO | 2013/072813 A2 | 5/2013 | |
| WO | 2013/093809 A1 | 6/2013 | |
| WO | 2014/124316 A2 | 8/2014 | |
| WO | 2015/110935 A1 | 7/2015 | |
| WO | 2015/114166 A2 | 8/2015 | |
| WO | WO-2015114166 A2 * | 8/2015 | ........... A61K 47/555 |
| WO | 2015/162563 A1 | 10/2015 | |

(Continued)

OTHER PUBLICATIONS

Berndt et al., "Evidence of ED-B+ fibronectin synthesis in human tissues by non-radioactive RNA in situ hybridization. Investigations on carcinoma (oral squamos cell and breast carcinoma), chronic inflammation (rheumatoid synovitis) and fibromatosis (Morbus Dupuytren)", Histochem Cell Biol 109:249-255 (1998).

Birchler et al., "Selective targeting and photocoagulation of ocular angiogenesis mediated by a phage-derived human antibody fragment", Nature Biotechnology 17:984-988 (1999).

Boger et al, "CC-1065 and the duocarmycins: Unraveling the keys to a new class of naturally derived DNA alkylating agents", Proceedings of the National Academy of Sciences USA 92:3642-3649 (1995).

Borsi et al, "Selective Targeting of Tumoral Vasculature: Comparison of Different Formats of an Antibody (L19) to the ED-B Domain of Fibronectin", Int. J. Cancer 102:75-85 (2002).

Carnemolla et al, "A Tumor-associated Fibronectin Isoform Generated by Alternative Splicing of Messenger RNA Precursors", The Journal of Cell Biology 108:1139-1148 (1989).

(Continued)

*Primary Examiner* — Brian Gangle
*Assistant Examiner* — Andrea K McCollum
(74) *Attorney, Agent, or Firm* — Saul Ewing LLP; Kathryn Doyle; Domingos J. Silva

(57) ABSTRACT

The present invention provides antibodies and antibody-drug conjugates that bind to the extra domain B splice variant of fibronectin 1 and methods for preparing and using the same.

25 Claims, 23 Drawing Sheets

Specification includes a Sequence Listing.

(56) References Cited

FOREIGN PATENT DOCUMENTS

| WO | 2017/093844 A1 | 6/2017 |
| WO | 2017/093845 A1 | 6/2017 |

OTHER PUBLICATIONS

Carnemolla et al, "Phage Antibodies with Pan-Species Recognition of the Oncofoetal Angiogenesis Marker Fibronectin ED-B Domain", Int. J. Cancer 68:397-405 (1996).
Casi et al, "Site-Specific Traceless Coupling of Potent Cytotoxic Drugs to Recombinant Antibodies for Pharmacodelivery", Journal of the American Chemical Society 134:5887-5892 (2012).
Chothia et al, "Conformations of immunoglobulin hypervariable regions", Nature 342:877-883 (1989).
Danielli et al, "Intralesional administration of L19-IL2/L19-TNF in stage III for stage IVM1a melanoma patients: results of a phase II study", Cancer Immunol Immunother 64:999-1009 (2015).
Edelman et al, "The Covalent Structure of an Entire gammaG Immunoglobulin Molecule", Proc. Natl. Acad. Sci. USA 63(1):78-85 (1969).
Fabbrini et al, "Selective occlusion of tumor blood vessels by targeted delivery of an antibody-photosensitizer conjugate", Int. J. Cancer 118:1805-1813 (2006).
Fellouse et al, "High-throughput Generation of Synthetic Antibodies from Highly Functional Minimalist Phase-displayed Libraries", J Mol Biol 373(4):924-940 (2007).
Gébleux et al, "Antibody Format and Drug Release Rate Determine the Therapeutic Activity of Noninternalizing Antibody-Drug Conjugates", Molecular Cancer Therapeutics 14(11):2606-2612 (2015).
Giovannoni et al, "Isolation of anti-angiogenesis antibodies from a large combinatorial repertoire by colony filter screening", Nucleic Acids Research 29(5):e27 (2001).
Halin et al, "Synergistic Therapeutic Effects of a Tumor Targeting Antibody, Fused to Interleukin 12 and to Tumor Necrosis Factor alpha", Cancer Research 63(12):3202-3210 (2003).
Holliger et al, "Engineered antibody fragments and the rise of single domains", Nature Biotechnology 23(9):1126-1136 (2005).
Hötzel et al, "A strategy for risk mitigation of antibodies with fast clearance", mAbs 4(6):753-760 (2012).
Jayasena, "Aptamers: An Emerging Class of Molecules That Rival Antibodies in Diagnostics", Clinical Chemistry 45(9):1628-1650 (1999).
Kaczmarek et al, "Distribution of Oncofetal Fibronectin Isoforms in Normal, Hyperplastic and Neoplastic Human Breast Tissues", Int. J. Cancer 58:11-16 (1994).
Kunkel, "Rapid and efficient site-specific mutagenesis without phenotypic selection", Proceedings of the National Academy of Sciences USA 82:488-492 (1985).
Li et al, "RSEM: accurate transcript quantification from RNA-Seq data with or without a reference genome", BMC Bioinformatics 12:323 (2011) (16 pages).
Mac Callum et al, "Antibody-antigen Interactions: Contact Analysis and Binding Site Topography", J Mol Biol 262(5):732-745 (1996).
Makabe et al, "Thermodynamic Consequences of Mutations in Vernier Zone Residues of a Humanized Anti-human Epidermal Growth Factor Receptor Murine Antibody, 528", The Journal of Biological Chemistry 283(2):1156-1166 (2008).
Neri et al, "Targeting by affinity-matured recombinant antibody fragments of angiogenesis associated fibronectin soform", Nature Biotechnology 15:1271-1275 (1997).

Nicolaou et al, "Calicheamicin θI1: A Rationally Designed Molecule with Extremely Potent and Selective DNA Cleaving Properties and Apoptosis Inducing Activity", Angew. Chem. Int. Ed. Engl. 33(2):183-186 (1994).
Nicolaou et al, "Synthetic calicheamicin mimics with novel initiation mechanisms: DNA cleavage, cytotoxicity, and apoptosis", Chemistry & Biology 1(1):57-66 (1994).
Palumbo et al, "A chemically modified antibody mediates complete eradication of tumours by selective disruption of tumour blood vessels", British Journal of Cancer 104(7):1106-1115 (2011).
PCT International Search Report and Written Opinion for International Patent Application No. PCT/IB2017/056093 dated Dec. 15, 2017.
Perrino et al, "Curative Properties of Noninternalizing Antibody-Drug Conjugates Based on Maytansinoids", Cancer Research 74(9):2569-2578 (2014).
Pettit et al, "Specific Activities of Dolastatin 10 and Peptide Derivatives against Cryptococcus neoformans", Antimicrobial Agents and Chemotherapy 42(11):2961-2965 (1998).
Pini et al, "Design and Use of a Phage Display Library. Human Antibodies with Subanomolar Affinity Against a Marker of Angiogenesis Eluted From a Two-Dimensional Gel", The Journal of Biological Chemistry 273(34):21769-21776 (1998).
Prokop et al, "Induction of apoptosis by enediyne antibiotic calicheamicin θII proceeds through a caspase-mediated mitochondrial amplification loop in an entirely Bax-dependent manner.", Oncogene 22(57):9107-9120 (2003).
Remillard et al, "Antimitotic Activity of the Potent Tumor Inhibitor Maytansine", Science 189:1002-1005 (1975).
Schlothauer et al, "Analytical FcRn affinity chromatography for functional characterization of monoclonal antibodies", mAbs 5(4):576-586 (2013).
Schoch et al, "Charge-mediated influence of the antibody variable domain on FcRn-dependent pharmacokinetics", PNAS 112(19):5997-6002 (2015).
Schwager et al, "The Immunocytokine L19-IL2 Eradicates Cancer When Used in Combination with CTLA-4 Blockade or with L19-TNF", Journal of Investigative Dermatology 133:751-758 (2013).
Tiller et al, "Efficient generation of monoclonal antibodies from single human B cells by single cell RT-PCR and expression vector cloning", Journal of Immunological Methods 329:112-124 (2008).
Viti et al, "Increased Binding Affinity and Valence of Recombinant Antibody Fragments Lead to Improved Targeting of Tumoral Angiogenesis", Cancer Research 59(2):347-352 (1999).
Xu et al, "Addressing polyspecificity of antibodies selected from an in vitro yeast presentation system: a FACS-based, high-throughput selection and analytical tool", Protein Engineering, Design & Selection 26(10):663-670 (2013).
Zardi et al, "Transformed human cells produce a new fibronectin isoform by preferential alternative splicing of a previously unobserved exon", The EMBO Journal 6(8):2337-2342 (1987).
Zein et al, "Calicheamicin γ1I: An Antitumor Antibiotic That Cleaves Double-Stranded DNA Site Specifically", Science 240(4856):1198-1201 (1988).
Zoller et al, "Oligonucleotide-directed mutagenesis using M13-derived vectors: an efficient and general procedure for the production of point mutations in any fragment of DNA", Nucleic Acids Research 10(20):6487-6500 (1982).
Wei et al, "Where Did the Linker-Payload Go? A Quantitative Investigation on the Destination of the Released Linker-Payload from an Antibody-Drug Conjugate with a Maleimide Linker in Plasma", Analytical Chemistry 88(9):4979-4986 (2016).

* cited by examiner

ANTI-EDB ANTIBODIES AND ANTIBODY-DRUG CONJUGATES

CROSS-REFERENCE TO RELATED APPLICATIONS

This application is a continuation of, and claims priority to, U.S. patent application Ser. No. 16/342,275 filed Apr. 16, 2019, which is a 35 U.S.C. § 371 national phase application of, and claims priority to, International Application No. PCT/IB2017/056093 filed Oct. 3, 2017, which claims priority under 35 U.S.C. § 119(e) to U.S. Provisional Patent Application No. 62/409,081, filed Oct. 17, 2016, all of which are hereby incorporated herein by reference in their entirety entireties.

REFERENCE TO SEQUENCE LISTING

This disclosure contains one or more sequences in a computer readable format in an accompanying file titled "384953-1001US2(00149) Sequence Listing.xml," which is 86.7 KB in size and was created Feb. 9, 2023, the contents of which are incorporated herein by reference in their entireties.

FIELD OF THE INVENTION

The present invention relates to anti-EDB antibodies and EDB antibody-drug conjugates (ADCs). The present invention further relates to the methods of using such antibodies and ADCs for the treatment of EDB+ FN-expressing disorders, such as cancer.

BACKGROUND OF THE INVENTION

Fibronectins are high-molecular-weight adhesive glycoproteins present in soluble form in plasma and other body fluids, and in insoluble form in the extracellular matrix (ECM). The extra domain B splice variant of fibronectin 1 (EDB+ FN or EDB) is a non-internalizing ECM protein. EDB is a 91 amino acid type III homology domain that is inserted into the fibronectin molecule by a mechanism of alternative splicing at the level of the primary transcript whenever tissue remodeling takes place. EDB+ FN has been shown to selectively accumulate in the stroma around new blood vessels in tumors and other pathologies, but to be largely absent in normal adult vasculature. Zardi et al., Embo J. 6(8): 2337-42 (1987). EDB+ FN is expressed in many aggressive tumors and depending on the tumor type displays either predominantly vascular or diffuse stromal patterns of expression. Carnemolla et al., J. Cell Biol. 108(3): 1139-48 (1989).

An antibody that specifically binds to the EDB domain of fibronectin (FN), the L19 antibody, has been isolated by phage display technology. Carnemolla et al., Int. J. Cancer 68(3): 397-405 (1996); Neri et al., Nat. Biotechnol. 15(12): 1271-5. (1997); Pini et al., J. Biol. Chem. 273(34): 21769-76 (1998). The L19 antibody is able to stain tumor blood vessels in a wide range of experimental tumor models and on sections of human tumors and other angiogenic disorders. Carnemolla et al., J. Cell Biol. 108(3): 1139-48 (1989); Kaczmarek et al., Int. J. Cancer 59(1): 11-6 (1994); Berndt et al., Histochem. Cell Biol. 109(3): 249-55 (1998).

Various targeting strategies have been explored using different formats of the L19 antibody in the treatment of cancer. For example, a scFv(L19) monoclonal antibody fragment, Birchler et al. Nat Biotechnol. 17: 984-8 (1999), fusion proteins including interleukin-12 (IL-12) and tumor necrosis factor (TNF-alpha) fused with scFv(L19), Halin C. et al. Cancer Res. 63(12):3202-10 (2003) and L19 small immune protein (SIP) alone and conjugated to a photosensitizer, Fabbrini M. et al. Int J Cancer 118(7):1805-13 (2006).

Although various L19 antibody based therapies have been disclosed, there remains a significant clinical need for the development of further improved and optimized EDB+ FN-targeting therapies, such as antibody-drug conjugates, for those patients with EDB+ FN-expressing disorders or diseases, such as cancers associated with EDB+ FN expression and/or EDB+ FN-expressing cancers.

SUMMARY OF THE INVENTION

The present invention provides for, an antibody-drug conjugate comprising (a) an antibody, or antigen binding fragment thereof, that binds to extra domain B (EDB) of fibronectin (FN), (b) a linker and (c) a drug. In some aspects, an antibody-drug conjugate comprises an antibody, or antigen binding fragment, may comprise a heavy chain variable region comprising three CDRs comprising SEQ ID NOs: 3, 5 and 7, and a light chain variable region comprising three CDRs comprising SEQ ID NOs: 12, 13 and 14. In some aspects, an antibody-drug conjugate comprises an antibody, or antigen binding fragment, may comprise a heavy chain variable region comprising SEQ ID NO: 1 or 21, and a light chain variable region comprising SEQ ID NO: 10.

The present invention also provides for an antibody-drug conjugate comprising an antibody, or antigen binding fragment, may comprise a heavy chain variable region comprising SEQ ID NO: 1 and a light chain variable region comprising SEQ ID NO: 10; or a heavy chain variable region comprising SEQ ID NO: 21 and a light chain variable region comprising SEQ ID NO: 10. In some aspects, an antibody-drug conjugate comprises an antibody, or antigen binding fragment, comprises a heavy chain comprising SEQ ID NO: 8, 17, 19, 23, 25, 27 or 29, and a light chain comprising SEQ ID NO: 15 or 31.

The present invention also provides for an antibody-drug conjugate comprising an antibody, or antigen binding fragment, comprising a heavy chain comprising SEQ ID NO: 8 and a light chain comprising SEQ ID NO: 15; a heavy chain comprising SEQ ID NO: 8 and a light chain comprising SEQ ID NO: 31; a heavy chain comprising SEQ ID NO: 17 and a light chain comprising SEQ ID NO: 15; a heavy chain comprising SEQ ID NO: 17 and a light chain comprising SEQ ID NO: 31; a heavy chain comprising SEQ ID NO: 19 and a light chain comprising SEQ ID NO: 15; a heavy chain comprising SEQ ID NO: 19 and a light chain comprising SEQ ID NO: 31; a heavy chain comprising SEQ ID NO: 23 and a light chain comprising SEQ ID NO: 15; a heavy chain comprising SEQ ID NO: 23 and a light chain comprising SEQ ID NO: 31; a heavy chain comprising SEQ ID NO: 25 and a light chain comprising SEQ ID NO: 15; a heavy chain comprising SEQ ID NO: 25 and a light chain comprising SEQ ID NO: 31; a heavy chain comprising SEQ ID NO: 27 and a light chain comprising SEQ ID NO: 15; a heavy chain comprising SEQ ID NO: 27 and a light chain comprising SEQ ID NO: 31; a heavy chain comprising SEQ ID NO: 29 and a light chain comprising SEQ ID NO: 15; or a heavy chain comprising SEQ ID NO: 29 and a light chain comprising SEQ ID NO: 31.

The present invention also provides for an antibody-drug conjugate comprising an antibody, or antigen binding fragment, having a heavy chain and/or light chain constant region comprising an engineered cysteine residue for site-specific conjugation. In some aspects, an antibody-drug conjugate has a heavy chain constant region comprising an engineered cysteine residue at positon 290 (K290C), according to the numbering of the EU index of Kabat. In some aspects, an antibody-drug conjugate has a light chain constant region comprising an engineered cysteine residue at positon 183 (κK183C), according to the numbering of Kabat. In some aspects, an antibody-drug conjugate has a heavy chain constant region comprising an engineered cysteine residue at positon 290 (K290C), according to the numbering of the EU index of Kabat, and a light chain constant region comprises an engineered cysteine residue at positon 183 (κK183C), according to the numbering of Kabat.

The present invention further provides for an antibody-drug conjugate having an antibody, or antigen binding fragment, comprising a heavy chain constant region comprising an engineered glutamine-containing tag inserted in the antibody or replacing one or more endogenous amino acids in the antibody. In some aspects, an antibody-drug conjugate has an engineered glutamine-containing tag inserted in the antibody at position E294-N297. In some aspects, an antibody-drug conjugate has a glutamine-containing tag comprising an amino acid sequence LLQG (SEQ ID NO: 40). In some aspects, an antibody-drug conjugate having a heavy chain constant region further comprising a lysine (K) substituting an arginine (R) at position 222 (K222R), according to the numbering of the EU index of Kabat.

The present invention also provides for an antibody-drug conjugate of having an antibody, or antigen binding fragment, comprising a heavy chain variable region comprising a lysine (K) substituting an arginine (R) at position 94 (K94R), according to the numbering of Kabat.

The present invention further provides for an antibody-drug conjugate having a linker that is a cleavable linker. In some aspects, the cleavable linker is selected from the group consisting of vc, diS, diS-C₂OCO and AcLys-vc.

The present invention further provides for an antibody-drug conjugate having a drug that is a cytotoxic agent. In some aspects, the cytotoxic agent is an auristatin. In some aspects, the auristatin is selected from the group consisting of 0101, 1569, 9411 and 4574. In some aspects the cytotoxic agent is a CPI dimer. In some aspects, the CPI dimer is CPI-8314 or CPI-0326.

The present invention also provides for an antibody-drug conjugate comprising (a) an antibody, or antigen binding fragment thereof, comprising a heavy chain variable region comprising three CDRs comprising SEQ ID NOs: 3, 5 and 7, and a light chain variable region comprising three CDRs comprising SEQ ID NOs: 12, 13 and 14, (b) a vc linker and (c) a 0101 drug.

The present invention also provides for an antibody-drug conjugate comprising (a) an antibody, or antigen binding fragment thereof, comprising a heavy chain variable region comprising SEQ ID NO: 21 and a light chain variable region comprising SEQ ID NO: 10; (b) a vc linker and (c) a 0101 drug.

The present invention also provides for an antibody-drug conjugate comprising (a) an antibody, or antigen binding fragment thereof, comprising a heavy chain comprising SEQ ID NO: 25 and a light chain comprising SEQ ID NO: 31; (b) a vc linker and (c) a 0101 drug.

The present invention further provides for a pharmaceutical composition comprising an antibody-drug conjugate of the invention and a pharmaceutically acceptable carrier. The present invention also provides for a composition comprising a plurality of an antibody-drug conjugates of the invention, and optionally a pharmaceutical carrier, wherein the composition has an average DAR of ranging from 3 to 5. The present invention also provides for a composition comprising a plurality of an antibody-drug conjugates of any one of claims 1-25, and optionally a pharmaceutical carrier, wherein the composition has an average DAR of ranging from 1 to 3.

The present invention provides for a nucleic acid encoding a heavy chain or a light chain of an antibody of the invention. In some aspects the nucleic acid may comprise SEQ ID NOs: 9, 18, 20, 24, 26, 28 or 30 encoding a heavy chain or may comprise SEQ ID NOs: 16 or 32 encoding a light chain. The present invention further provides for a vector comprising any nucleic acid of the invention. Also, the present invention provides for a host cell comprising any nucleic acid of the invention.

The present invention provides a process for producing an antibody-drug conjugate of the invention comprising: (a) linking the linker to the drug; (b) conjugating the linker and drug to the antibody; and (c) purifying the antibody-drug conjugate. In some aspects, the conjugating is site-specific on one or more engineered cysteine residue and/or engineered glutamine residues on the antibody.

The present invention also provides a method of treating an EDB+ FN-expressing disorder or disease, comprising administering an effective amount of a composition comprising an antibody-drug conjugate of the invention to a subject in need thereof. In some aspects, the EDB+ FN-expressing disorder or disease is cancer. In some aspects, the cancer is a solid tumor or blood cancer. In some aspects, the solid tumor is thyroid cancer, sarcoma, breast cancer, pancreatic cancer, glioblastoma, gallbladder cancer, kidney cancer, skin cancer, uterine cancer, mesothelioma, colorectal cancer, head and neck cancer, ovarian cancer, bladder cancer, testicular cancer, prostate cancer, liver cancer, endocrine cancer, thymus cancer, brain cancer, adrenal cancer, eye cancer cervical cancer and lung cancer. In some aspects, the blood cancer is leukemia, lymphoma or myeloma.

The present invention further provides for the use of an antibody-drug conjugate of the invention, in the manufacture of a medicament for the treatment of an EDB+ FN-expressing disorder or disease in a subject. In some aspects, the EDB+ FN-expressing disorder or disease is cancer. In some aspects, the cancer is a solid tumor or blood cancer. In some aspects, the solid tumor is thyroid cancer, sarcoma, breast cancer, pancreatic cancer, glioblastoma, gallbladder cancer, kidney cancer, skin cancer, uterine cancer, mesothelioma, colorectal cancer, head and neck cancer, ovarian cancer, bladder cancer, testicular cancer, prostate cancer, liver cancer, endocrine cancer, thymus cancer, brain cancer, adrenal cancer, eye cancer cervical cancer and lung cancer. In some aspects, the blood cancer is leukemia, lymphoma or myeloma.

K94R-290C)-vc-0101 ADC; and [B] EDB-(K94R) antibody and EDB-(K94R)-vc-0101 ADC, and EDB-(κK183C–K290C) antibody and EDB-(κK183C–K290C)-vc0101 ADC.

Figure 4:
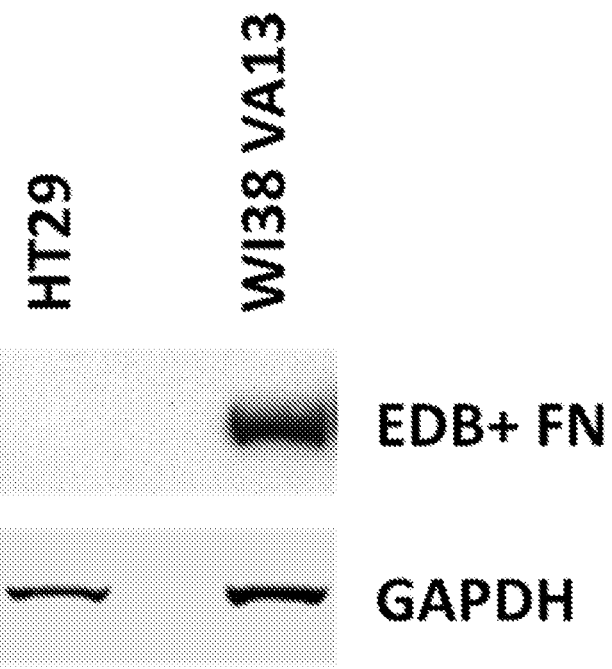

FIG. 4 shows EDB+ FN expression by western blot in WI38-VA13 and HT-29 cells.

FIGS. 5A-5F show anti-tumor efficacy in PDX-NSX-11122, a high EDB+ FN expressing NSCLC patient derived xenograft (PDX) model of human cancer, of [A] EDB-L19-vc-0101 at 0.3, 0.75, 1.5 and 3 mg/kg; [B] EDB-L19-vc-0101 at 3 mg/kg and 10 mg/kg of disulfide linked EDB-L19-diS-DM1; [C] EDB-L19-vc-0101 at 1 and 3 mg/kg and 5 mg/kg of disulfide linked EDB-L19-diS-$C_2$OCO-1569; [D] site-specific conjugated EDB-(κK183C+K290C)-vc-0101 and conventionally conjugated EDB-L19-vc-0101 (ADC1) at the doses of 0.3, 1 and 3 mg/kg and 1.5 mg/kg, respectively; [E] site-specific conjugated EDB-(κK183C-K94R-K290C)-vc-0101 at the doses of 0.3, 1 and 3 mg/kg; and [F] EDB-(κK183C-K94R-K290C)-vc-0101 group dosed at 3 mg/kg as tumor growth inhibition curves for each individual tumor bearing mouse.

FIGS. 6A-6F show anti-tumor efficacy in H-1975, a moderate to high EDB+ FN expressing NSCLC cell line xenograft (CLX) model of human cancer, of [A] EDB-L19-vc-0101 at 0.3, 0.75, 1.5 and 3 mg/mg; [B] EDB-L19-vc-0101 and EDB-L19-vc-1569 at 0.3, 1 and 3 mg/kg; [C] EDB-L19-vc-0101 and EDB-(H16-K222R)-AcLys-vc-CPI-8314 at 0.5, 1.5 and 3 mg/kg and 0.1, 0.3 and 1 mg/kg, respectively; [D] site-specific conjugated EDB-(κK183C+K290C)-vc-0101 and conventionally conjugated EDB-L19-vc-0101 at 0.5, 1.5 and 3 mg/kg; [E] EDB-L19-vc-0101 and EDB-(K94R)-vc-0101 at 1 and 3 mg/kg; and [F] EDB-(κK183C+K290C)-vc-0101 and EDB-(κK183C-K94R-K290C)-vc-0101 at 1 and 3 mg/kg.

Figure 7:
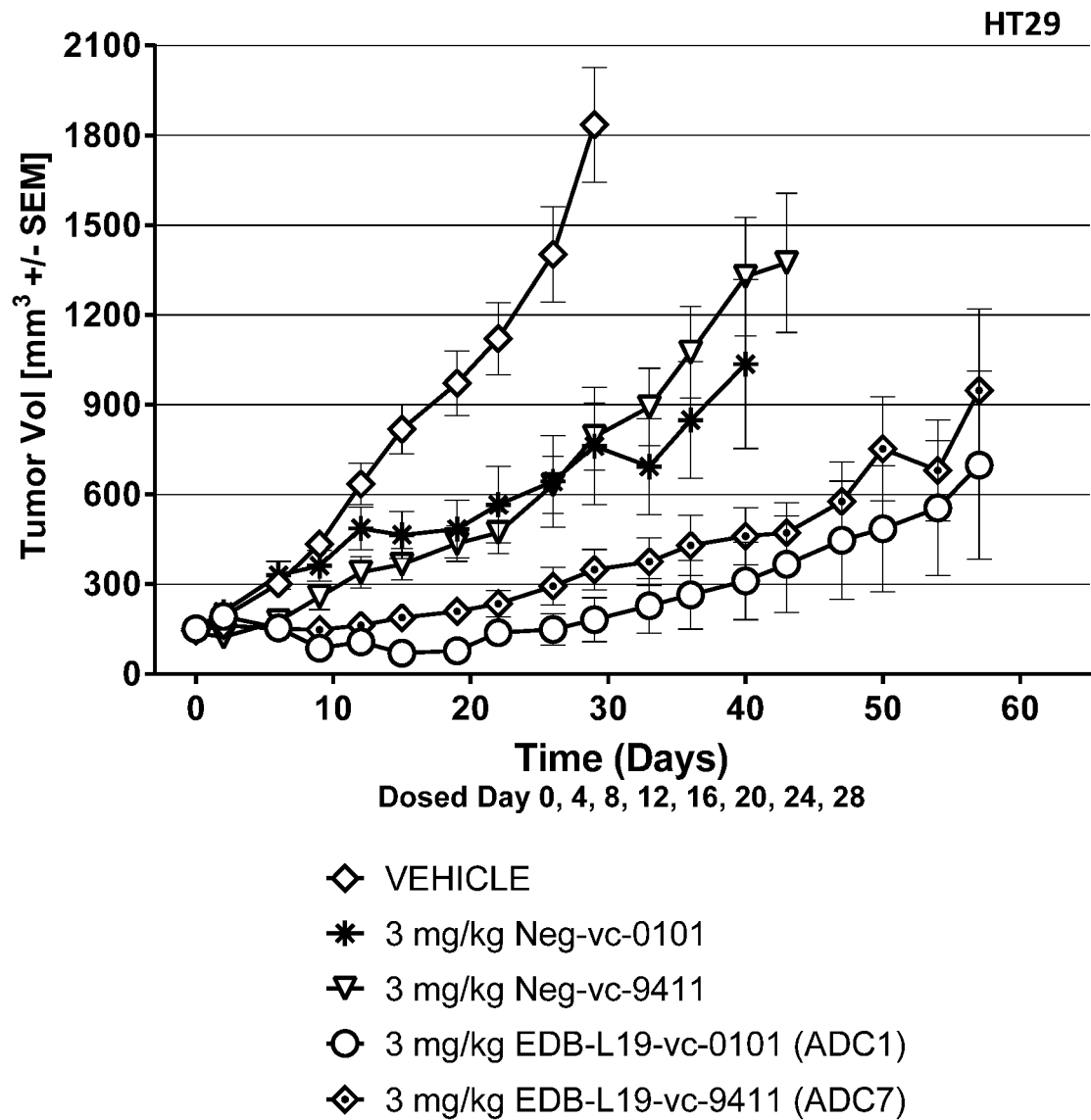

FIG. 7 shows anti-tumor efficacy in HT29, a moderate EDB+ FN expressing colon CLX model of human cancer, of EDB-L19-vc-0101 and EDB-L19-vc-9411 at 3 mg/kg.

Figure 8A:
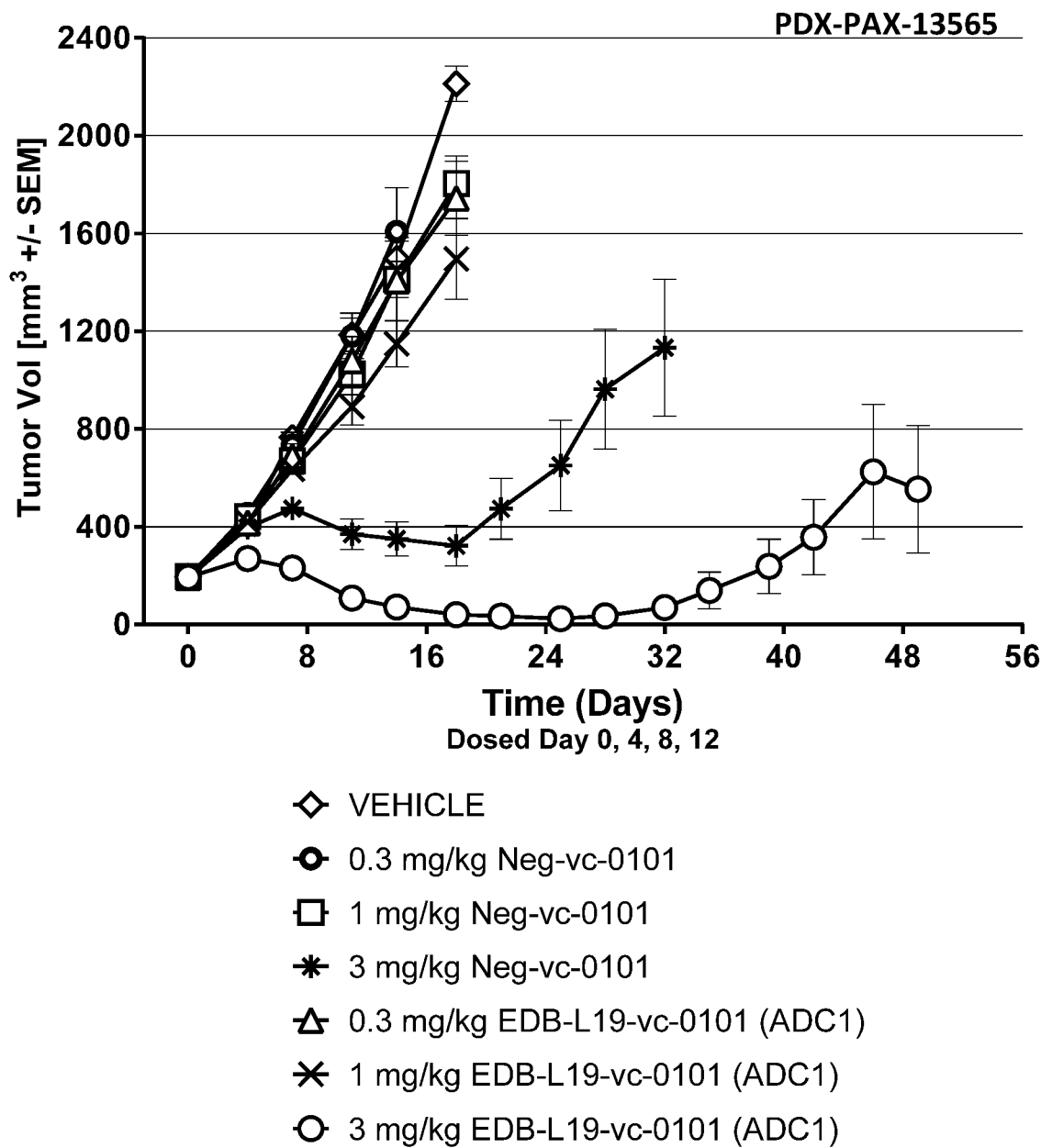
Figure 8B:
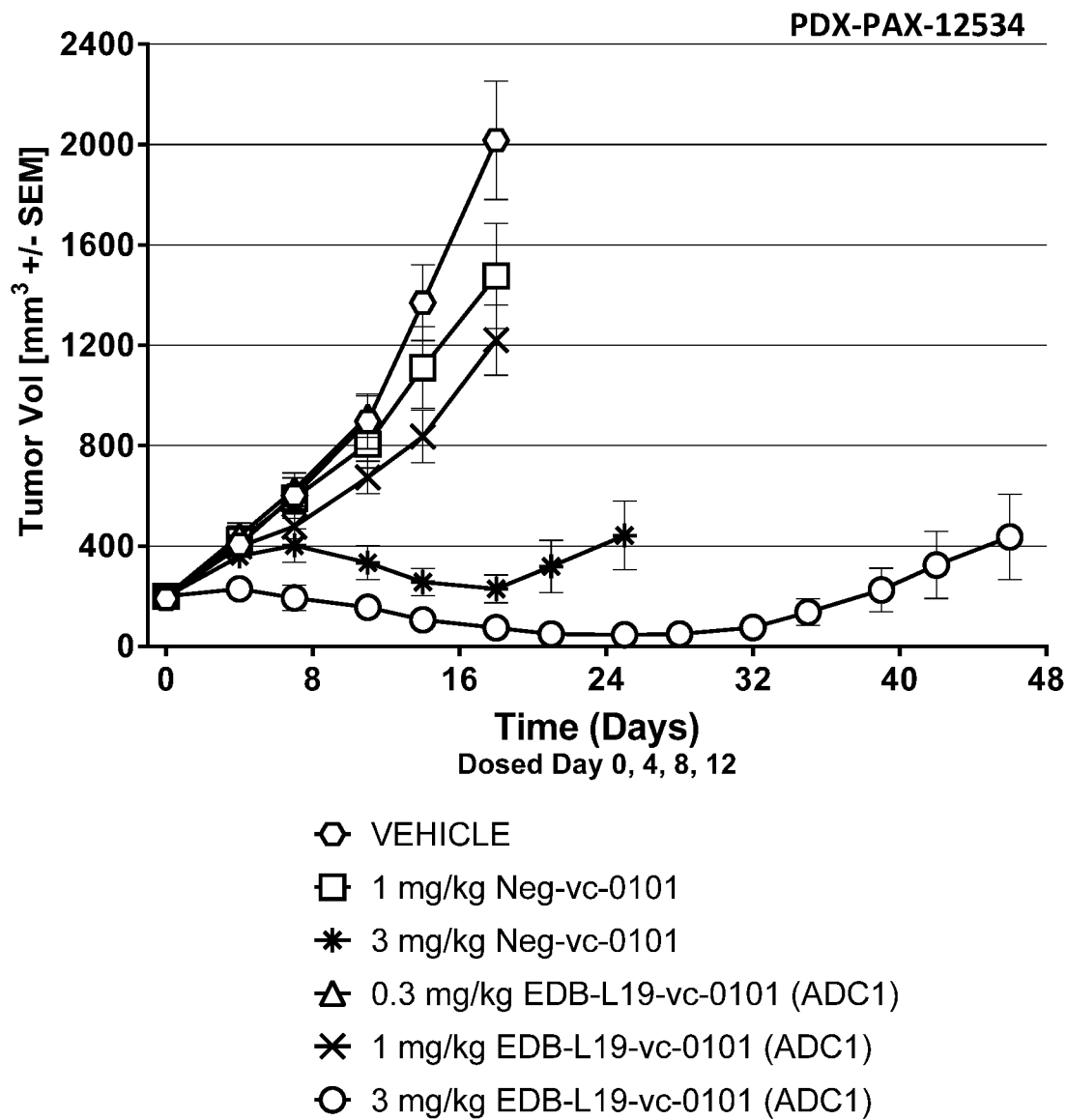

FIGS. 8A and 8B show anti-tumor efficacy of EDB-L19-vc-0101 at 0.3, 1 and 3 mg/kg in [A] PDX-PAX-13565, a moderate to high EDB+ FN expressing pancreatic PDX; and [B] PDX-PAX-12534, a low to moderate EDB+ FN expressing pancreatic PDX.

Figure 9:
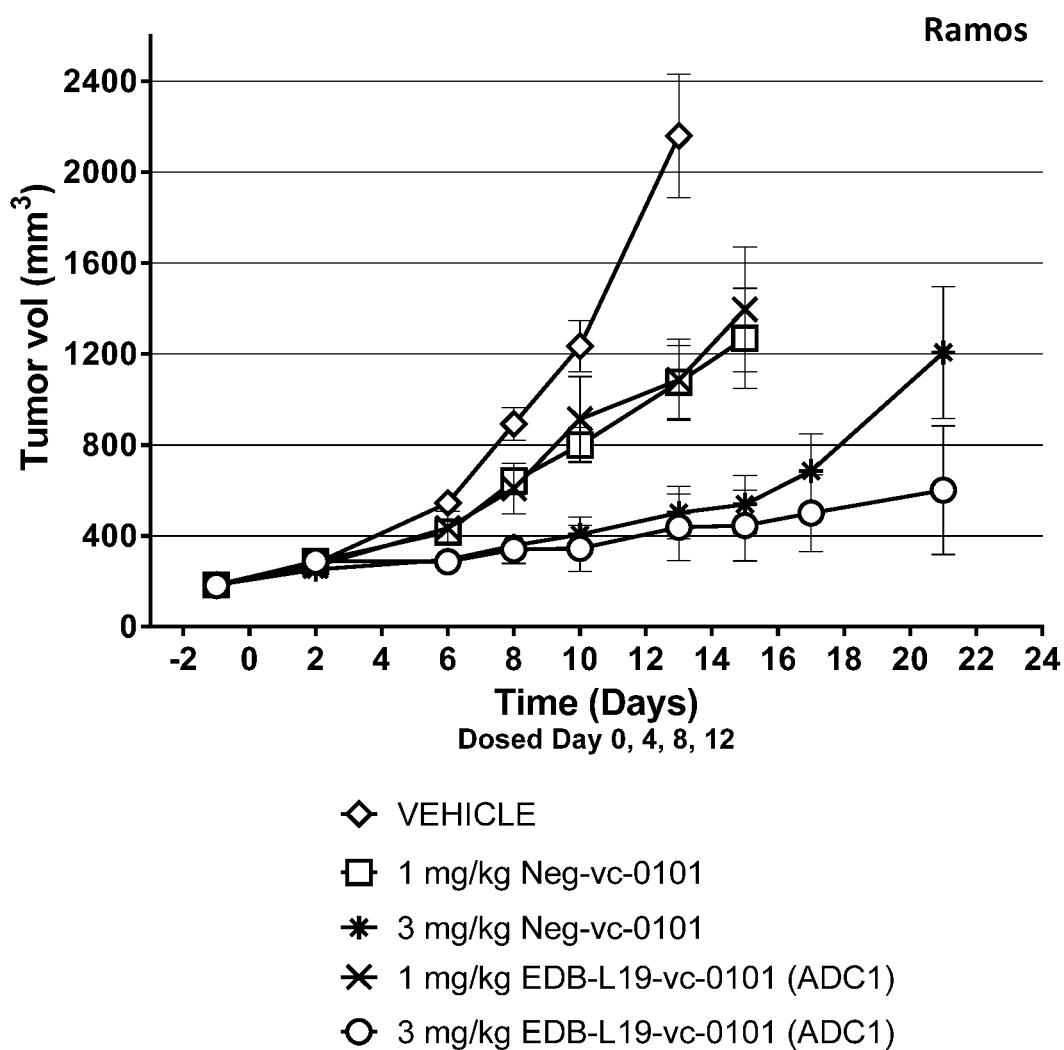

FIG. 9 shows anti-tumor efficacy of EDB-L19-vc-0101 at 1 and 3 mg/kg in Ramos, a moderate EDB+ FN expressing lymphoma CLX model of human cancer.

Figure 10A:
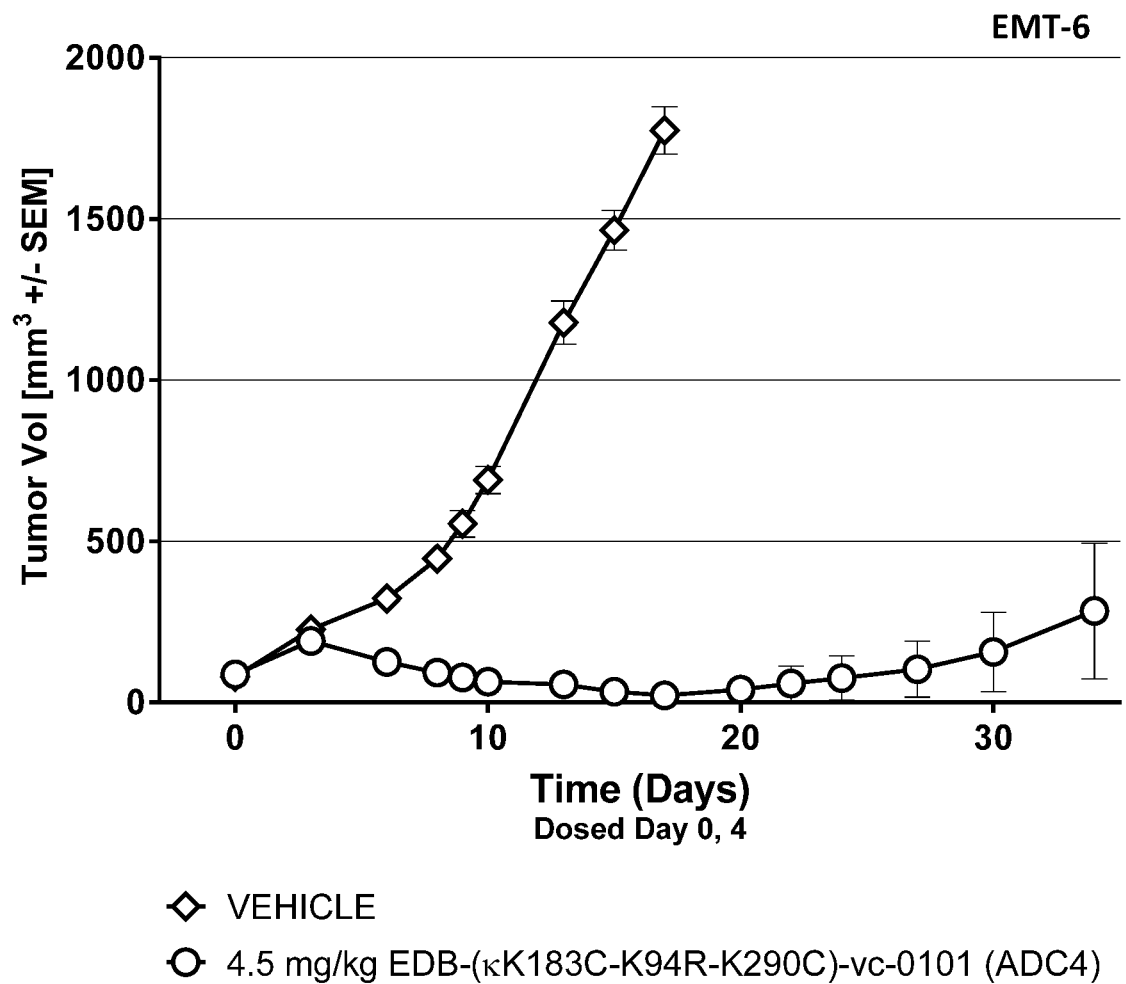
Figure 10B:
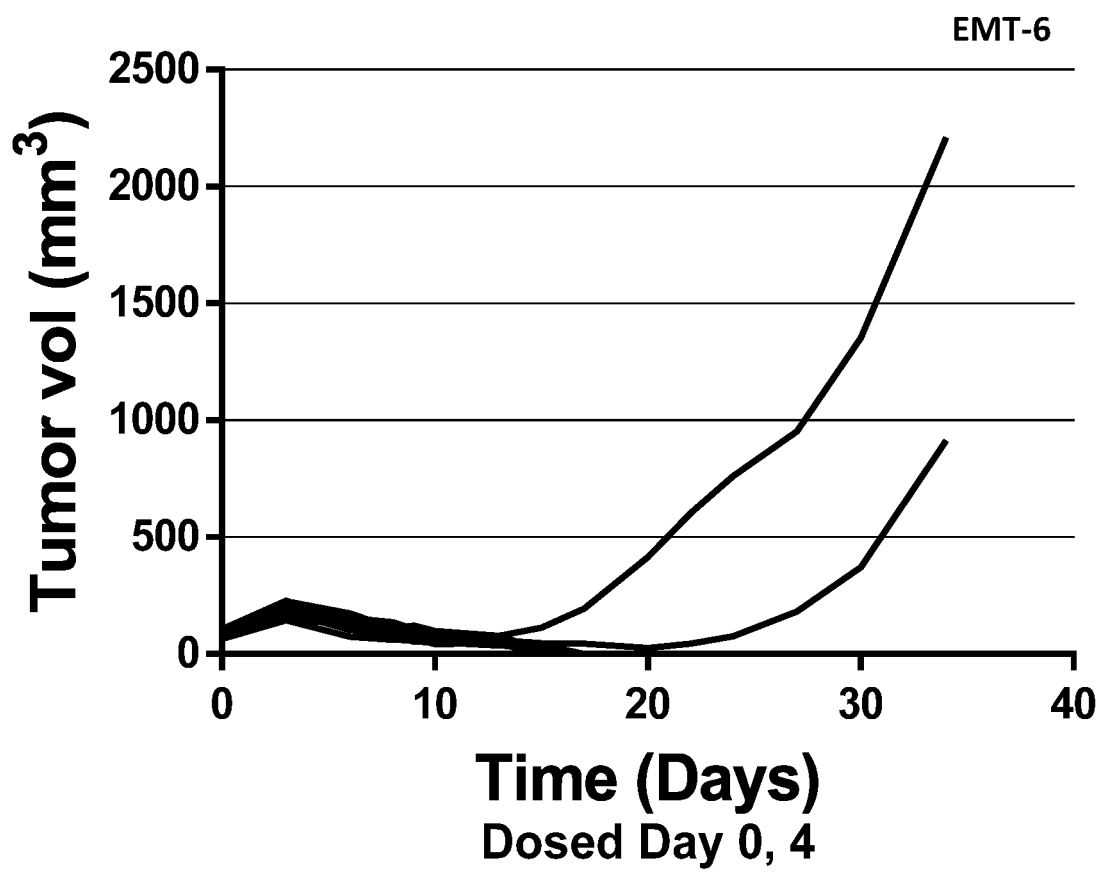

FIGS. 10A and 10B show the anti-tumor efficacy in EMT-6, a mouse syngeneic breast carcinoma model, of [A] EDB-(κK183C-K94R-K290C)-vc-0101 at 4.5 mg/kg; and [B] EDB-(κK183C-K94R-K290C)-vc-0101 group dosed at 4.5 mg/kg as tumor growth inhibition curves for each individual tumor bearing mouse.

Figure 11:
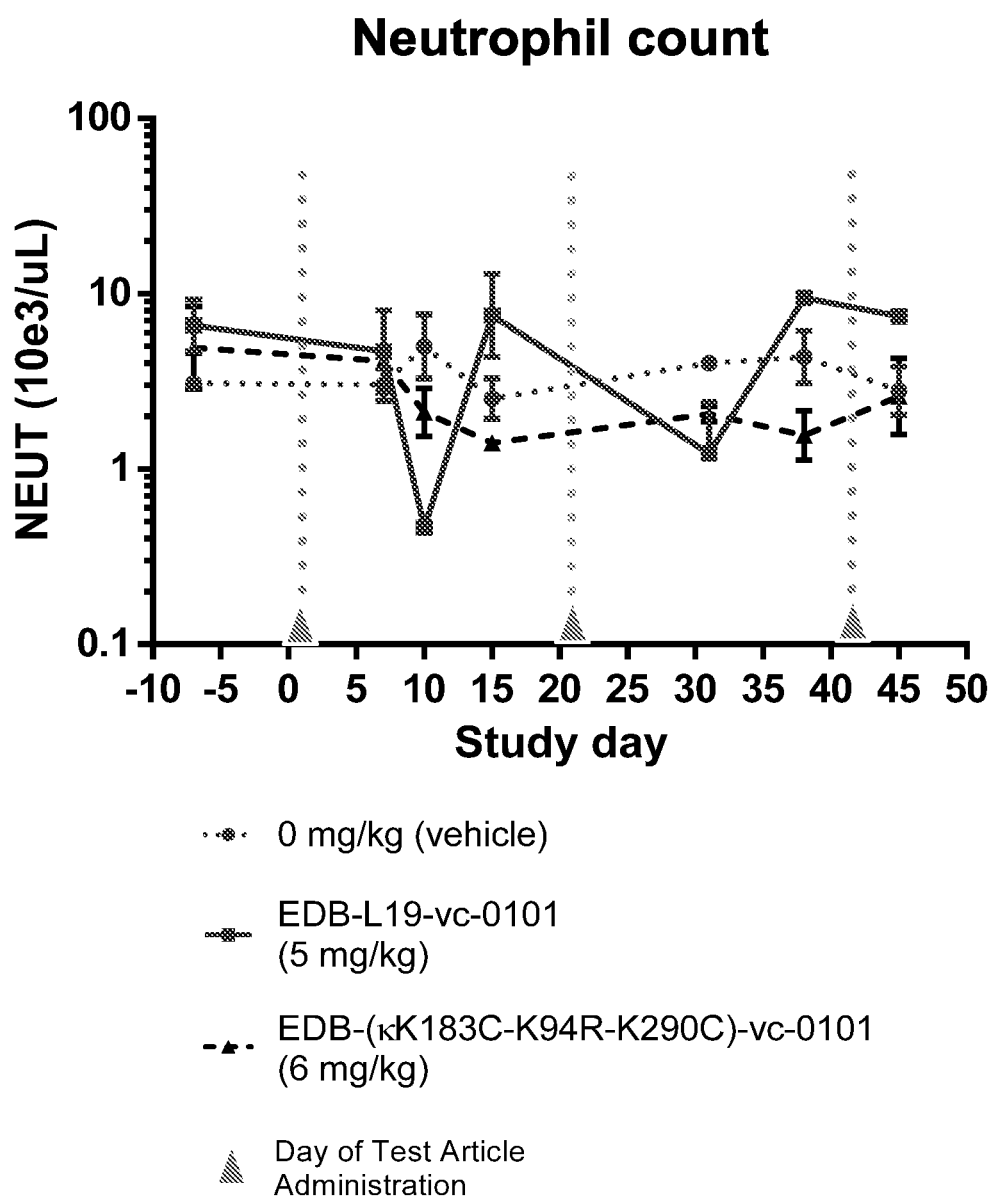

FIG. 11 shows absolute neutrophil counts for conventionally conjugated EDB-L19-vc-0101 at 5 mg/kg compared to site-specific conjugated EDB-(κK183C-K94R-K290C)-vc-0101 (ADC4) at 6 mg/kg.

DETAILED DESCRIPTION OF THE INVENTION

The present invention provides antibodies and antibody drug conjugates (ADCs) that bind to the extra-domain B (EDB) of fibronectin (FN), referred to as "EDB+ FN" or "EDB", interchangeably. The invention also provides processes for preparing the ADCs using anti-EDB antibodies, linkers, and drugs (payloads). The invention further provides for ADCs generated using conventional and/or site-specific conjugation technology. The antibodies and ADCs of the invention are useful for the preparation and manufacture of compositions, such as medicaments, that may be used in the diagnosis, prophylaxis, and/or treatment of hyperproliferative disorders characterized by or associated with EDB+ FN expression, such as cancer. The invention also provides for nucleic acids encoding the anti-EDB antibodies used in making the EDB ADCs.

ADCs comprise an antibody component conjugated to a drug, typically through the use of a linker. ADCs generated by conventional conjugation technology randomly link the drug to the antibody through lysine or cysteine residues that are endogenously on the antibody heavy and/or light chain. Accordingly, such ADCs are a heterogeneous mixture of species having different drug:antibody ratios (DAR). ADCs generated by site-specific conjugation technology link the drug to the antibody at particular engineered residues on the antibody heavy and/or light chain. As such, the site-specific conjugated ADCs are a homogeneous mixture of ADCs comprised of a species with a defined drug:antibody ratio (DAR). Thus, site-specific conjugated ADCs demonstrate uniform stoichiometry resulting in improved pharmacokinetics, biodistribution and safety profile.

ADCs of the present invention include anti-EDB antibodies conjugated to one or more drugs via a linker (i.e. forming linker-drug moieties). The present invention provides for ADCs having (a) an antibody, or antigen binding fragment thereof, that binds to EDB; (b) a linker and (c) a drug. The present invention further provides for ADCs of the formula Ab-(L-D), wherein (a) Ab is an antibody, or antigen-binding fragment thereof, that binds to EDB, and (b) L-D is a linker-drug moiety, wherein L is a linker, and D is a drug. In another aspect, the present invention provides for ADCs of the formula Ab-(L-D)p, wherein (a) Ab is an antibody, or antigen-binding fragment thereof, that binds to EDB, (b) L-D is a linker-drug moiety, wherein L is a linker, and D is a drug and (c)p is the number of linker-drug moieties attached to the antibody.

The number of linker-drug moieties attached to an antibody can be any number preferred for development of an ADC. In some aspects, the number of linker-drug moieties per antibody is 4. In other aspects, the number of linker-drug moieties per antibody is 3. In another aspect, the number of linker-drug moieties per antibody is 2. In another aspect, the number of linker-drug moieties per antibody is 1. In other aspects, the number of linker-drug moieties per antibody is greater than 4, such as 5, 6, 7, 8, 9, 10, 11, 12 or greater than 12 linker-drug moieties per antibody.

Further the present invention provides for ADCs, wherein the linker-drug moieties are attached to the antibody via conventional or site-specific conjugation technology. In some aspects, the anti-EDB antibodies, or antigen-binding fragments thereof, are conjugated or linked to a drug such as a cytotoxic, cytostatic, and/or therapeutic agent, as described further herein. For example, a cytotoxic agent can be linked or conjugated to an anti-EDB antibody as described herein for targeted local delivery of the cytotoxic agent. Also provided are methods of preparing and manufacturing such ADCs, and use of the same in clinical applications.

In contrast to other ADCs being developed to target internalizing cell surface expressed proteins, the ADCs of the present invention target EDB, a protein expressed in the extracellular matrix (ECM). Targeting a protein expressed in the ECM may provide benefits over targeting a protein expressed on the tumor cells. The ADC may directly access the target without having to penetrate through the stromal and ECM barriers common in many difficult-to-treat human cancers. Further, targeting EDB in the ECM with an ADC provides a specific mechanism to access many difficult to target cell types in the tumor microenvironment. This may result in the extracellular release of a cytotoxic payload or drug, resulting in the killing of a variety of cells, via mechanisms such as cell death/cell-cycle arrest of tumor cells and/or stromal cells by bystander mechanism. In addition, further mechanisms include, but are not limited to disregulated angiogenesis or cytotoxic vascular targeting/collapse, vascular normalization, immunomodulation and induction of cellular differentiation and/or impediment of the epithelial to mesenchymal transition.

The Examples provided herein demonstrate the improved characteristics obtained during anti-EDB antibody and EDB ADC generation, such as allotype optimization to reduce immunogenicity, removal of COOH-terminal lysine to increase product homogeneity, and introduction of mutations to mitigate potential glycation liability and decrease heterogeneity (see Examples 1 and 2). Further, as shown in the Examples, EDB ADCs generated using various conventional and site-specific conjugation technologies (i.e. cysteines, lysines and/or acyl donor glutamine-containing ("Q") tags) and various linker-drug moieties demonstrate robust in vitro and in vivo efficacy (see Examples 6 to 8). Examples provided herein also showed that EDB ADCs generated using site-specific conjugation via engineered cysteine residues demonstrated improved characteristics compared to EDB ADCs generated using conventional conjugation via cysteine residues, such as improved pharmacokinetic (PK) profile (i.e. increased exposure and conjugation stability leading to less off-target toxic effects), favorable thermal stability and nonclinical safety profiled (i.e. alleviation of myelosuppression) (see Examples 9, 10 and 11, respectively). Further, the improved characteristic of the EDB ADCs generated with site-specific conjugation technologies may allow higher dosages in human treatment and thus provide increased efficacy. In some aspects, the EDB ADCs may comprise a substitution of the lysine (K) at position 290 (according to the EU index of Kabat) in the human IgG1 heavy chain constant region with a reactive cysteine (C) (K290C) and/or a substitution of the lysine (K) at position 183 (according to Kabat) in the human Kappa light chain constant region with a reactive cysteine (C) (κK183C) to enable site-specific conjugation.

Extra-Domain B of Fibronectin

As used herein "EDB+ FN" and "EDB" are used interchangeable and refer to fibronectin (FN) containing the extra-domain B (EDB). Further, "anti-EDB antibodies" and "anti-EDB+ FN antibodies" are used interchangeable and refer to antibodies that bind to EDB. "Anti-EDB antibody-drug conjugates", "EDB antibody-drug conjugates", "anti-EDB ADCs", "EDB ADCs" are used interchangeable and refer to ADCs comprising antibodies, or antigen-binding fragments thereof, that bind to EDB and are conjugated or linked to a drug. FN is a high-molecular-weight glycoprotein present in the extracellular matrix (ECM) and is involved in cell adhesion and migration processes including embryogenesis, wound healing, blood coagulation, host defense, and metastasis. FN typically exists as a dimer formed by two nearly identical ~250 kDa subunits covalently linked near their C-terminus by a pair of disulfide bonds. Each monomer consists of three types of repeating units: type I, type II and type III FN repeats. A single 75-kb gene encodes FN, however there are twenty protein variants observed in humans. Alternative splicing of the FN gene occurs in three regions resulting in the inclusion or exclusion of either one of the two type III repeats, called extra domain A (EDA) and extra domain B (EDB), and of a segment connecting two other type III repeats, called type III connecting segment (IIICS). EDB is a 91 amino acid sequence that is 100% identical in mice, rats, rabbits, dogs, cynomolgus monkey and humans. A representative EDB+ FN nucleotide sequence is provided under Accession No. NM_001306129.1 and corresponding amino acid sequence is provided under Accession No. NP_001293058.1. EDB and recombinant human 7-EDB-8-9 amino acid sequences are provided in Table 1. Recombinant human 7-EDB-8-9 comprises EDB flanked by domain 7 on the amino terminus and domain 8 and *domain* 9 at the carboxy terminus of EDB.

TABLE 1

EDB and 7-EDB-8-9 sequences

| SEQ ID NO. | Description | Sequence |
|---|---|---|
| 33 | EDB | EVPQLTDLSFVDITDSSIGLRWTPLNSSTIIGYRITVVAAGEGIPIFE DFVDSSVGYYTVTGLEPGIDYDISVITLINGGESAPTTLTQQT |
| 34 | Human FN-7-EDB-89-HIS protein | VVTQLSPPTNLHLEANPDTGVLAVSWERSTTPDITGYRITTTPTN GQQGNSLEEVVHADQSSCTFDNLSPGLEYNVSVYTVKDDKESV PISDTIIPEVPQLTDLSFVDITDSSIGLRWTPLNSSTIIGYRITVVAA GEGIPIFEDFVDSSVGYYTVTGLEPGIDYDISVITLINGGESAPTTL TQQT*AVPPPTDLRFTNIGPDTMRVTWAPPPSIDLTNFLVRYSPVK NEEDVAELSISPSDNAVVLTNLLPGTEYVVSVSSVYEQHESTPLR GRQKT*GLDSPTGIDFSDITANSFTVHWIAPRATITGYRIRHHPEHFSG RPREDRVPHSRNSITLTNLTPGTEYVVSIVALNGREESPLLIGRSRSHH HHHH |
| 35 | Cynomolgus FN-7-EDB-89-HIS protein | VVTPLSPPTNLHLETNPDTGVLTVSWERSTTPDITGYRITTTPTNG QQGYSLEEVVHADQSSCTFDNLSPGLEYNVSVYTVKDDKESVPI SDTIIPEVPQLTDLSFVDITDSSIGLRWTPLNSSTIIGYRITVVAAGE GIPIFEDFVDSSVGYYTVTGLEPGIDYDISVITLINGGESAPTTLTQ QT*AVPPPTDLRFTNIGPDTMRVTWAPPPSIDLTNFLVRYSPVKNE EDVAELSISPSDNAVVLTNLLPGTEYVVSVSSVYEQHESTPLRGR QKT*GLDSPTGIDFSDITANSFTVHWIAPRATITGYRIRHHPEHMSGR PREDRVPPSRNSITLTNLTPGTEYVVSIVALNGREESPLLIGRSRSHH HHH |

TABLE 1-continued

EDB and 7-EDB-8-9 sequences

| SEQ ID NO. | Description | Sequence |
|---|---|---|
| 36 | Rat FN-7-EDB-89-HIS protein | VVTPLSPPTNLHLEANPDTGVLTVSWERSTTPDITGYRITTTPTN GQQGTALEEVVHADQSSCTFENLNPGLEYNVSVYTVKDDKESA PISDTVIPEVPQLTDLSFVDITDSSIGLRWTPLNSSTIIGYRITVVAA GEGIPIFEDFVDSSVGYYTVTGLEPGIDYDISVITLINGGESAPTTL TQQT<u>AVPPPTDLRFTNIGPDTMRVTWAPPPSIELTNLLVRYSPVK</u> <u>NEEDVAELSISPSDNAVVLTNLLPGTEYLVSVSSVYEQHESIPLR</u> <u>GRQKT</u>GLDSPTGFDSSDVTANSFTVHWVAPRAPITGYIIRHHAEHSA GRPRQDRVPPSRNSITLTNLNPGTEYIVTIIAVNGREESPPLIGRSRSH HHHH |

Anti-EDB Antibodies

Antibodies of the present invention specifically bind to EDB. For preparation of ADCs of the invention, an antibody, or antigen-binding fragment thereof, may be any antibody (including antibodies described herein), or antigen-binding fragment thereof, that specifically binds to EDB. The antibody, or antigen-binding fragment thereof, may be isolated, purified, or derivatized for use in preparation of an EDB ADC.

As used herein, "antibody" or "Ab" refers to an immunoglobulin molecule capable of recognizing and binding to a specific target or antigen, such as a carbohydrate, polynucleotide, lipid, polypeptide, etc., through at least one antigen recognition site, located in the variable region of the immunoglobulin molecule. The term can encompass any type of antibody, including but not limited to monoclonal antibodies, polyclonal antibodies, "antigen-binding fragments" (or portion), such as Fab, Fab', F(ab')$_2$, Fd, Fv, Fc, etc., of intact antibodies that retain the ability to specifically bind to a given antigen (e.g. EDB), an isolated complementarity determining region (CDR), bispecific antibodies, heteroconjugate antibodies, mutants thereof, fusion proteins having an antibody, or antigen-binding fragment thereof, (e.g., a domain antibody), single chain (ScFv) and single domain antibodies (e.g., shark and camelid antibodies), maxibodies, minibodies, intrabodies, diabodies, triabodies, tetrabodies, v-NAR and bis-scFv (see, e.g., Holliger and Hudson, 2005, Nature Biotechnology 23(9): 1126-1136), humanized antibodies, chimeric antibodies and any other modified configuration of the immunoglobulin molecule that includes an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some aspects of the invention, the antibody, or antigen-binding fragment thereof, of the disclosed EDB ADCs is a chimeric, humanized, or a recombinant human antibody, or EDB-binding fragment thereof.

Native or naturally occurring antibodies and native immunoglobulins are typically heterotetrameric glycoproteins of about 150,000 daltons, composed of two identical light chains (LC) and two identical heavy chains (HC). Each heavy chain has a variable domain (VH) followed by a number of constant domains or regions (e.g. hinge, CH1, CH2 or CH3), referred to as "CH domains". Each light chain has a variable domain (VL) and a constant domain, referred to as "CL domain". The term "constant region" or "constant domain" of an antibody refers to the constant region of the antibody light chain or the constant region of the antibody heavy chain, either alone or in combination. The constant domains are not involved directly in binding an antibody to an antigen, but exhibit various effector functions, such as Fc receptor (FcR) binding, participation of the antibody in antibody-dependent cellular toxicity (ADCC), opsonization, initiation of complement dependent cytotoxicity, and mast cell degranulation. The constant regions of the EDB antibodies may be derived from constant regions of any one of IgA, IgD, IgE, IgG, IgM, any isotypes thereof (e.g., IgG1, IgG2, IgG3, or IgG4 isotypes of IgG), as well as subclasses and mutated versions thereof.

CH1 domain includes the first (most amino terminal) constant region domain of an immunoglobulin heavy chain that extends, e.g. from about positions 118-215 according to the EU index of Kabat. The CH1 domain is adjacent to the VH domain and amino terminal to the hinge region of an immunoglobulin heavy chain molecule, and does not form a part of the Fc region of an immunoglobulin heavy chain.

The hinge region includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains.

CH2 domain includes the portion of a heavy chain immunoglobulin molecule that extends, e.g. from about positions 231-340 according to the EU index of Kabat. The CH2 domain is unique in that it is not closely paired with another domain. Rather, two N-linked branched carbohydrate chains are interposed between the two CH2 domains of an intact native IgG molecule. In some aspects, the antibody (or fragment thereof) of the invention comprises a CH2 domain derived from an IgG molecule, such as IgG1, IgG2, IgG3, or IgG4. In some aspects, the IgG is a human IgG.

CH3 domain includes the portion of a heavy chain immunoglobulin molecule that extends approximately 110 residues from N-terminus of the CH2 domain, e.g. from about positions 341-447 according to the EU index of Kabat. The CH3 domain typically forms the C-terminal portion of the antibody. In some immunoglobulins, however, additional domains may extend from CH3 domain to form the C-terminal portion of the molecule (e.g. the CH4 domain in the μ chain of IgM and the ε chain of IgE). In some aspects, the antibody (or fragment thereof) of the invention comprises a CH3 domain derived from an IgG molecule, such as IgG1, IgG2, IgG3, or IgG4. In some aspects, the IgG is a human IgG.

CL domain includes the constant region domain of an immunoglobulin light chain that extends, e.g. from about positions 108-214 according to the EU index of Kabat. The CL domain is adjacent to the VL domain. In some aspects, the antibody (or fragment thereof) of the invention comprises a kappa light chain constant domain (CLI). In some aspects, the antibody (or fragment thereof) comprises a lambda light chain constant domain (CLλ). CLκ has known polymorphic loci CLκ-V/A45 and CLκ-L/V83 (using Kabat numbering) thus allowing for polymorphisms Km(1): CLκ-V45/L83; Km(1,2): CLκ-A45/L83; and Km(3): CLκ-A45/V83.

Polypeptides, antibodies and ADCs of the invention may have antibody components with any of these light chain constant regions.

The Fc region generally comprises a CH2 domain and a CH3 domain. Although the boundaries of the Fc region of an immunoglobulin heavy chain might vary, the human IgG heavy chain Fc region is usually defined to stretch from an amino acid residue at position Cys226, or from Pro230 (according to the EU index of Kabat), to the carboxyl-terminus thereof. A Fc region may be a native sequence Fc region or a variant Fc region. (Kabat et al., Sequences of Proteins of Immunological Interest, 5th Ed. Public Health Service, National Institutes of Health, Bethesda, Md., 1991).

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies.

A CDR of a variable domain may be identified in accordance with the definitions of the Kabat (Kabat et al., 1992, Sequences of Proteins of Immunological Interest, 5th ed., Public Health Service, NIH, Washington D.C), Chothia (Chothia et al., Nature 342:877-883, (1989)), the accumulation of both Kabat and Chothia, AbM definition (derived using Oxford Molecular's AbM antibody modeling software, now ACCELRYS®), contact definition (based on observed antigen contacts, set forth in MacCallum et al., J. Mol. Biol., 262:732-745, (1996)), and/or conformational definition (Makabe et al., Journal of Biological Chemistry, 283:1156-1166, 2008) or any method of CDR determination well known in the art. As used herein, a CDR may refer to CDRs defined by any approach known in the art, including combinations of approaches. For the present invention, the CDRs set forth in Table 2 below were derived using Kabat and Chothia definitions. The anti-EDB antibodies, or antigen-binding fragment thereof, of the present invention include one or more CDR(s) (such as one, two, three, four, five, or all six CDRs).

An antibody, an ADC, or a polypeptide that "specifically binds" or "preferentially binds" (used interchangeably herein) to a target or antigen (e.g., EDB protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target or antigen if it binds with greater affinity, avidity, more readily, and/or with greater duration than it binds to other substances. For example, an antibody that specifically or preferentially binds to an EDB epitope is an antibody that binds this epitope with greater affinity, avidity, more readily, and/or with greater duration than it binds to other EDB epitopes or non-EDB epitopes.

The term "binding affinity" or "$K_D$" as used herein, is intended to refer to the equilibrium dissociation constant of a particular antigen-antibody interaction. The $K_D$ is the ratio of the rate of dissociation, also called the "off-rate" or "$k_d$", to the rate of association, or "on-rate" or "$k_a$". Thus, $K_D$ equals $k_d/k_a$ and is expressed as a molar concentration (M). It follows that the smaller the $K_D$, the stronger the binding affinity. Therefore, a $K_D$ of 1 μM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a BIACORE® (Cytiva; surface plasmon resonance (SPR) system). Other standard assays to evaluate the binding ability of ligands such as antibodies towards targets are known in the art, including for example, ELISAs, Western blots, RIAs, and flow cytometry analysis.

An "isolated antibody", as used herein, refers to an antibody that is substantially free of other antibodies having different antigenic specificities (e.g., an isolated antibody that specifically binds EDB is substantially free of antibodies that specifically bind antigens other than EDB). Moreover, an isolated antibody may be substantially free of other cellular material and/or chemicals. It is also understood that by reading this definition, for example, an antibody (or moiety or epitope) that specifically or preferentially binds to a first target may or may not specifically or preferentially bind to a second target.

In some aspects of the invention, an EDB ADC includes an antibody that competes for binding to human EDB with, and/or binds the same epitope as, an antibody, or antigen-binding fragment thereof, described herein.

The term "compete", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The "L19" antibody, herein also referenced as "EDB-L19" antibody, is a human antibody that binds EDB. The L19 antibody is disclosed and characterized in PCT International Publication Nos. WO1997/045544, WO1999/

058570 and WO2001/062800, which are incorporated herein by reference in their entirety, and the L19-EDB sequences are provided herein in Table 2 (SEQ ID NOs. 1-16).

In some aspects of the invention, antibodies used to prepare EDB ADCs may be monoclonal antibodies. The term "monoclonal antibody" or "mAb" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

In some aspects of the invention, antibodies used to prepare ADCs of the invention may be monovalent, i.e., having one antigen binding site per molecule (e.g., IgG or Fab). In some instances, a monovalent antibody can have more than one antigen binding sites, but the binding sites are from different antigens. In some aspects of the invention, the antibody, or antigen-binding fragment thereof, of an ADC of the invention may include a "bivalent antibody", i.e., having two antigen binding sites per molecule (e.g., IgG). In some instances, the two binding sites have the same antigen specificities. Alternatively, bivalent antibodies may be bispecific. A "bispecific," "dual-specific" or "bifunctional" antibody is a hybrid antibody having two different antigen binding sites. The two antigen binding sites of a bispecific antibody bind to two different epitopes, which may reside on the same or different protein targets.

The term "chimeric antibody" is intended to refer to antibodies in which part or all of the variable region sequences are derived from one species and the constant region sequences are derived from another species, such as an antibody in which the variable region sequences are derived from a mouse antibody and the constant region sequences are derived from a human antibody.

As used herein, "humanized" or "CDR grafted" antibody refers to forms of non-human (e.g. murine) antibodies that are chimeric immunoglobulins, immunoglobulin chains, or fragments thereof (such as Fv, Fab, Fab', F(ab)$_2$ or other antigen binding subsequences of antibodies) that contain minimal sequence derived from a non-human immunoglobulin. Preferably, humanized antibodies are human immunoglobulins (recipient antibody) in which residues from one or more CDRs of the recipient are replaced by residues from one or more CDRs of a non-human species (donor antibody) such as mouse, rat, or rabbit having the desired specificity, affinity, and capacity.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)). Additional guidance may be found in Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003).

Nucleic acids encoding the heavy and light chains of the antibodies used to prepare the ADCs of the invention can be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329:112-124, 2008; U.S. Pat. No. 7,314,622.

As used herein, the term "vector" refers to a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, "polynucleotide," "nucleic acid/nucleotide," and "oligonucleotide" are used interchangeably herein, and include polymeric forms of nucleotides of any length, either deoxyribonucleotides or ribonucleotides, analogs thereof, or any substrate that can be incorporated into a chain by DNA or RNA polymerase. Polynucleotides may have any three-dimensional structure, and may perform any function, known or unknown. Polynucleotides may be naturally-occurring, synthetic, recombinant or any combination thereof.

For all heavy chain constant region amino acid positions discussed in the present invention, numbering is according to the Eu index first described in Edelman et al., 1969, Proc. Natl. Acad. Sci. USA 63(1):78-85, describing the amino acid sequence of myeloma protein Eu, which is the first human 1gG1 sequenced. The Eu index of Edelman et al. is also set forth in Kabat et al., 1991, Sequences of Proteins of Immunological Interest, 5th Ed., United States Public Health Service, National Institutes of Health, Bethesda. Thus, the "EU index as set forth in Kabat" or "EU index of Kabat" refers to the residue numbering system based on the human 1gG1 Eu antibody of Edelman et al. as set forth in Kabat 1991.

The numbering system used for the light chain constant region amino acid sequence is that set forth in Kabat 1991.

The EDB ADCs of the present invention may be conjugated to the drug/payload using conventional cysteine technology or site-specific conjugation technology. To accommodate site-specific conjugation via engineered cysteines, the constant domain may be modified to provide for a reactive cysteine residue engineered at one or more specific sites (sometimes referred to as "Cys" mutants). To accommodate site-specific conjugation via transglutaminase-based conjugation, an acyl donor glutamine-containing ("Q") tag or an endogenous glutamine is made reactive by polypeptide engineering in the presence of transglutaminase and an amine.

The present invention provides for optimization of the L19-EDB antibody by generation of a non-immunogenic antibody. In some aspects, the L19-EDB human IgG1 constant region comprising a Glm(a) allotype having aspartic acid (D) at position 356 and leucine (L) at position 358, may be substituted with a non-Glm(a) allotype having glutamic acid (E) at position 356 and methionine (M) at position 358 (according to the numbering of the EU index of Kabat).

Further, to reduce potential chemical liabilities and antigen binding a putative protein glycation site, anti-EDB antibodies of the present invention may have a heavy chain variable region comprising a mutation of the lysine (K) at position 94 (according to the numbering of the EU index of Kaba) to an arginine (R), e.g. (K94R).

For site-specific conjugation via engineered cysteines, the anti-EDB antibody heavy chain constant domain may comprise a reactive engineered cysteine residue at position 290 (K290C), according to the numbering of the EU index of Kabat. Additional cysteine substitutions may be introduced. In another aspect, the anti-EDB antibody light chain constant domain may comprise a reactive engineered cysteine residue at position 183 (κK183C), according to the numbering of Kabat. Additional cysteine substitutions may be introduced.

For site-specific conjugation via engineered glutamine residues, the anti-EDB antibody heavy chain constant domain may comprise an engineered H16-glutamine-containing tag LLQG (SEQ ID NO: 40). Further, to optimize this site-specific conjugation the lysine (K) amino acid at position 222 (according to the EU index of Kabat) on the heavy chain may be substituted with an arginine (R), e.g. (K222R).

Amino acid modifications can be made by any method known in the art and many such methods are well known and routine for the skilled artisan, e.g. mutations, substitutions, deletions, and/or additions. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, PNAS 82:488).

In some aspects of the invention, the EDB ADCs include an antibody, or antigen binding fragment thereof, having a heavy chain and/or a light chain comprising an amino acid sequence that is at least 90%, 95%, 98%, or 99% identical to any of the heavy or light chains disclosed herein. Residues that have been altered can be in the variable region or in the constant region of the antibody. In some aspects, there are no more than 1, 2, 3, 4 or 5 residues that have been altered as compared to any of the heavy or light chains disclosed herein.

The term "percent identical" in the context of amino acid sequences means the number of residues in two sequences that are the same when aligned for maximum correspondence. There are a number of different algorithms known in the art which can be used to measure amino acid percent identity (i.e., the Basic Local Alignment Tool or BLAST®). Unless otherwise specified, default parameters for a particular program or algorithm are used.

For use in preparation of EDB ADCs, antibodies described herein may be substantially pure, i.e., at least 50% pure (i.e., free from contaminants), more preferably, at least 90% pure, more preferably, at least 95% pure, yet more preferably, at least 98% pure, and most preferably, at least 99% pure.

Tables 2 and 3 provide the amino acid (protein) sequences and associated nucleic acid (DNA) sequences of anti-EDB antibodies of the present invention. The CDRs are as defined by Kabat and Chothia. The shaded residues identify amino acid mutations, substitutions and/or insertions relating to antibody optimization and underlined residues identify amino acid mutations, substitutions and/or insertions relating to site-specific conjugation technology.

TABLE 2

Anti-EDB antibody sequences

| SEQ ID NO. | Description | Sequence |
|---|---|---|
| 1 | EDB-L19 VH Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCAKPFPYFDYWGQGTLVTVSS |
| 2 | EDB-L19 VH DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGCACAGGCCGTATATTACTGT GCGAAACCGTTTCCGTATTTTGACTACGGGGCCAGGGAAC CCTGGTCACCGTCTCGAGT |
| 3 | EDB L19 VH CDR1 Kabat | SFSMS |
| 4 | EDB-L19 VH CDR1 Chothia | GFTFSSF |

TABLE 2-continued

Anti-EDB antibody sequences

| SEQ ID NO. | Description | Sequence |
|---|---|---|
| 5 | EDB-L19 VH CDR2 Kabat | SISGSSGTTYYADSVKG |
| 6 | EDB-L19 VH CDR2 Chothia | SGSSGT |
| 7 | EDB-L19 VH CDR3 Kabat/Chothia | PFPYFDY |
| 8 | EDB-L19 HC Human IgG1 Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCAKPFPYFDYWGQGTLVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKKV EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVM HEALHNHYTQKSLSLSPGK |
| 9 | EDB-L19 HC DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGACACGGCCGTATATTACTGT GCGAAACCGTTTCCGTATTTTGACTACTGGGGCCAGGGAAC CCTGGTCACCGTCTCGAGTGCGTCGACCAAGGGCCCATCGG TCTTCCCCCTGGCACCCTCCTCCAAGAGCACCTCTGGGGGC ACAGCGGCCCTGGGCTGCCTGGTCAAGGACTACTTCCCCGA ACCGGTGACGGTGTCGTGGAACTCAGGCGCCCTGACCAGCG GCGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCAG CAACACCAAGGTGGACAAGAAAGTTGAGCCCAAATCTTGTG ACAAAACTCACACATGCCCACCGTGCCCAGCACCTGAACTC CTGGGGGGACCGTCAGTCTTCCTCTTCCCCCCAAAACCCAA GGACACCCTCATGATCTCCCGGACCCCTGAGGTCACATGCG TGGTGGTGGACGTGAGCCACGAAGACCCTGAGGTCAAGTTC AACTGGTACGTGGACGGCGTGGAGGTGCATAATGCCAAGA CAAAGCCGCGGGAGGAGCAGTACAACAGCACGTACCGTGT GGTCAGCGTCCTCACCGTCCTGCACCAGGACTGGCTGAATG GCAAGGAGTACAAGTGCAAGGTCTCCAACAAAGCCCTCCCA GCCCCCATCGAGAAAACCATCTCCAAAGCCAAAGGGCAGC CCCGAGAACCACAGGTGTACACCCTGCCCCCATCCCGGGAT GAGCTGACCAAGAACCAGGTCAGCCTGACCTGCCTGGTCAA AGGCTTCTATCCCAGCGACATCGCCGTGGAGTGGGAGAGCA ATGGGCAGCCGGAGAACAACTACAAGACCACGCCTCCCGT GCTGGACTCCGACGGCTCCTTCTTCCTCTACAGCAAGCTCAC CGTGGACAAGAGCAGGTGGCAGCAGGGGAACGTCTTCTCAT GCTCCGTGATGCATGAGGCTCTGCACAACCACTACACGCAG AAGAGCCTCTCCCTGTCTCCGGGTAAA |
| 10 | EDB-L19 VL Protein | EIVLTQSPGTLSLSPGERATLSCRASQSVSSSFLAWYQQKPGQA PRLLIYYASSRATGIPDRFSGSGSGTDFTLTISRLEPEDFAVYYC QQTGRIPPTFGQGTKVEIK |
| 11 | EDB-L19 VL DNA | GAAATTGTGTTAACGCAGTCTCCAGGCACCCTGTCTTTGTCT CCAGGGGAAAGAGCCACCCTCTCCTGCAGGGCCAGTCAGA GTGTTAGCAGCAGCTTTTTAGCCTGGTACCAGCAGAAACCT GGCCAGGCTCCCAGGCTCCTCATCTATTATGCATCCAGCAG GGCCACTGGCATCCCAGACAGGTTCAGTGGCAGTGGGTCTG GGACAGACTTCACTCTCACCATCAGCAGACTGGAGCCTGAA GATTTTGCAGTGTATTACTGTCAGCAGACGGGTCGTATTCCG CCGACGTTCGGCCAAGGGACCAAGGTGGAAATCAAA |
| 12 | EDB-L19 VL CDR1 Kabat/Chothia | RASQSVSSSFLA |

TABLE 2-continued

Anti-EDB antibody sequences

| SEQ ID NO. | Description | Sequence |
|---|---|---|
| 13 | EDB-L19 VL CDR2 Kabat/Chothia | YASSRAT |
| 14 | EDB-L19 VL CDR3 Kabat/Chothia | QQTGRIPPT |
| 15 | EDB-L19 LC Human Kappa Protein | EIVLTQSPGTLSLSPGERATLSCRASQSVSSSFLAWYQQKPGQAPRLLIYYASSRATGIPDRFSGSGSGTDFTLTISRLEPEDFAVYYCQQTGRIPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 16 | EDB-L19 LC DNA | GAAATTGTGTTAACGCAGTCTCCAGGCACCCTGTCTTTGTCTCCAGGGGAAAGAGCCACCCTCTCCTGCAGGGCCAGTCAGAGTGTTAGCAGCAGCTTTTTAGCCTGGTACCAGCAGAAACCTGGCCAGGCTCCCAGGCTCCTCATCTATTATGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGACGGGTCGTATTCCGCCGACGTTCGGCCAAGGGACCAAGGTGGAAATCAAACGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |
| 17 | EDB-PFE HC Protein | EVQLLESGGGLVQPGGSLRLSCAASGFTFSSFSMSWVRQAPGKGLEWVSSISGSSGTTYYADSVKGRFTISRDNSKNTLYLQMNSLRAEDTAVYYCAKPFPYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 18 | EDB-PFE HC DNA | GAGGTGCAGCTGTTGGAGTCTGGGGGAGGCTTGGTACAGCCTGGGGGGTCCCTGAGACTCTCCTGTGCAGCCTCTGGATTCACCTTTAGCAGTTTTTCGATGAGCTGGGTCCGCCAGGCTCCAGGGAAGGGGCTGGAGTGGGTCTCATCTATTAGTGGTAGTTCGGGTACCACATACTACGCAGACTCCGTGAAGGGCCGGTTCACCATCTCCAGAGACAATTCCAAGAACACGCTGTATCTGCAAATGAACAGCCTGAGAGCCGAAGACACGGCCGTATATTACTGTGCGAAACCGTTTCCGTATTTTGACTACTGGGGCCAGGGAACCCTGGTCACCGTCTCGAGTGCGTCGACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCAC |

TABLE 2-continued

Anti-EDB antibody sequences

| SEQ ID NO. | Description | Sequence |
|---|---|---|
| | | CGTGGACAAGAGCAGGTGGCAGCAGGGGAACGTCTTCTCAT GCTCCGTGATGCATGAGGCTCTGCACAACCACTACACGCAG AAGAGCCTCTCCCTGTCCCCGGGT |
| 19 | EDB-(K290C) HC Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCAKPFPYFDYWGQGTLVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKKV EPKSCDKTHTCPPCPAPELLGGPSVFLFPPKPKDTLMISRTPEVT CVVVDVSHEDPEVKFNWYVDGVEVHNAKTCPREEQYNSTYR VVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVM HEALHNHYTQKSLSLSPG |
| 20 | EDB-(K290C) HC DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGACACGGCCGTATATTACTGT GCGAAACCGTTTCCGTATTTTGACTACTGGGGCCAGGGAAC CCTGGTCACCGTCTCGAGTGCGTCGACCAAGGGCCCATCGG TCTTCCCCCTGGCACCCTCCTCCAAGAGCACCTCTGGGGGC ACAGCGGCCCTGGGCTGCCTGGTCAAGGACTACTTCCCCGA ACCGGTGACGGTGTCGTGGAACTCAGGCGCCCTGACCAGCG GCGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCAG CAACACCAAGGTGGACAAGAAAGTTGAGCCCAAATCTTGTG ACAAAACTCACACATGCCCACCGTGCCCAGCACCTGAACTC CTGGGGGGACCGTCAGTCTTCCTCTTCCCCCCAAAACCCAA GGACACCCTCATGATCTCCCGGACCCCTGAGGTCACATGCG TGGTGGTGGACGTGAGCCACGAAGACCCTGAGGTCAAGTTC AACTGGTACGTGGACGGCGTGGAGGTGCATAATGCCAAGA CATGCCCGCGGGAGGAGCAGTACAACAGCACGTACCGTGT GGTCAGCGTCCTCACCGTCCTGCACCAGGACTGGCTGAATG GCAAGGAGTACAAGTGCAAGGTCTCCAACAAAGCCCTCCCA GCCCCCATCGAGAAAACCATCTCCAAAGCCAAAGGGCAGC CCCGAGAACCACAGGTGTACACCCTGCCCCCATCCCGGGAG GAGATGACCAAGAACCAGGTCAGCCTGACCTGCCTGGTCAA AGGCTTCTATCCCAGCGACATCGCCGTGGAGTGGGAGAGCA ATGGGCAGCCGGAGAACAACTACAAGACCACGCCTCCCGT GCTGGACTCCGACGGCTCCTTCTTCCTCTATAGCAAGCTCAC CGTGGACAAGAGCAGGTGGCAGCAGGGGAACGTCTTCTCAT GCTCCGTGATGCATGAGGCTCTGCACAACCACTACACGCAG AAGAGCCTCTCCCTGTCCCCGGGT |
| 21 | EDB-(K94R) VH Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCARPFPYFDYWGQGTLVTVSS |
| 22 | EDB-(K94R) VH DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGACACGGCCGTATATTACTGT GCGAGACCGTTTCCGTATTTTGACTACTGGGGCCAGGGAAC CCTGGTCACCGTCTCGAGT |

TABLE 2-continued

Anti-EDB antibody sequences

| SEQ ID NO. | Description | Sequence |
|---|---|---|
| 23 | EDB-(K94R) HC Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCARPFPYFDYWGQGTLVTVSSASTKGPSVFPLAP SSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQPR EPQVYTLPPSREEMTKNQVSLTCLVKGFYPSDIAVEWESNGQP ENNYKTTPPVLDSDGSFFLYSKLTVDKSRWQQGNVFSCSVMH EALHNHYTQKSLSLSPG |
| 24 | EDB-(K94R) HC DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGACACGGCCGTATATTACTGT GCGAGACCGTTTCCGTATTTTGACTACTGGGGCCAGGGAAC CCTGGTCACCGTCTCGAGTGCGTCGACCAAGGGCCCATCGG TCTTCCCCCTGGCACCCTCCTCCAAGAGCACCTCTGGGGGC ACAGCGGCCCTGGGCTGCCTGGTCAAGGACTACTTCCCCGA ACCGGTGACGGTGTCGTGGAACTCAGGCGCCCTGACCAGCG GCGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCAG CAACACCAAGGTGGACAAGAAAGTTGAGCCCAAATCTTGTG ACAAAACTCACACATGCCCACCGTGCCCAGCACCTGAACTC CTGGGGGGACCGTCAGTCTTCCTCTTCCCCCCAAAACCCAA GGACACCCTCATGATCTCCCGGACCCCTGAGGTCACATGCG TGGTGGTGGACGTGAGCCACGAAGACCCTGAGGTCAAGTTC AACTGGTACGTGGACGGCGTGGAGGTGCATAATGCCAAGA CAAAGCCGCGGGAGGAGCAGTACAACAGCACGTACCGTGT GGTCAGCGTCCTCACCGTCCTGCACCAGGACTGGCTGAATG GCAAGGAGTACAAGTGCAAGGTCTCCAACAAAGCCCTCCCA GCCCCCATCGAGAAAACCATCTCCAAAGCCAAAGGGCAGC CCCGAGAACCACAGGTGTACACCCTGCCCCCATCCCGGGAG GAGATGACCAAGAACCAGGTCAGCCTGACCTGCCTGGTCAA AGGCTTCTATCCCAGCGACATCGCCGTGGAGTGGGAGAGCA ATGGGCAGCCGGAGAACAACTACAAGACCACGCCTCCCGT GCTGGACTCCGACGGCTCCTTCTTCCTCTATAGCAAGCTCAC CGTGGACAAGAGCAGGTGGCAGCAGGGGAACGTCTTCTCAT GCTCCGTGATGCATGAGGCTCTGCACAACCACTACACGCAG AAGAGCCTCTCCCTGTCCCCGGGT |
| 25 | EDB-(K94R-K290C) HC Protein | EVQLLESGGGLVQPGGSLRLSCAASGFTFSSFSMSWVRQAPGK GLEWVSSISGSSGTTYYADSVKGRFTISRDNSKNTLYLQMNSL RAEDTAVYYCARPFPYFDYWGQGTLVTVSSASTKGPSVFPLAP SSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTCPPCPAPELLGGPSVFLFPPKPKDTLMISRTPEVTC VVVDVSHEDPEVKFNWYVDGVEVHNAKTCPREEQYNSTYRV VSVLTVLHQDWLNGKEYKCKVSNKALPAPIEKTISKAKGQPR EPQVYTLPPSREEMTKNQVSLTCLVKGFYPSDIAVEWESNGQP ENNYKTTPPVLDSDGSFFLYSKLTVDKSRWQQGNVFSCSVMH EALHNHYTQKSLSLSPG |
| 26 | EDB-(K94R-K290C) HC DNA | GAGGTGCAGCTGTTGGAGTCTGGGGGAGGCTTGGTACAGCC TGGGGGGTCCCTGAGACTCTCCTGTGCAGCCTCTGGATTCA CCTTTAGCAGTTTTTCGATGAGCTGGGTCCGCCAGGCTCCAG GGAAGGGGCTGGAGTGGGTCTCATCTATTAGTGGTAGTTCG GGTACCACATACTACGCAGACTCCGTGAAGGGCCGGTTCAC CATCTCCAGAGACAATTCCAAGAACACGCTGTATCTGCAAA TGAACAGCCTGAGAGCCGAAGACACGGCCGTATATTACTGT GCGAGACCGTTTCCGTATTTTGACTACTGGGGCCAGGGAAC CCTGGTCACCGTCTCGAGTGCGTCGACCAAGGGCCCATCGG TCTTCCCCCTGGCACCCTCCTCCAAGAGCACCTCTGGGGGC ACAGCGGCCCTGGGCTGCCTGGTCAAGGACTACTTCCCCGA ACCGGTGACGGTGTCGTGGAACTCAGGCGCCCTGACCAGCG GCGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCAG CAACACCAAGGTGGACAAGAAAGTTGAGCCCAAATCTTGTG |

TABLE 2-continued

Anti-EDB antibody sequences

| SEQ ID NO. | Description | Sequence |
|---|---|---|
| | | ACAAAACTCACACATGCCCACCGTGCCCAGCACCTGAACTC<br>CTGGGGGGACCGTCAGTCTTCCTCTTCCCCCCAAAACCCAA<br>GGACACCCTCATGATCTCCCGGACCCCTGAGGTCACATGCG<br>TGGTGGTGGACGTGAGCCACGAAGACCCTGAGGTCAAGTTC<br>AACTGGTACGTGGACGGCGTGGAGGTGCATAATGCCAAGA<br>CATGCCCGCGGGAGGAGCAGTACAACAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCCA<br>GCCCCCATCGAGAAAACCATCTCCAAAGCCAAAGGGCAGC<br>CCCGAGAACCACAGGTGTACACCCTGCCCCCATCCCGGGAG<br>GAGATGACCAAGAACCAGGTCAGCCTGACCTGCCTGGTCAA<br>AGGCTTCTATCCCAGCGACATCGCCGTGGAGTGGGAGAGCA<br>ATGGGCAGCCGGAGAACAACTACAAGACCACGCCTCCCGT<br>GCTGGACTCCGACGGCTCCTTCTTCCTCTATAGCAAGCTCAC<br>CGTGGACAAGAGCAGGTGGCAGCAGGGGAACGTCTTCTCAT<br>GCTCCGTGATGCATGAGGCTCTGCACAACCACTACACGCAG<br>AAGAGCCTCTCCCTGTCCCCCGGA |
| 27 | EDB-(H16-K222R) HC Protein | EVQLLESGGGLVQPGGSLRLSCAASGFTFSSFSMSWVRQAPGK<br>GLEWVSSISGSSGTTYYADSVKGRFTISRDNSKNTLYLQMNSL<br>RAEDTAVYYCAKPFPYFDYWGQGTLVTVSSASTKGPSVFPLA<br>PSSKSTSGGTAALGCLVKDYFPEPVTVSWNSGALTSGVHTFPA<br>VLQSSGLYSLSSVVTVPSSSLGTQTYICNVNHKPSNTKVDKKV<br>EPKSCDRTHTCPPCPAPELLGGPSVFLFPPKPKDTLMISRTPEVT<br>CVVVDVSHEDPEVKFNWYVDGVEVHNAKTKPRELLQGSTYR<br>VVSVLTVLHQDWLNGKEYKCKVSNKALPAPIEKTISKAKGQP<br>REPQVYTLPPSREEMTKNQVSLTCLVKGFYPSDIAVEWESNGQ<br>PENNYKTTPPVLDSDGSFFLYSKLTVDKSRWQQGNVFSCSVM<br>HEALHNHYTQKSLSLSPG |
| 28 | EDB-(H16-K222R) HC DNA | GAGGTGCAGCTGTTGGAGTCTGGGGGAGGCTTGGTACAGCC<br>TGGGGGGTCCCTGAGACTCTCCTGTGCAGCCTCTGGATTCA<br>CCTTTAGCAGTTTTTCGATGAGCTGGGTCCGCCAGGCTCCAG<br>GGAAGGGGCTGGAGTGGGTCTCATCTATTAGTGGTAGTTCG<br>GGTACCACATACTACGCAGACTCCGTGAAGGGCCGGTTCAC<br>CATCTCCAGAGACAATTCCAAGAACACGCTGTATCTGCAAA<br>TGAACAGCCTGAGAGCCGAAGACACGGCCGTATATTACTGT<br>GCGAAACCGTTTCCGTATTTTGACTACTGGGGCCAGGGAAC<br>CCTGGTCACCGTCTCGAGTGCGTCGACCAAGGGCCCATCGG<br>TCTTCCCCCTGGCACCCTCCTCCAAGAGCACCTCTGGGGGC<br>ACAGCGGCCCTGGGCTGCCTGGTCAAGGACTACTTCCCCGA<br>ACCGGTGACGGTGTCGTGGAACTCAGGCGCCCTGACCAGCG<br>GCGTGCACACCTTCCCGGCTGTCCTACAGTCCTCAGGACTCT<br>ACTCCCTCAGCAGCGTAGTGACCGTGCCCTCCAGCAGCTTG<br>GGCACCCAGACCTACATCTGCAACGTGAATCACAAGCCCAG<br>CAACACCAAGGTGGACAAGAAAGTTGAGCCCAAATCTTGTG<br>ACCGCACTCACACATGCCCACCGTGCCCAGCACCTGAACTC<br>CTGGGGGGACCGTCAGTCTTCCTCTTCCCCCCAAAACCCAA<br>GGACACCCTCATGATCTCCCGGACCCCTGAGGTCACATGCG<br>TGGTGGTGGACGTGAGCCACGAAGACCCTGAGGTCAAGTTC<br>AACTGGTACGTGGACGGCGTGGAGGTGCATAATGCCAAGA<br>CAAAGCCGCGGGAGCTGCTGCAGGGGAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCCA<br>GCCCCCATCGAGAAAACCATCTCCAAAGCCAAAGGGCAGC<br>CCCGAGAACCACAGGTGTACACCCTGCCCCCATCCCGGGAG<br>GAGATGACCAAGAACCAGGTCAGCCTGACCTGCCTGGTCAA<br>AGGCTTCTATCCCAGCGACATCGCCGTGGAGTGGGAGAGCA<br>ATGGGCAGCCGGAGAACAACTACAAGACCACGCCTCCCGT<br>GCTGGACTCCGACGGCTCCTTCTTCCTCTATAGCAAGCTCAC<br>CGTGGACAAGAGCAGGTGGCAGCAGGGGAACGTCTTCTCAT<br>GCTCCGTGATGCATGAGGCTCTGCACAACCACTACACGCAG<br>AAGAGCCTCTCCCTGTCTCCGGGT |

TABLE 2-continued

Anti-EDB antibody sequences

| SEQ ID NO. | Description | Sequence |
|---|---|---|
| 29 | EDB-(K94R-H16-K222R) HC Protein | EVQLLESGGGLVQPGGSLRLSCAASGFTFSSFSMSWVRQAPGK<br>GLEWVSSISGSSGTTYYADSVKGRFTISRDNSKNTLYLQMNSL<br>RAEDTAVYYCARPFPYFDYWGQGTLVTVSSASTKGPSVFPLAP<br>SSKSTSGGTAALGCLVKDYFPEPVTVSWNSGALTSGVHTFPAV<br>LQSSGLYSLSSVVTVPSSSLGTQTYICNVNHKPSNTKVDKKVEP<br>KSCDRTHTCPPCPAPELLGGPSVFLFPPKPKDTLMISRTPEVTC<br>VVVDVSHEDPEVKFNWYVDGVEVHNAKTKPRELLQGSTYRV<br>VSVLTVLHQDWLNGKEYKCKVSNKALPAPIEKTISKAKGQPR<br>EPQVYTLPPSREEMTKNQVSLTCLVKGFYPSDIAVEWESNGQP<br>ENNYKTTPPVLDSDGSFFLYSKLTVDKSRWQQGNVFSCSVMH<br>EALHNHYTQKSLSLSPG |
| 30 | EDB-(K94R-H16-K222R) HC DNA | GAGGTGCAGCTGTTGGAGTCTGGGGGAGGCTTGGTACAGCC<br>TGGGGGGTCCCTGAGACTCTCCTGTGCAGCCTCTGGATTCA<br>CCTTTAGCAGTTTTTCGATGAGCTGGGTCCGCCAGGCTCCAG<br>GGAAGGGGCTGGAGTGGGTCTCATCTATTAGTGGTAGTTCG<br>GGTACCACATACTACGCAGACTCCGTGAAGGGCCGGTTCAC<br>CATCTCCAGAGACAATTCCAAGAACACGCTGTATCTGCAAA<br>TGAACAGCCTGAGAGCCGAAGACACGGCCGTATATTACTGT<br>GCGAGACCGTTTCCGTATTTTGACTACTGGGGCCAGGGAAC<br>CCTGGTCACCGTCTCGAGTGCGTCGACCAAGGGCCCATCGG<br>TCTTCCCCCTGGCACCCTCCTCCAAGAGCACCTCTGGGGGC<br>ACAGCGGCCCTGGGCTGCCTGGTCAAGGACTACTTCCCCGA<br>ACCGGTGACGGTGTCGTGGAACTCAGGCGCCCTGACCAGCG<br>GCGTGCACACCTTCCCGGCTGTCCTACAGTCCTCAGGACTCT<br>ACTCCCTCAGCAGCGTAGTGACCGTGCCCTCCAGCAGCTTG<br>GGCACCCAGACCTACATCTGCAACGTGAATCACAAGCCCAG<br>CAACACCAAGGTGGACAAGAAAGTTGAGCCCAAATCTTGTG<br>ACCGCACTCACACATGCCCACCGTGCCCAGCACCTGAACTC<br>CTGGGGGGACCGTCAGTCTTCCTCTTCCCCCCAAAACCCAA<br>GGACACCCTCATGATCTCCCGGACCCCTGAGGTCACATGCG<br>TGGTGGTGGACGTGAGCCACGAAGACCCTGAGGTCAAGTTC<br>AACTGGTACGTGGACGGCGTGGAGGTGCATAATGCCAAGA<br>CAAAGCCGCGGGAGCTGCTGCAGGGGAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCCA<br>GCCCCCATCGAGAAAACCATCTCCAAAGCCAAAGGGCAGC<br>CCCGAGAACCACAGGTGTACACCCTGCCCCCATCCCGGGAG<br>GAGATGACCAAGAACCAGGTCAGCCTGACCTGCCTGGTCAA<br>AGGCTTCTATCCCAGCGACATCGCCGTGGAGTGGGAGAGCA<br>ATGGGCAGCCGGAGAACAACTACAAGACCACGCCTCCCGT<br>GCTGGACTCCGACGGCTCCTTCTTCCTCTATAGCAAGCTCAC<br>CGTGGACAAGAGCAGGTGGCAGCAGGGGAACGTCTTCTCAT<br>GCTCCGTGATGCATGAGGCTCTGCACAACCACTACACGCAG<br>AAGAGCCTCTCCCTGTCCCCCGGA |
| 31 | EDB-(κK183C) LC Protein | EIVLTQSPGTLSLSPGERATLSCRASQSVSSSFLAWYQQKPGQA<br>PRLLIYYASSRATGIPDRFSGSGSGTDFTLTISRLEPEDFAVYYC<br>QQTGRIPPTFGQGTKVEIKRTVAAPSVFIFPPSDEQLKSGTASVV<br>CLLNNFYPREAKVQWKVDNALQSGNSQESVTEQDSKDSTYSL<br>SSTLTLSCADYEKHKVYACEVTHQGLSSPVTKSFNRGEC |
| 32 | EDB-(κK183C) LC DNA | GAAATTGTGTTAACGCAGTCTCCAGGCACCCTGTCTTTGTCT<br>CCAGGGGAAAGAGCCACCCTCTCCTGCAGGGCCAGTCAGA<br>GTGTTAGCAGCAGCTTTTTAGCCTGGTACCAGCAGAAACCT<br>GGCCAGGCTCCCAGGCTCCTCATCTATTATGCATCCAGCAG<br>GGCCACTGGCATCCCAGACAGGTTCAGTGGCAGTGGGTCTG<br>GGACAGACTTCACTCTCACCATCAGCAGACTGGAGCCTGAA<br>GATTTTGCAGTGTATTACTGTCAGCAGACGGGTCGTATTCCG<br>CCGACGTTCGGCCAAGGGACCAAGGTGGAAATCAAACGAA<br>CTGTGGCTGCACCATCTGTCTTCATCTTCCCGCCATCTGATG<br>AGCAGTTGAAATCTGGAACTGCCTCTGTTGTGTGCCTGCTG<br>AATAACTTCTATCCCAGAGAGGCCAAAGTACAGTGGAAGGT<br>GGATAACGCCCTCCAATCGGGTAACTCCCAGGAGAGTGTCA<br>CAGAGCAGGACAGCAAGGACAGCACCTACAGCCTCAGCAG<br>CACCCTGACGCTGAGCTGCGCAGACTACGAGAAACACAAA<br>GTCTACGCCTGCGAAGTCACCCATCAGGGCCTGAGCTCGCC<br>CGTCACAAAGAGCTTCAACAGGGGAGAGTGT |

In some aspects of the invention, an EDB ADC includes an antibody, or antigen binding fragment thereof, that binds to extra domain B (EDB) of fibronectin (FN).

In some aspects of the invention, an antibody of the present invention, or antigen binding fragment thereof, has a heavy chain variable region (VH) and a light chain variable region (VL), wherein the VH has three CDRs comprising SEQ ID NOs: 3, 5 and 7. In some aspects of the invention, an antibody, or antigen binding fragment thereof, has a heavy chain variable region (VH) and a light chain variable region (VL), wherein the VL has three CDRs comprising SEQ ID NOs: 12, 13 and 14. An antibody, or antigen-binding fragment thereof, may have a VH having three CDRs comprising SEQ ID NOs: 3, 5 and 7; and a VL having three CDRs comprising SEQ ID NOs: 12, 13 and 14.

In another aspect, an antibody of the present invention, or antigen binding fragment thereof, may have a heavy chain variable region (VH) comprising a VH CDR1 of SEQ ID NO: 3, a VH CDR2 of SEQ ID NO: 5 and a VH CDR3 of SEQ ID NO: 7 (according to Kabat), or a VH CDR1 of SEQ ID NO: 4, a VH CDR2 of SEQ ID NO: 6 and a VH CDR3 of SEQ ID NO: 7 (according to Chothia), or a VH CDR1 of SEQ ID NO: 3 or 4, a VH CDR2 of SEQ ID NO: 5 or 6 and a VH CDR3 of SEQ ID NOs: 7. In another aspect, an antibody, or antigen binding fragment thereof, may have a light chain variable region (VL) comprising a VL CDR1 of SEQ ID NO: 12, a VL CDR2 of SEQ ID NO: 13 and a VL CDR3 of SEQ ID NO: 14 (according to Kabat and Chothia). In a further aspect, an antibody, or antigen binding fragment thereof, may have a VH CDR1 of SEQ ID NO: 3 or 4, a VH CDR2 of SEQ ID NO: 5 or 6 and a VH CDR3 of SEQ ID NOs: 7 and a VL CDR1 of SEQ ID NO: 12, a VL CDR2 of SEQ ID NO: 13 and a VL CDR3 of SEQ ID NO: 14.

In some aspects of the invention, an antibody, or antigen-binding fragment thereof, may heave a heavy chain variable region comprising SEQ ID NOs: 1 or 21 and/or a light chain variable region comprising SEQ ID NO: 10. An antibody, or antigen-binding fragment thereof, may comprise: a heavy chain variable region having an amino acid sequence that is at least 90% identical to SEQ ID NO: 1 and a light chain variable region having an amino acid sequence that is at least 90% identical to SEQ ID NO: 10; a heavy chain variable region having an amino acid sequence that is at least 90% identical to SEQ ID NO: 21 and a light chain variable region having an amino acid sequence that is at least 90% identical to SEQ ID NO: 10; a heavy chain variable region comprising SEQ ID NO: 1 and a light chain variable region comprising SEQ ID NO: 10; or a heavy chain variable region comprising SEQ ID NO: 21 and a light chain variable region comprising SEQ ID NO: 10.

In another aspect of the invention, an antibody, or antigen-binding fragment thereof, may have a heavy chain comprising any one of SEQ ID NOs: 8, 17, 19, 23, 25, 27 and 29, and/or a light chain comprising SEQ ID NOs: 15 or 31.

An antibody of the present invention, or antigen-binding fragment thereof, may comprise: a heavy chain having an amino acid sequence that is at least 90% identical to SEQ ID NO: 8 and a light chain having an amino acid sequence that is at least 90% identical to SEQ ID NO: 15; a heavy chain having an amino acid sequence that is at least 90% identical to SEQ ID NO: 8 and a light chain having an amino acid sequence that is at least 90% identical to SEQ ID NO: 31; a heavy chain having an amino acid sequence that is at least 90% identical to SEQ ID NO: 17 and a light chain having an amino acid sequence that is at least 90% identical to SEQ ID NO: 15; a heavy chain having an amino acid sequence that is at least 90% identical to SEQ ID NO: 17 and a light chain having an amino acid sequence that is at least 90% identical to SEQ ID NO: 31; a heavy chain having an amino acid sequence that is at least 90% identical to SEQ ID NO: 19 and a light chain having an amino acid sequence that is at least 90% identical to SEQ ID NO: 15; a heavy chain having an amino acid sequence that is at least 90% identical to SEQ ID NO: 19 and a light chain having an amino acid sequence that is at least 90% identical to SEQ ID NO: 31; a heavy chain having an amino acid sequence that is at least 90% identical to SEQ ID NO: 23 and a light chain having an amino acid sequence that is at least 90% identical to SEQ ID NO: 15; a heavy chain having an amino acid sequence that is at least 90% identical to SEQ ID NO: 23 and a light chain having an amino acid sequence that is at least 90% identical to SEQ ID NO: 31; a heavy chain having an amino acid sequence that is at least 90% identical to SEQ ID NO: 25 and a light chain having an amino acid sequence that is at least 90% identical to SEQ ID NO: 15; a heavy chain having an amino acid sequence that is at least 90% identical to SEQ ID NO: 25 and a light chain having an amino acid sequence that is at least 90% identical to SEQ ID NO: 31; a heavy chain having an amino acid sequence that is at least 90% identical to SEQ ID NO: 27 and a light chain having an amino acid sequence that is at least 90% identical to SEQ ID NO: 15; a heavy chain having an amino acid sequence that is at least 90% identical to SEQ ID NO: 27 and a light chain having an amino acid sequence that is at least 90% identical to SEQ ID NO: 31; or a heavy chain having an amino acid sequence that is at least 90% identical to SEQ ID NO: 29 and a light chain having an amino acid sequence that is at least 90% identical to SEQ ID NO: 15.

An antibody of the present invention, or antigen-binding fragment thereof, may comprise: a heavy chain comprising SEQ ID NO: 8 and a light chain comprising SEQ ID NO: 15; a heavy chain comprising SEQ ID NO: 8 and a light chain comprising SEQ ID NO: 31; a heavy chain comprising SEQ ID NO: 17 and a light chain comprising SEQ ID NO: 15; a heavy chain comprising SEQ ID NO:17 and a light chain comprising SEQ ID NO: 31; a heavy chain comprising SEQ ID NO:19 and a light chain comprising SEQ ID NO: 15; a heavy chain comprising SEQ ID NO: 19 and a light chain comprising SEQ ID NO: 31; a heavy chain comprising SEQ ID NO: 23 and a light chain comprising SEQ ID NO: 15; a heavy chain comprising SEQ ID NO: 23 and a light chain comprising SEQ ID NO: 31; a heavy chain comprising SEQ ID NO: 25 and a light chain comprising SEQ ID NO: 15; a heavy chain comprising SEQ ID NO: 25 and a light chain comprising SEQ ID NO: 31; a heavy chain comprising SEQ ID NO: 27 and a light chain comprising SEQ ID NO: 15; a heavy chain comprising SEQ ID NO: 27 and a light chain comprising SEQ ID NO: 31; a heavy chain comprising SEQ ID NO: 29 and a light chain comprising SEQ ID NO: 15; or a heavy chain comprising SEQ ID NO: 29 and a light chain comprising SEQ ID NO: 31.

Representative DNAs encoding anti-EDB antibody heavy chain and light chain variable regions comprise SEQ ID NOs: 2 and 22 and SEQ ID NO: 11, respectively. Representative DNAs encoding anti-EDB antibody heavy chains and light chains comprise SEQ ID NOs: 9, 18, 24, 26, 28 and 30, and SEQ ID NOs: 16 and 32, respectively.

TABLE 3

SEQ ID NOs for various anti-EDB antibodies. CDRs in Kabat and (Chothia).

| | VH | VH CDR1 | VH CDR2 | VH CDR3 | HC | VL | VL CDR1 | VL CDR2 | VL CDR3 | LC |
|---|---|---|---|---|---|---|---|---|---|---|
| EDB-L19 | 1 | 3 (4) | 5 (6) | 7 | 8 | 10 | 12 | 13 | 14 | 15 |
| EDB-PFE | 1 | 3 (4) | 5 (6) | 7 | 17 | 10 | 12 | 13 | 14 | 15 |
| EDB-(κK183C-K290C) | 1 | 3 (4) | 5 (6) | 7 | 19 | 10 | 12 | 13 | 14 | 31 |
| EDB-(K94R) | 21 | 3 (4) | 5 (6) | 7 | 23 | 10 | 12 | 13 | 14 | 15 |
| EDB-(κK183C-K94R-K290C) | 21 | 3 (4) | 5 (6) | 7 | 25 | 10 | 12 | 13 | 14 | 31 |
| EDB-(H16-K222R) | 1 | 3 (4) | 5 (6) | 7 | 27 | 10 | 12 | 13 | 14 | 15 |
| EDB-(K94R-H16-K222R) | 21 | 3 (4) | 5 (6) | 7 | 29 | 10 | 12 | 13 | 14 | 15 |

Drugs

Drugs useful in preparation of the disclosed EDB ADCs include any substance having biological or detectable activity, for example, therapeutic agents, detectable labels, binding agents, etc., and prodrugs, which are metabolized to an active agent in vivo. A drug may also be a drug derivative, wherein a drug has been functionalized to enable conjugation with an antibody of the invention.

A therapeutic agent is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulating agents. A cytotoxic effect refers to the depletion, elimination and/or the killing of a target cell(s). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells. A chemotherapeutic agent refers to an agent that is a chemical compound useful in the treatment of cancer. An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious.

In some aspects the drug is a membrane permeable drug. In such aspects, the payload can elicit a bystander effect wherein cells that may not express EDB+ FN or have EDB+ FN bound to their surface, but surround the cell that is bound by the ADC are killed by the cell permeable payload. This occurs when the payload is released from the antibody (i.e., by cleaving of a cleavable linker) and crosses the cellular membrane and, upon diffusion, induces the killing of surrounding cells.

In accordance with the disclosed methods, the EDB ADCs may be produced or generated having (a) an antibody, or antigen binding fragment thereof, that binds to EDB; (b) a linker and (c) a drug. The drug-to-antibody ratio (DAR), or drug loading, indicates the number of drug molecules conjugated per antibody. Compositions, batches, and/or formulations of a plurality of ADCs may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

In aspects of the invention, an EDB ADC may have a DAR of 1, a DAR of 2, a DAR of 3, a DAR of 4, a DAR of 5, a DAR of 6, a DAR of 7, a DAR of 8, a DAR of 9, a DAR of 10, a DAR of 11, a DAR of 12 or a DAR greater than 12. In aspects of the invention, an EDB ADC may have one drug molecule, or 2 drug molecules, or 3 drug molecules, or 4 drug molecules, or drug molecules, or 6 drug molecules, or 7 drug molecules, or 8 drug molecules, or 9 drug molecules, or 10 drug molecules, or 11 drug molecules, or 12 drug molecules or greater than 12 molecules.

In aspects of the invention, an EDB ADC may have average DAR in the range of about 2 to about 4, or an average DAR in the range of about 3 to about 5, or an average DAR in the range of about 4 to about 6, or an average DAR in the range of about 5 to about 7, or an average DAR in the range of about 6 to about 8, or an average DAR in the range of about 7 to about 9, or an average DAR in the range of about 8 to about 10, or an average DAR in the range of about 9 to about 11, or an average DAR in the range of about 10 to about 12, etc. In some aspects the compositions, batches and/or formulations of EDB ADCs may have an average DAR of about 1, or an average DAR of about 2, an average DAR of about 3, or an average DAR of about 4, or an average DAR of about 5, or an average DAR of about 6, or an average DAR of about 7, or an average DAR of about 8, or an average DAR of about 9, or an average DAR of about 10, or an average DAR of about 11, or an average DAR of about 12 or an average DAR greater than 12. As used in the foregoing ranges of average DAR, the term "about" means +/−0.5%.

A composition, batch, and/or formulation of EDB ADCs may be characterized by a preferred range of average DAR, e.g., an average DAR in the range of about 3 to about 5, an average DAR in the range of about 3 to about 4, or an average DAR in the range of about 4 to about 5. Further, a composition, batch, and/or formulation of EDB ADCs may be characterized by a preferred range of average DAR, e.g., an average DAR in the range of 3 to 5, an average DAR in the range of 3 to 4, or an average DAR in the range of 4 to 5.

In some aspects of the invention, a composition, batch, and/or formulation of EDB ADCs may be characterized by an average DAR of about 1.0, or an average DAR of 1.0, or an average DAR of 1.1, or an average DAR of 1.2, or an average DAR of 1.3, or an average DAR of 1.4, or an average DAR of 1.5, or an average DAR of 1.6, or an average DAR of 1.7, or an average DAR of 1.8, or an average DAR of 1.9. In another aspect, a composition, batch, and/or formulation of EDB ADCs may be characterized by an average DAR of about 2.0, or an average DAR of 2.0, or an average DAR of 2.1, or an average DAR of 2.2, or an average DAR of 2.3, or an average DAR of 2.4, or an average DAR of 2.5, or an average DAR of 2.6, or an average DAR of 2.7, or an average DAR of 2.8, or an average DAR of 2.9. In another aspect, a composition, batch, and/or formulation of EDB ADCs may be characterized by an average DAR of about 3.0, or an average DAR of 3.0, or an average DAR of 3.1, or an average DAR of 3.2, or an average DAR of 3.3, or an average DAR of 3.4, or an average DAR of 3.5, or an average DAR of 3.6, or an average DAR of 3.7, or an average DAR of 3.8, or an average DAR of 3.9. In another aspect, a composition, batch, and/or formulation of EDB ADCs may be characterized by an average DAR of about 4.0, or an average DAR of 4.0, or an average DAR of 4.1, or an average DAR of 4.2, or an average DAR of 4.3, or an average DAR of 4.4, or an average DAR of 4.5, or an average DAR of 4.6, or an average DAR of 4.7, or an average DAR of 4.8, or an average DAR of 4.9, or an average DAR of 5.0.

In another aspect, a composition, batch, and/or formulation of EDB ADCs may be characterized by an average DAR of 12 or less, an average DAR of 11 or less, an average DAR of 10 or less, an average DAR of 9 or less, an average DAR of 8 or less, an average DAR of 7 or less, an average DAR of 6 or less, an average DAR of 5 or less, an average DAR of 4 or less, an average DAR of 3 or less, an average DAR of 2 or less or an average DAR of 1 or less.

In other aspects, a composition, batch, and/or formulation of EDB ADCs may be characterized by an average DAR of 11.5 or less, an average DAR of 10.5 or less, an average DAR of 9.5 or less, an average DAR of 8.5 or less, an average DAR of 7.5 or less, an average DAR of 6.5 or less, an average DAR of 5.5 or less, an average DAR of 4.5 or less, an average DAR of 3.5 or less, an average DAR of 2.5 or less, an average DAR of 1.5 or less.

In some aspects of the present invention, the methods for conventional conjugation via cysteine residues and purification conditions disclosed herein provide a composition, batch, and/or formulation of EDB ADCs with an optimized average DAR in the range of about 3 to 5, preferably about 4.

In some aspects of the present invention, the methods for site-specific conjugation via engineered cysteine residues and purification conditions disclosed herein provide a composition, batch, and/or formulation of EDB ADCs with an optimized average DAR in the range of about 3 to 5, preferably about 4.

In some aspects of the present invention, the methods for site-specific conjugation via transglutaminase-based conjugation and purification conditions disclosed herein provide a composition, batch, and/or formulation of EDB ADCs with an optimized average DAR in the range of about 1 to 3, preferably about 2.

Examples of cytotoxic agents include, but are not limited to an anthracycline, an auristatin, CC-1065, a dolastatin, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof. Plant toxins, other bioactive proteins, enzymes (i.e., ADEPT), radioisotopes, photosensitizers (i.e., for photodynamic therapy) may also be used.

The anthracyclines are derived from bacteria *Streptomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, (1998). Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAE (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB). and other novel In some aspects, the drug/payload is an auristatin. Auristatins inhibit cell proliferation by inhibiting the formation of microtubules during mitosis through inhibition of tubulin polymerization. PCT International Publication No. WO 2013/072813, which is incorporated herein by reference in its entirety, discloses auristatins that are useful in the EDB ADCs of the present invention and provides methods of producing the auristatins. For example, payload 0101 having the structure:

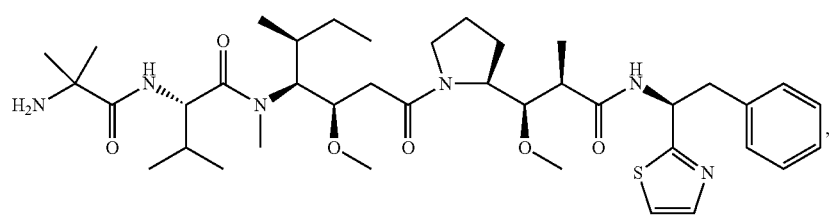 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

payload 1569 having the structure:
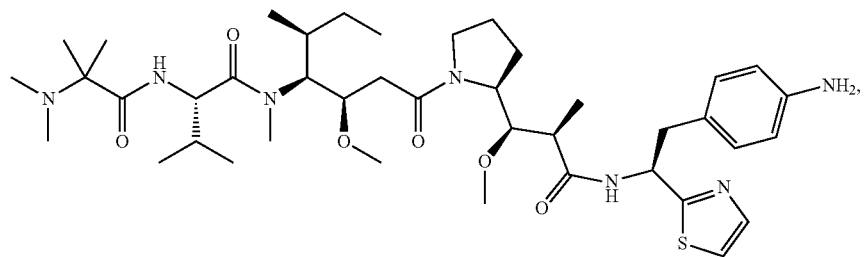 [SMILES: CC[C@H](C)[C@@H]([C@@H](CC(=O)N1CCC[C@H]1[C@H](OC)[C@@H](C)C(=O)N[C@@H](Cc1ccc(N)cc1)c1nccs1)OC)N(C)C(=O)[C@@H](NC(=O)C(C)(C)N(C)C)C(C)C]
payload 9411 having the structure:
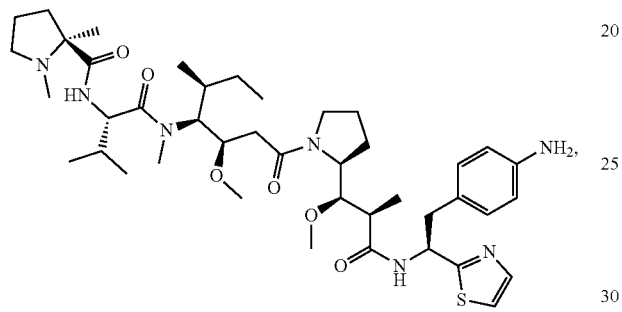
payload 4574 having the structure:
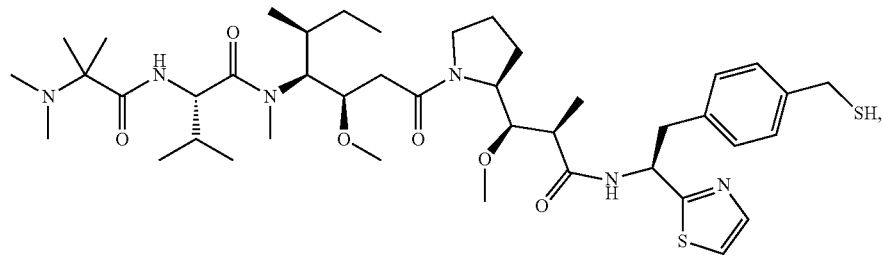 [SMILES: CC[C@H](C)[C@@H]([C@@H](CC(=O)N1CCC[C@H]1[C@H](OC)[C@@H](C)C(=O)N[C@@H](Cc1ccc(CS)cc1)c1nccs1)OC)N(C)C(=O)[C@@H](NC(=O)C(C)(C)N(C)C)C(C)C]
payload DM1 having the structure:
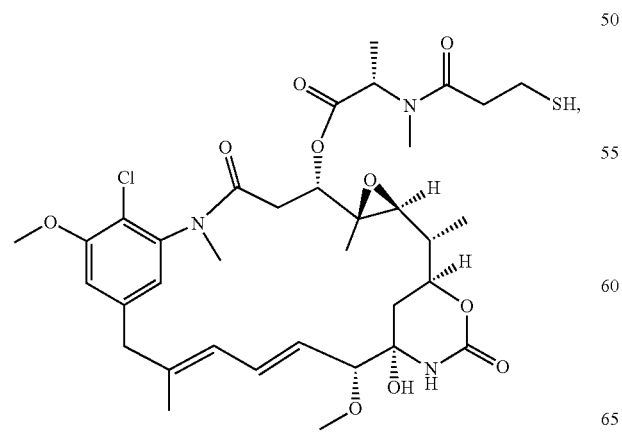

and payload Cemadotin having the structure:

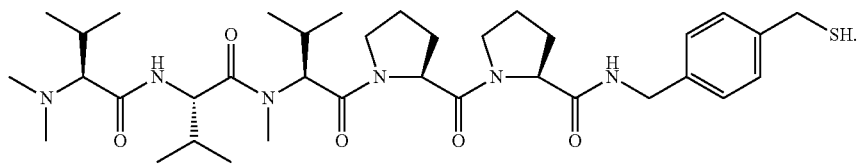 [SMILES: CC(C)[C@H](NC(=O)[C@H](C(C)C)N(C)C)C(=O)N(C)[C@H](C(=O)N1CCC[C@H]1C(=O)N1CCC[C@H]1C(=O)NCc1ccc(CS)cc1)C(C)C]

Duocarmycin and CC-1065 are CPI-based monomers that act as DNA alkylating agents with cytotoxic potency. See Boger and Johnson, *PNAS* 92:3642-3649, 1995. Exemplary dolastatins include, but are not limited to, (+)-docarmycin A and (+)-duocarmycin SA, and (+)-CC-1065.

In some aspects, the drug/payload is a CPI or CBI dimer. CPI dimers induce inter-strand DNA crosslinking and potent cytotoxicity. PCT International Publication No. WO2015/110935, which is incorporated herein by reference in its entirety, discloses CPI and CBI dimers that are useful in the EDB ADCs of the present invention and provides methods of producing the CPI and CBI dimers. For example, payload CPI-8314 dimer having the structure:

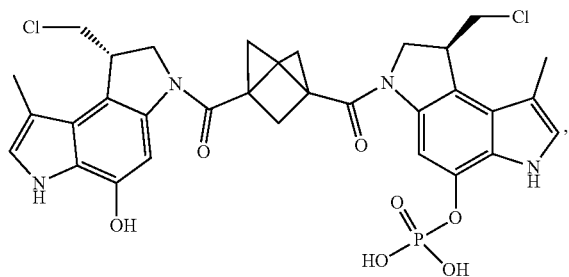 [SMILES: Cc1c[nH]c2c(O)cc3c(c12)[C@H](CCl)CN3C(=O)C12CC3(C(=O)N4C[C@@H](CCl)c5c4cc(OP(=O)(O)O)c4[nH]cc(C)c54)CC13C2]

and payload CPI-0326 having the structure:

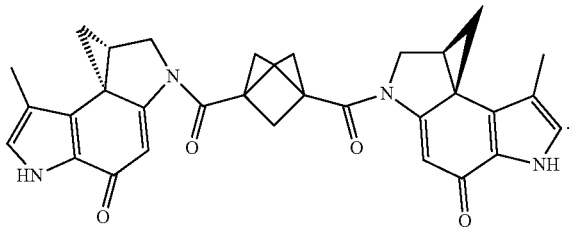 [SMILES: Cc1c[nH]c2c1[C@@]13C[C@@H]1CN(C(=O)C14CC5(C(=O)N6C[C@H]7C[C@@]78C6=CC(=O)c6[nH]cc(C)c68)CC15C4)C3=CC2=O]

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin. Calicheamicin, also called the LL-E33288 complex, for example, β-calicheamicin, γ-calicheamicin or N-acetyl-γ-calicheamicin (gamma-calicheamicin ($\gamma_1$)), is an enediyne antibiotic that was originally isolated as a natural product from the soil organism *Micromonospora echinospora* ssp. calichensis (Zein et al. Science 27; 240(4856):1198-1201, 1988); it generates double-strand DNA breaks and subsequently induces apoptosis in target cells (Zein et al. Science 27; 240(4856):1198-1201, 1988; Nicolaou et al. Chem. Biol. September; 1(1):57-66, 1994; Prokop et al. Oncogene 22:9107-9120, 2003). The disulfide analog is N-acetyl-γ-calicheamicin dimethyl hydrazide.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some aspects of the invention, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, xanthines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

Immunomodulatory agents useful in the invention also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

In some aspects of the invention, the drug is a therapeutic protein including, but is not limited to, a toxin, a hormone, an enzyme, and a growth factor.

Examples of a toxin protein (or polypeptide) include, but are not limited to, diphtheria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

Examples of hormones include, but are not limited to, estrogens, androgens, progestins and corticosteroids.

In some aspects of the invention, the drug is an oligonucleotide, such as anti-sense oligonucleotides.

Additional drugs useful in the invention include anti-angiogenic agents that inhibit blood vessel formation, for example, farnesyltransferase inhibitors, COX-2 inhibitors, VEGF inhibitors, bFGF inhibitors, steroid sulphatase inhibitors (e.g., 2-methoxyoestradiol bis-sulphamate (2-MeOE2bisMATE)), interleukin-24, thrombospondin, metallospondin proteins, class I interferons, interleukin 12, protamine, angiostatin, laminin, endostatin, and prolactin fragments.

Anti-proliferative agents and pro-apoptotic agents include activators of PPAR-gamma (e.g., cyclopentenone prostaglandins (cyPGs)), retinoids, triterpinoids (e.g., cycloartane, lupane, ursane, oleanane, friedelane, dammarane, cucurbitacin, and limonoid triterpenoids), inhibitors of EGF receptor (e.g., HER4), rampamycin, CALCITRIOL® (1,25-dihydroxycholecalciferol (vitamin D)), aromatase inhibitors (FEMARA® (letrozone)), telomerase inhibitors, iron chelators (e.g., 3-aminopyridine-2-carboxaldehyde thiosemicarbazone (Triapine)), apoptin (viral protein 3-VP3 from chicken aneamia virus), inhibitors of Bcl-2 and Bcl-X(L), TNF-alpha, FAS ligand, TNF-related apoptosis-inducing ligand (TRAIL/Apo2L), activators of TNF-alpha/FAS ligand/TNF-related apoptosis-inducing ligand (TRAIL/Apo2L) signaling, and inhibitors of PI3K-Akt survival pathway signaling (e.g., UCN-01 and geldanamycin).

Representative chemotherapeutic agents include alkylating agents such as thiotepa and cyclosphosphamide; alkyl sulfonates such as busulfan, improsulfan and piposulfan; aziidines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfarnide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenal such as arninoglutethimide, mitotane, trilostane; folic acid replenisher such as frolinic acid; aceglatone; aldophospharnide glycoside; arninolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL®, Bristol-Myers Squibb Oncology of Princeton, N.J.) and doxetaxel (TAXOTERE®, Rhone-Poulenc Rorer of Antony, France); chiorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aininopterin; xeloda; ibandronate; CPT-11; topoisomerase inhibitor RFS 2000; difluoromethylornithine (DMFO); retinoic acid; esperamicins; and capecitabine.

Additional therapeutic agents that may be used in accordance with the present invention include photosensitizing agents, such as U.S. Publication No. 20020197262 and U.S. Pat. No. 5,9532,39, which are incorporated herein by reference in its entirety, for photodynamic therapy; magnetic particles for thermotherapy, such as U.S. Publication No. 20030032995, which is incorporated herein by reference in its entirety; binding agents, such as peptides, ligands, cell adhesion ligands, etc., and prodrugs such as phosphate-containing prodrugs, thiophosphate-containing prodrugs, sulfate containing prodrugs, peptide containing prodrugs, β-lactam-containing prodrugs, substituted phenoxyacetamide-containing prodrugs or substituted phenylacetamide-containing prodrugs, 5-fluorocytosine and other 5-fluorouridine prodrugs that may be converted to the more active cytotoxic free drug.

For diagnostic methods using anti-EDB antibodies, a drug may include a detectable label used to detect the presence of EDB+ FN-expressing ECM or cells in vitro or in vivo. Radioisotopes that are detectable in vivo, such as those labels that are detectable using scintigraphy, magnetic resonance imaging, or ultrasound, may be used in clinical diagnostic applications. Useful scintigraphic labels include positron emitters and γ-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids may be entrapped in porous inorganic particles that are released as microbubble contrast agents. For in vitro detection, useful detectable labels include fluorophores, detectable epitopes or binding agents, and radioactive labels.

Thus, in some aspects of the invention, the drug is an imaging agent (e.g., a fluorophore or a PET (Positron Emission Tomography) label, SPECT (Single-Photon Emission Computed Tomorgraphy) label), or MM (Magnetic Resonance Imaging) label.

The term "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-detectable entity such as a toxin.

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, ALEXA FLUOR® (Molecular Probes, Inc.; fluorescent chemicals and biomolecule labeling kits) (e.g., ALEXA FLUOR® 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101).

Therapeutic or diagnostic radioisotopes or other labels (e.g., PET or SPECT labels) can be incorporated in the agent for conjugation to the anti-EDB antibodies as described herein. The isotope may be directly bound to the antibody, for example, at a cysteine residue present in the antibody, or a chelator may be used to mediate the binding of the antibody and the radioisotope. Radioisotopes suitable for radiotherapy include but are not limited to α-emitters, β-emitters, and auger electrons. For diagnostic applications, useful radioisotopes include positron emitters and γ-emitters. An anti-EDB antibody of the invention may further be iodinated, for example, on a tyrosine residue of the antibody, to facilitate detection or therapeutic effect of the antibody.

Examples of a radioisotope or other labels include, but are not limited to, $^{3}$H, $^{11}$C, $^{13}$N, $^{14}$C, $^{15}$N, $^{15}$O, $^{35}$S, $^{18}$F, $^{32}$P, $^{33}$P, $^{47}$Sc, $^{51}$Cr, $^{57}$CO, $^{58}$CO, $^{5}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te, $^{126}$I, $^{131}$I, $^{131}$In, $^{133}$I, $^{142}$Pr, $^{143}$Pr, $^{153}$Pb, $^{153}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Ra, $^{224}$Ac, and $^{225}$AC.

Linkers

EDB ADCs of the present invention may be prepared using a linker to directly or indirectly link or conjugate a drug to an antibody. A linker is a bifunctional compound that links a drug and an antibody to form an ADC. Such ADCs allow the selective delivery of drugs via antibodies that bind to specific antigens or proteins. Suitable linkers include, for example, cleavable and non-cleavable linkers. A cleavable linker is typically susceptible to cleavage and release of drug by specific intracellular and extracellular conditions. Major mechanisms by which a conjugated drug may be cleaved from an antibody intracellularly include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. A conjugated drug may be cleaved from an antibody extracellularly by proteases in a tumor microenvironment (TME), such as cathepsins. As a result of these varying mechanisms for cleavage, mechanisms of linking the drug to the antibody also vary widely and any suitable linker can be used.

Suitable linkers may include any cleavable linker. In some aspects, suitable linkers include a valine-citrulline (val-cit) linker, a phenylalanine-lysine (phe-lys) linker, or a maleimidocaproyl-valine-citrulline-p-aminobenzyloxycarbonyl (vc) linker, or contain a dipeptide attached to additional immolation elements, such as N~2~-acetyl-L-lysyl-L-valyl-L-citruline-p-aminobenzyloxycarbonyl-N,N'-dimethylaminoethyl-CO-(AcLys-vc) linker, suitable for transglutaminase-based conjugation technology. In another aspect, suitable linkers include disulfide linkers, such as sulfanyl pyridine (diS) linker and 2-(pyridin-2-yldisulfanyl)ethyl carbamoyl (diS-C$_2$OCO) linker. In another aspect, the linker may be a non-cleavable linker, such as maleimidocaproyl (mc), maleimido-heptanoyl (me) and maleimido-Peg6C2 (MalPeg6C2). In other aspects, suitable linkers include linkers hydrolyzable at a specific pH or a pH range, such as a hydrazone linker.

The linker may be covalently bound to the antibody through a thioester linkage, for instance by reaction of a maleimide or haloacetamide, present on the linker with a native or engineered cysteine residue present on the antibody. In another aspect, the linker may be covalently bound to the antibody through amide linkages to lysine residues present on the antibody, for instance by reaction of an N-hydroxy-succinimide activated carboxylic acid present on the linker with a free amine of a lysine residue. In another aspect, the linker may be covalently bound to the antibody through amide linkages to the side chains of glutamine residues present or engineered into the antibody, for instance by enzymatic reaction catalyzed by a transglutaminase enzyme that creates a new amide linkage from a primary amine present on the linker with a side chain amide of a glutamine residue.

In some aspects, linkers of the present invention include:
"mc-vc-PABC" or "vc-PABC" or "vc" linker having the structure:

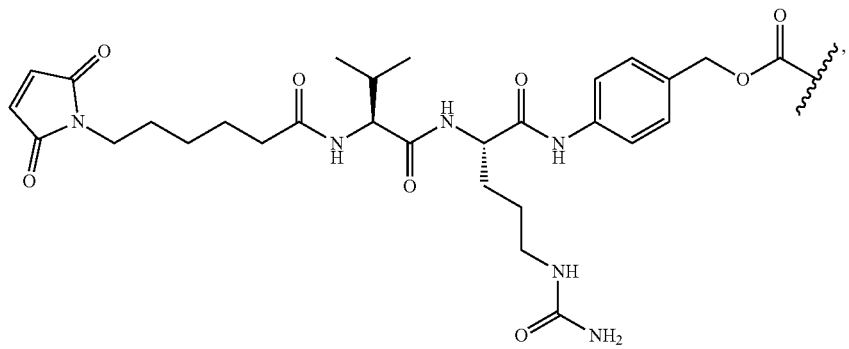 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

"AcLys-vc-PABC-DMAE-CO" or "AcLys-vc" linker having the structure:

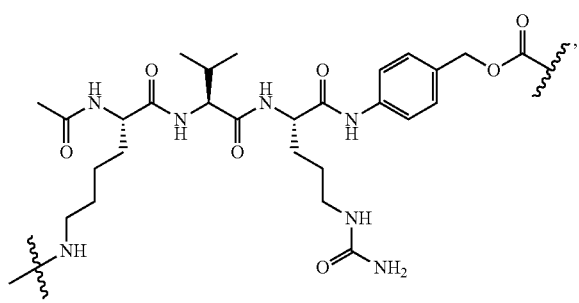 [SMILES: *NCCCC[C@H](NC(C)=O)C(=O)N[C@H](C(=O)N[C@@H](CCCNC(N)=O)C(=O)Nc1ccc(COC(*)=O)cc1)C(C)C]

diS linker having the structure:

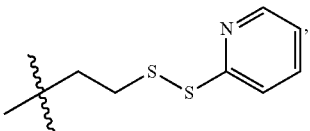 [SMILES: *CCSSc1ccccn1]

and
diS-C$_2$OCO linker having the structure:

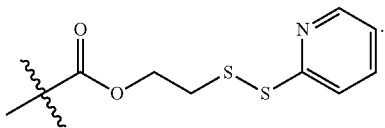 [SMILES: *C(=O)OCCSSc1ccccn1]

Methods of Preparing EDB ADCs

Provided herein are methods for preparing EDB ADCs of the present invention. The present invention further provides for a process for producing or generating conventionally and site-specific conjugated EDB ADCs as disclosed herein and may include (a) linking the linker to the drug; (b) conjugating the linker-drug moiety to the antibody; and (c) purifying the antibody drug conjugate. See Examples 3 and 4.

In some aspects, EDB ADCs may be generated using conventional, non-specific conjugation of linker-payload moieties through one or more cysteine residues of an anti-EDB antibody, or an antigen binding fragment thereof.

In another aspect, EDB ADCs may be generated using site-specific conjugation of linker-payload moieties though one or more reactive cysteine residues engineered into an anti-EDB antibody constant domain. Methods of preparing antibodies for site-specific conjugation via engineered cysteine residues are described in PCT International Publication No. WO2013/093809, which is incorporated herein by reference in its entirety.

One or more amino acid residues of an anti-EDB antibody heavy chain may be substituted to another amino acid, such as a cysteine residue, for the purpose of conjugation to a drug or payload. In one aspect, the invention provides an anti-EDB antibody, or antigen binding fragment thereof, comprising an antibody heavy chain constant region comprising an engineered cysteine residue at position: 118 (114 according to Kabat), 246, 249, 265, 267, 270, 276, 278, 283, 290, 292, 293, 294, 300, 302, 303, 314, 315, 318, 320, 327, 332, 333, 334, 336, 345, 347, 354, 355, 358, 360, 362, 370, 373, 375, 376, 378, 380, 382, 386, 388, 390, 392, 393, 401, 404, 411, 413, 414, 416, 418, 419, 421, 428, 431, 432, 437, 438, 439, 443 or 444, or any combination thereof, according to the numbering of the EU index of Kabat). In particular, positions 118 (114 according to Kabat), 290, 334, 347, 373, 375, 380, 388, 392, 421, 443, or any combination thereof may be used. Additional cysteine substitutions may be introduced.

In another aspect, the invention provides an anti-EDB antibody, or antigen binding fragment thereof, comprising a heavy chain constant domain comprising an engineered cysteine residue at position 290 (K290C), according to the numbering of the EU index of Kabat.

One or more amino acid residues of an anti-EDB antibody light chain constant domain may be substituted to another amino acid, such as a cysteine residue, for the purpose of conjugation to a drug or payload. In one aspect, the invention provides an anti-EDB antibody, or antigen binding fragment thereof, comprising an antibody light chain constant region comprising (i) an engineered cysteine residue at position 110, 111, 125, 149, 155, 158, 161, 183, 185, 188, 189, 191, 197, 205, 207, 208 or 210, or any combination thereof, according to the numbering of Kabat); (ii) an engineered cysteine residue at a position corresponding to residue 4, 42, 81, 100, 103, or any combination thereof, of SEQ ID NO: 37, when the constant domain is aligned with SEQ ID NO: 37 (kappa light chain); or (iii) an engineered cysteine residue at a position corresponding to residue 4, 5, 19, 43, 49, 52, 55, 78, 81, 82, 84, 90, 96, 97, 98, 99, 101, or any combination thereof, of SEQ ID NO: 38, when the constant domain is aligned with SEQ ID NO: 38 (lambda light chain). Additional cysteine substitutions may be introduced.

In another aspect, the invention provides an anti-EDB antibody or antigen binding fragment thereof comprising an antibody kappa light chain constant region comprising (i) an engineered cysteine residue at position 111, 149, 188, 207, 210, or any combination thereof (preferably 111 or 210), according to the numbering of Kabat; or (ii) an engineered cysteine residue at a position corresponding to residue 4, 42, 81, 100, 103, or any combination thereof, of SEQ ID NO: 37 (preferably residue 4 or 103), when the constant domain is aligned with SEQ ID NO: 37.

In another aspect, the invention provides an anti-EDB antibody or antigen binding fragment thereof comprising an antibody lambda light chain constant region comprising (i) an engineered cysteine residue at position 110, 111, 125, 149, 155, 158, 161, 185, 188, 189, 191, 197, 205, 206, 207, 208, 210, or any combination thereof (preferably 110, 111, 125, 149, or 155), according to the numbering of Kabat; or (ii) an engineered cysteine residue at a position corresponding to residue 4, 5, 19, 43, 49, 52, 55, 78, 81, 82, 84, 90, 96, 97, 98, 99, 101, or any combination thereof of SEQ ID NO: 38 (preferably residue 4, 5, 19, 43, or 49), when the constant domain is aligned with SEQ ID NO:38.

In another aspect, the invention provides an anti-EDB antibody, or antigen binding fragment thereof, comprising a light chain constant domain comprising (i) an engineered cysteine residue at position 183 (κK183C), according to the numbering of Kabat; or (ii) an engineered cysteine residue at a position corresponding to residue 76 of SEQ ID NO: 37, when said constant domain is aligned with SEQ ID NO: 37.

```
(Cκ constant domain)
                                          SEQ ID NO: 37
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC (Cλ constant domain)
                                          SEQ ID NO 38
GQPKANPTVT LFPPSSEELQ ANKATLVCLI SDFYPGAVTV
AWKADGSPVK AGVETTKPSK QSNNKYAASS YLSLTPEQWK
SHRSYSCQVT HEGSTVEKTV APTECS
```

In another aspect, EDB ADCs may be generated using site-specific conjugation technology though one or more engineered acyl donor glutamine-containing tags or endogenous glutamine residues made reactive in an anti-EDB antibody constant region. Methods of preparing antibodies for site-specific conjugation via acyl donor glutamine-containing tags or glutamine residues are described in PCT International Publication No. WO2012/059882, which is incorporated herein by reference in its entirety.

In some aspects, the acyl donor glutamine-containing tag comprises at least one glutamine (Q) and may be attached to different position of the heavy and/or light chain (i.e., at the N-terminus, C-terminus or internally). In another aspect, the acyl donor glutamine-containing tag may comprise an amino acid sequence selected from: LLQGG (SEQ ID NO: 39), LLQG (SEQ ID NO: 40), LSLSQG (SEQ ID NO: 41), GGGLLQGG (SEQ ID NO: 42), GLLQG (SEQ ID NO: 43), LLQ, GSPLAQSHGG (SEQ ID NO: 44), GLLQGGG (SEQ ID NO: 45), GLLQGG (SEQ ID NO: 46), GLLQ (SEQ ID NO: 47), LLQLLQGA (SEQ ID NO: 48), LLQGA (SEQ ID NO: 49), LLQYQGA (SEQ ID NO: 50), LLQGSG (SEQ ID NO: 51), LLQYQG (SEQ ID NO: 52), LLQLLQG (SEQ ID NO: 53), SLLQG (SEQ ID NO: 54), LLQLQ (SEQ ID NO: 55), LLQLLQ (SEQ ID NO: 56), and LLQGR (SEQ ID NO: 57). In some aspects, an acyl donor glutamine-containing tag replaces wild type amino acid positions in a heavy chain constant domain. In some aspects, an anti-EDB antibody may comprise an acyl glutamine-containing tag having the amino acid sequence LLQG (SEQ ID NO: 40) that replaces the amino acids at positions E294-N297 (according to the EU index of Kabat) of the heavy chain.

Optimal reaction conditions for the generation of ADCs may be empirically determined by a variation of reaction variables such as temperature, pH, linker-payload moiety input, and additive concentration. Conditions suitable for conjugation of other drugs may be determined by those skilled in the art without undue experimentation. Representative methods for conjugating and characterizing EDB ADCs are described in Examples 3 and 4.

Following conjugation, the conjugates may be separated, purified from unconjugated reactants and/or aggregated forms of the conjugates, and characterized by conventional methods. This includes processes such as, but not limited to, mass spectrometry, size exclusion chromatography (SEC), ultrafiltration/diafiltration, ion exchange chromatography (IEC), chromatofocusing (CF), site-directed mutagenesis, fluorescence-labeling, X-ray crystallography, high performance liquid chromatography (HPLC), fast protein liquid chromatography (FPLC), Sephacryl S-200 chromatography or hydrophobic interaction chromatography (HIC). Suitable HIC media includes, but is not limited to, Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

Table 13 provides EDB ADCs produced according to the conjugation and purification methods described herein and used to generate data provided in the Examples.

In some aspects of the invention, EDB ADCs of the present invention comprise (a) an antibody, or antigen binding fragment thereof, that binds to EDB; (b) a linker and (c) a drug.

In another aspect of the invention, EDB ADCs of the present invention comprise (a) an antibody, or antigen binding fragment thereof, that binds to EDB; (b) a linker and (c) a drug, wherein the linker is a cleavable or non-cleavable linker. In some aspects, the linker is vc, diS, diS-C₂OCO or AcLys-vc.

In another aspect of the invention, EDB ADCs of the present invention comprise (a) an antibody, or antigen binding fragment thereof, that binds to EDB; (b) a linker and (c) a drug, wherein the drug is cytotoxic agent. In some aspects, the drug is an auristatin. In some aspects, the drug is a CPI or CBI dimer. In some aspects, the auristatin is 0101, 1569, 9411 or 4574. In some aspects, the CPI dimer is CPI-8314 or CPI-0326.

In some aspects of the invention, EDB ADCs of the present invention comprise (a) an antibody, or antigen binding fragment thereof, comprising: a heavy chain comprising SEQ ID NO: 8 and a light chain comprising SEQ ID NO: 15; a heavy chain comprising SEQ ID NO: 8 and a light chain comprising SEQ ID NO: 31; a heavy chain comprising SEQ ID NO: 17 and a light chain comprising SEQ ID NO: 15; a heavy chain comprising SEQ ID NO:17 and a light chain comprising SEQ ID NO: 31; a heavy chain comprising SEQ ID NO:19 and a light chain comprising SEQ ID NO: 15; a heavy chain comprising SEQ ID NO: 19 and a light chain comprising SEQ ID NO: 31; a heavy chain comprising SEQ ID NO: 23 and a light chain comprising SEQ ID NO: 15; a heavy chain comprising SEQ ID NO: 23 and a light chain comprising SEQ ID NO: 31; a heavy chain comprising SEQ ID NO: 25 and a light chain comprising SEQ ID NO:

15; a heavy chain comprising SEQ ID NO: 25 and a light chain comprising SEQ ID NO: 31; a heavy chain comprising SEQ ID NO: 27 and a light chain comprising SEQ ID NO: 15; heavy chain comprising SEQ ID NO: 27 and a light chain comprising SEQ ID NO: 31; a heavy chain comprising SEQ ID NO: 29 and a light chain comprising SEQ ID NO: 15; or a heavy chain comprising SEQ ID NO: 29 and a light chain comprising SEQ ID NO: 31; (b) a linker and (c) a drug. In some aspects, the linker is a cleavable or non-cleavable linker. In some aspects, the linker is vc, diS, diS-$C_2$OCO or AcLys-vc. In some aspects, the drug is cytotoxic agent. In some aspects, the drug is an auristatin. In some aspects, the drug is a CPI or CBI dimer. In some aspects, the auristatin is 0101, 1569, 9411 or 4574. In some aspects, the CPI dimer is CPI-8314 or CPI-0326.

Uses of EDB ADCs

The anti-EDB antibodies and EDB ADCs of the present invention are useful in various applications including, but are not limited to, therapeutic treatment methods and diagnostic treatment methods.

The present invention provides a method for treating EDB+ FN-expressing disorders or diseases, such as non-cancers or cancers associated with EDB+ FN expression and/or EDB+ FN-expressing cancers, in a subject. The invention also provides an EDB ADC, or a pharmaceutical composition, as described herein, for use in a method for treating an EDB+ FN-expressing disorder, such as non-cancers or cancers associated with EDB+ FN expression and/or EDB+ FN-expressing cancers, in a subject. The invention further provides the use of an EDB ADC, or a pharmaceutical composition, as described herein, in the manufacture of a medicament for treating an EDB+ FN-expressing disorder, such as non-cancers or cancers associated with EDB+FN expression and/or EDB+ FN-expressing cancers, in a subject.

In some aspects, the invention provides a method of inhibiting tumor growth or progression in a subject who has an EDB-expressing disorder, such as non-cancers or cancers associated with EDB+ FN expression and/or EDB-expressing cancers, including administering to the subject in need thereof an effective amount of a composition (i.e., a pharmaceutical composition) having one or more EDB ADCs described herein. In other aspects of the invention, provided is a method of inhibiting metastasis of cancer cells associated with EDB+FN expression and/or EDB+ FN-expressing cancers in a subject, including administering to the subject in need thereof an effective amount of a composition (i.e., a pharmaceutical composition) having one or more EDB ADCs described herein. In other aspects of the invention, provided is a method of inducing regression of a tumor associated with EDB+ FN expression and/or EDB+ FN-expressing cancers in a subject, including administering to the subject in need thereof an effective amount of a composition (i.e., a pharmaceutical composition) having one or more EDB ADCs described herein.

In some aspects, the EDB+ FN expression may be detected in the extracellular matrix (ECM) adjacent to tumor cells. EDB+ FN may be expressed by cells other than fibroblasts in the tumor microenvironment, including tumor cells. The secreted EDB+ FN may be then deposited in the matrix adjacent to tumor cells, or on the plasma membrane of tumor cells. In other aspects, the invention provides a pharmaceutical composition comprising one or more EDB ADCs described herein for use in a method as described above. In other aspects, the invention provides the use of one or more EDB ADCs as described herein or a pharmaceutical composition comprising the EDB ADCs as described herein in the manufacture of a medicament for use in the methods described above.

Cancers associated with EDB+ FN expression and/or EDB+ FN-expressing cancers may generally include any cancer associated with tissue remolding. Further, cancers associated with EDB+ FN expression and/or EDB+ FN-expressing cancers may include, but are not limited to, solid tumors and blood cancers. In some aspects, solid tumors include, but are not limited to, thyroid cancer, sarcoma, breast cancer, pancreatic cancer, glioblastoma, gallbladder cancer, kidney cancer, skin cancer, uterine cancer, mesothelioma, colorectal cancer, head and neck cancer, ovarian cancer, bladder cancer, testicular cancer, prostate cancer, liver cancer, endocrine cancer, thymus cancer, brain cancer, adrenal cancer, eye cancer cervical cancer and lung cancer. In another aspect, blood cancers include, but are not limited to, leukemia, lymphoma and myeloma.

The EDB ADCs of the present invention are useful in treating EDB+ FN-expressing disorders, such as cancers associated with EDB+ FN expression and/or EDB+ FN-expressing cancers. EDB ADCs of the invention may be used to treat cancers that express high levels of EDB+ FN, moderate levels of EDB+ FN or low levels of EDB+ FN.

Thus, patients to be treated with EDB ADCs of the invention may be selected based on biomarker expression, including but not limited to mRNA (qPCR) of bulk tumor samples and elevated expression of EDB+ FN protein which results in a patient population selected for enriched target expression rather than tumor origin or histology. Target expression can be measured as a function of the number of cells staining combined with the intensity of the cells staining.

Cancer growth or abnormal proliferation refers to any one of a number of indices that suggest change within cells to a more developed cancer form or disorder state. Inhibition of growth of cancer cells or cells of a non-neoplastic proliferative disorder may be assayed by methods known in the art, such as delayed tumor growth and inhibition of metastasis. Other indices for measuring inhibition of cancer growth include a decrease in cancer cell survival, a decrease in tumor volume or morphology (for example, as determined using computed tomographic (CT), sonography, or other imaging method), destruction of tumor vasculature, improved performance in delayed hypersensitivity skin test, an increase in the activity of cytolytic T-lymphocytes, and a decrease in levels of tumor-specific antigens.

Desired outcomes of the disclosed therapeutic methods are generally quantifiable measures as compared to a control or baseline measurement. As used herein, relative terms such as "improve," "increase," or "reduce" indicate values relative to a control or comparative molecule, such as a measurement in the same individual prior to initiation of treatment described herein, or a measurement in a control individual (or multiple control individuals) in the absence of the treatment described herein. A representative control individual is an individual afflicted with the same form of cancer as the individual being treated, who is about the same age as the individual being treated (to ensure that the stages of the disorder in the treated individual and the control individual are comparable.

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," statistical manipulations of the data can be "p-value." Those p-values that fall below a user-defined cut-off point are regarded as significant. A p-value less than or equal to 0.1, less than 0.05, less than 0.01, less than 0.005, or less than 0.001 may be regarded as significant.

In Vivo Detection and Diagnosis

In another aspect, provided is a method of detecting, diagnosing, and/or monitoring an EDB+ FN-expressing disorder, such as cancers associated with EDB+ FN expression and/or EDB+ FN-expressing cancers. For example, the anti-EDB antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

Following administration of an EDB ADC to a subject, wherein the drug is a detectable label, and after a time sufficient for binding, the biodistribution of EDB+ FN protein bound by the antibody may be visualized. The disclosed diagnostic methods may be used in combination with treatment methods. In addition, EDB ADCs of the invention may be administered for the dual purpose of detection and therapy.

Representative non-invasive detection methods include scintigraphy (e.g., SPECT (Single Photon Emission Computed Tomography), PET (Positron Emission Tomography), gamma camera imaging, and rectilinear scanning), magnetic resonance imaging (e.g., convention magnetic resonance imaging, magnetization transfer imaging (MTI), proton magnetic resonance spectroscopy (MRS), diffusion-weighted imaging (DWI) and functional MR imaging (fMRI)), and ultrasound.

Formulations

The present invention further provides pharmaceutical compositions including any of the EDB ADCs disclosed herein and a pharmaceutically acceptable carrier. Further, the compositions may include more than one EDB ADC disclosed herein.

The composition used in the present invention may further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule. Pharmaceutically acceptable excipients are further described herein.

Various formulations of the EDB ADCs may be used for administration, including but not limited to, formulations comprising a pharmaceutically acceptable excipient. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some aspects of the invention, these agents may be formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of EDB ADCs used in accordance with the present invention may be prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Therapeutic EDB ADC compositions are generally placed into a container having a sterile access port, for example, an intravenous solution bag or vial having a stopper pierceable by a hypodermic injection needle. The compositions according to the present invention may be in unit dosage forms such as tablets, pills, capsules, powders, granules, solutions or suspensions, or suppositories, for oral, parenteral or rectal administration, or administration by inhalation or insufflation.

Suitable surface-active agents include, in particular, non-ionic agents, such as polyoxyethylenesorbitans (e.g. Tween™ 20, 40, 60, 80 or 85) and other sorbitans (e.g. Span™ 40, 60, 80 or 85). Compositions with a surface-active agent will conveniently include between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can include fat droplets between 0.1 and 1.0 particularly 0.1 and 0.5 and have a pH in the range of 5.5 to 8.0. The emulsion compositions can be those prepared by mixing an EDB ADC with INTRALIPID™ or the components thereof (soybean oil, egg phospholipids, glycerol and water).

The invention also provides kits for use in the instant methods. Kits of the invention include one or more containers including an EDB antibody or an EDB ADC as described herein and instructions for use in accordance with any of the methods of the invention described herein. Generally, these instructions include a description of administration of the EDB antibody or EDB ADC for the above described diagnostic or therapeutic treatments.

The instructions relating to the use of an EBD antibody or an EDB ADC as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an EDB antibody or EDB ADC. The container may further include a second pharmaceutically active agent.

Kits may optionally provide additional components such as buffers and interpretive information. Normally, the kit includes a container and a label or package insert(s) on or associated with the container.

Dose and Administration

The present invention provides for EDB ADCs administered in an effective dosage. The phrase "effective dosage" or "effective amount" as used herein refers to an amount of an ADC, drug, payload, compound or pharmaceutical composition necessary to achieve any one or more beneficial or desired therapeutic results. For prophylactic use, beneficial or desired results include eliminating or reducing the risk, lessening the severity, or delaying the outset of the disorder, including biochemical, histological and/or behavioral symptoms of the disorder, its complications and intermediate pathological phenotypes presenting during development of the disorder. For therapeutic use, beneficial or desired results include clinical results such as reducing incidence or amelioration of one or more symptoms of various EDB+ FN-expressing disorders, such as cancer, decreasing the dose of other medications required to treat the disorder, enhancing the effect of another medication, and/or delaying the progression of the EDB+ FN-expressing disorders of patients.

An effective dosage can be administered in one or more administrations. An effective dosage of an ADC, drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

For example, when administered to a cancer-bearing subject, an effective amount includes an amount sufficient to elicit anti-cancer activity, including cancer cell cytolysis, inhibition of cancer cell proliferation, induction of cancer cell apoptosis, reduction of cancer cell antigens, delayed tumor growth, and/or inhibition of metastasis. Tumor shrinkage is well accepted as a clinical surrogate marker for efficacy. Another well accepted marker for efficacy is progression-free survival.

The EDB ADCs of the present invention can be administered to an individual via any suitable route. It should be understood by persons skilled in the art that the examples described herein are not intended to be limiting but to be illustrative of the techniques available. Accordingly, in some aspects of the invention, the EDB ADC is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the EDB ADC may be aerosolized using a fluorocarbon formulation and a metered dose inhaler, or inhaled as a lyophilized and milled powder.

In some aspects of the invention, the EDB ADCs are administered via site-specific or targeted local delivery techniques. Examples of site-specific or targeted local delivery techniques include various implantable depot sources of an EDC ADC or local delivery catheters, such as infusion catheters, indwelling catheters, or needle catheters, synthetic grafts, adventitial wraps, shunts and stents or other implantable devices, site specific carriers, direct injection, or direct application.

For the purpose of the present invention, the appropriate dosage of an EDB ADC may depend on the particular EDB ADC (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. The clinician may administer an EDB ADC until a dosage is reached that achieves the desired result and beyond. Dose and/or frequency can vary over course of treatment, but may stay constant as well. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of EDB ADCs may be appropriate. Various formulations and devices for achieving sustained release are known in the art.

For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the disorder, the treatment is sustained until a desired suppression of symptoms occurs or until sufficient therapeutic levels are achieved, for example, to inhibit or delay tumor growth/progression or metastasis of cancer cells. Exemplary dosing regimens may include administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects of the invention, dosing from one to four times a week is contemplated. In other aspects, dosing once a month or once every other month or every three months is contemplated, as well as weekly, bi-weekly and every three weeks. The progress of this therapy may be easily monitored by conventional techniques and assays. The dosing regimen (including the EDB ADC used) can vary over time.

In some aspects of the invention, dosages for an EDB ADC may be determined empirically in individuals who have been given one or more administration(s) of an EDB ADC. Individuals may be given incremental dosages of an EDB ADC. To assess efficacy, an indicator of the disorder can be followed.

Administration of an EDB ADC in accordance with the method in the present invention can be continuous or intermittent, depending, for example, upon the recipient's physiological disorder, whether the purpose of the administration is therapeutic or prophylactic, and other factors known to skilled practitioners. The administration of an EDB ADC may be essentially continuous over a preselected period of time or may be in a series of spaced doses.

Combination Therapies

In some aspects of the invention, the methods described herein further include a step of treating a subject with an additional form of therapy. In some aspects, the additional form of therapy is an additional anti-cancer therapy including, but not limited to, be used in chemotherapy, radiation, surgery, hormone therapy, and/or additional immunotherapy.

The disclosed EDB ADCs may be administered as an initial treatment, or for treatment of cancers that are unresponsive to conventional therapies. In addition, the EDB ADCs may combination with other therapies (e.g., surgical excision, radiation, additional anti-cancer drugs, etc.) to thereby elicit additive or potentiated therapeutic effects and/or reduce cytotoxicity of some anti-cancer agents. EDB ADCs of the invention may be co-administered or co-formulated with additional agents, or formulated for consecutive administration with additional agents in any order.

EDB ADCs of the invention may be used in combination with other therapeutic agents including, but not limited to, therapeutic antibodies, ADCs, immunomodulating agents, cytotoxic agents, and cytostatic agents. Representative agents useful for combination therapy also include any of the drugs described herein above as useful for preparation of an EDB ADC under the subheading "Drugs."

Therapeutic agents include, but are not limited to, the administration of a chemotherapeutic agent, a vaccine, a CAR-T cell-based therapy, radiotherapy, a cytokine therapy, a vaccine, a bispecific antibody, an ADC, an inhibitor of other immunosuppressive pathways, an inhibitors of angiogenesis, a T cell activator, an inhibitor of a metabolic pathway, an mTOR inhibitor, an inhibitor of an adenosine pathway, a tyrosine kinase inhibitor including but not limited to inlyta, ALK inhibitors and sunitinib, a BRAF inhibitor, an epigenetic modifier, an inhibitors or depletor of Treg cells and/or of myeloid-derived suppressor cells, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNa2, GM-CST), and cells transfected with genes encoding immune stimulating cytokines such as but not limited to GM-CSF)

Further representative antibodies, which may be used alone or as an ADC, include, but are not limited to, anti-5T4 antibodies (e.g., A1, A2, and A3), anti-CD19 antibodies, anti-CD20 antibodies (e.g., RITUXAN®, ZEVALIN®, BEXXAR®), anti-CD22 antibodies, anti-antibodies (e.g., MYLOTARG®), anti CD33 antibody-drug conjugates, anti-Lewis Y antibodies (e.g., Hu3S193, Mthu3S193, AGmthu3S193), anti-HER-2 antibodies (e.g., HERCEPTIN® (trastuzumab), MDX-210, OMNITARG® (pertuzumab, rhuMAb 2C4)), anti-CD52 antibodies (e.g., CAMPATH®), anti-EGFR antibodies (e.g., ERBITUX® (cetuximab), ABX-EGF (panitumumab)), anti-VEGF antibodies (e.g., AVASTIN® (bevacizumab)), anti-DNA/histone complex antibodies (e.g., ch-TNT-1/b), anti-CEA antibodies (e.g., CEA-Cide, YMB-1003) hLM609, anti-CD47 antibodies (e.g., 6H9), anti-VEGFR2 (or kinase insert domain-containing receptor, KDR) antibodies (e.g., IMC-1C11), anti-Ep-CAM antibodies (e.g., ING-1), anti-FAP antibodies (e.g., sibrotuzumab), anti-DR4 antibodies (e.g., TRAIL-R), anti-progesterone receptor antibodies (e.g., 2C5), anti-CA19.9 antibodies (e.g., GIVAREX®) and anti-fibrin antibodies (e.g., MH-1).

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan);

bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiM, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-1 1; topoisomerase inhibitor RFS 2000; difluoromethylornithine (DMFO); retinoids such as retinoic acid; capecitabine; and pharmaceutically acceptable salts, acids or derivatives of any of the above.

Also included are anti-hormonal agents that act to regulate or inhibit hormone action on tumors such as antiestrogens and selective estrogen receptor modulators (SERMs), including, for example, tamoxifen, raloxifene, droloxifene, 4-hydroxytamoxifen, trioxifene, keoxifene, LY1 17018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In some aspects, EDB ADCs may be used in combination crizotinib, palbociclib, gemcitabine, cyclophosphamide, fluorouracil, FOLFOX, folinic acid, oxaliplatin, axitinib, sunitinib malate, tofacitinib, bevacizumab, rituximab, and traztuzumab.

In one aspect, after treatment with EDB ADCs an increase in tumor infiltrating lymphocytes, an increase in CD8/CD4 ratios, an increase in F4/80+ macrophages, and/or an increase in immunomodulatory proteins such as PDL1 and 41BB, or any combination thereof, may occur. Thus, the combination of an EDB ADC and an immune checkpoint inhibitor or 10 agent, such as an anti-41BB agonist and/or anti-PDL1 antagonist monoclonal antibody may be effective. (See Example 12). Further, EDB ADCs of the invention alone may have immunomodulatory, and immune-oncology (10) agent enabling mechanisms, that maybe increased with combination therapy.

In some aspects, an EDB ADC may be used in combination with one or more other therapeutic agents targeting an immune checkpoint modulator, including but not limited to, an agent (such as an antibody) targeting PD-1, PD-L1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD1 12, LAIR1, 2B4, BTLA, CD160, TIM1, TIM-3, TIM4, VISTA (PD-H1), OX40, OX40L, GITR, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAM1-15, PSG1-1 1, CEACAM1-4C1, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator.

For combination therapies, an EDB ADC and/or one or more additional therapeutic agents are administered within any time frame suitable for performance of the intended therapy. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

The disclosed combination therapies may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater.

A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

EXAMPLES

The following examples of specific aspects for carrying out the present invention are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Generation of Anti-EDB Antibodies and Preparation for Conjugation

Generation of Anti-EDB Antibodies

The cDNA encoding various fully human antibodies that bind to EDB were constructed using standard molecular biology methodology and derived from the L19 human monoclonal antibody which specifically binds to EDB (herein after "anti-EDB-L19" or "EDB-L19" antibody). The EDB-L19 antibody comprises a human IgG1 constant region with Glm(a) allotype having aspartic acid (D) at position 356 and leucine (L) at position 358 (according to the EU index of Kabat) and a human Kappa light chain constant region. The EDB-L19 antibody heavy and light chain variable regions are set forth in SEQ ID NOS. 1 and 10, respectively, and the heavy and light chains are set forth in SEQ ID NOS. 8 and 15, respectively.

To produce a non-immunogenic antibody, a non-Glm(a) allotype having glutamic acid (E) at position 356 and methionine (M) at position 358 (according to the EU index of Kabat) was introduced into the EDB-L19 heavy chain. To generate the heavy chain, the nucleotide sequence encoding the EDB-L19 heavy chain variable region was fused to the human IgG1 constant region cDNA with the Glm$^z$, non-(a), non-(x) allotype. In some aspects, the antibodies were further altered to decrease the charge variant of an antibody and increase homogeneity by eliminating the C-terminal lysine (K) of the EDB-L19 antibody IgG1 constant region generating EDB-PFE HC (SEQ ID NO: 17). The EDB-PFE antibody heavy and light chains are set forth in SEQ ID NOS. 17 and 15, respectively.

As shown in Table 4, imaged capillary electrophoresis (iCE) was performed using an iCE3 with Prince Autosampler to determine the percent of charge variants for the antibody preparations. The EDB-L19 antibody had a substantial increase in basic species and a decrease of the main peak of antibody as a result of incomplete C-terminal lysine processing during cell culture compared to the EDB-PFE antibody.

TABLE 4

Percent (%) of charge variants for EDB antibodies.

| EDB Antibody | % Acidic | % Main | % Basic |
|---|---|---|---|
| EDB-L19 Ab (HC with C-terminal Lys) | 19.60 | 49.44 | 30.96 |
| EDB-PFE Ab (HC without C-terminal Lys) | 23.16 | 71.92 | 4.92 |

Antibodies for Site-Specific Conjugation Via Engineered Cysteine Residues

Methods for preparing anti-EDB antibodies for site-specific conjugation to various linker-payloads through reactive engineered cysteine residues were generally performed as described in PCT International Publication No. WO2013/093809, which is incorporated herein by reference in its entirety. One or more residues on either the heavy chain, such as position K290 (according to the EU index of Kabat, or the light chain, such as K183 (according to Kabat) were altered to a cysteine (C) residue by site directed mutagenesis.

In some aspects, position K290 (according to the EU index of Kabat) in the human IgG1 heavy chain constant region of the EDB-PFE antibody was substituted with a reactive cysteine (C) to enable site-specific conjugation generating EDB-(K290C) HC (SEQ ID NO: 19). In other aspects, residue K183 (according to Kabat) in the human Kappa light chain constant region was substituted to a reactive cysteine (C) to enable site-specific conjugation generating EDB-(κK183C) LC (SEQ ID NO: 31).

Antibodies for Site Specific Conjugation Via Engineered Glutamine Residues

Anti-EDB antibodies were expressed having human IgG1 subtypes engineered with reactive glutamine residues, such as glutamine-containing ("Q") tags, at various amino acid positions for conjugation to various linker-payloads. Methods for preparing anti-EDB antibodies for site-specific conjugation through reactive glutamine residues were generally performed as described in PCT International Publication WO2012/059882, which is incorporated herein by reference in its entirety.

In some aspects, a H16-glutamine tag LLQG (SEQ ID NO: 40) was engineered within the human IgG1-Fc region of the EDB-PFE antibody to enable a DAR 2 transglutaminase mediated site-specific conjugation. For example, in the EDB-PFE antibody heavy chain the amino acids at positions E294-N297 (according to the EU index of Kabat) were replaced with the H16-glutamine-containing tag LLQG (SEQ ID NO: 40). In other aspects, the antibodies were further altered to increase specificity of conjugation to the engineered H16-glutamine-containing tag. The lysine (K) amino acid at position 222 (according to the EU index of Kabat) on the heavy chain was substituted with an arginine (R) generating EDB-(H16-K222R) HC (SEQ ID NO: 27). The K222R substitution provided an increase in homogenous ADCs, improved intermolecular crosslinking between the antibody and linker-payload, and/or significant decrease in interchain crosslinking with the H16-glutamine-containing tag on the C-terminus of the antibody light chain.

Potential Chemical Liabilities

Potential chemical liabilities, especially within CDRs, may impact molecular heterogeneity and result in antigen binding a putative protein glycation sites. Protein glycation is a non-enzymatic glycosylation that can occur in recombinant antibodies during cell culture and glycated proteins can undergo further reactions to generate poorly characterized heterogeneous products, collectively termed advanced glycation end products. To mitigate potential glycation liability, position K94 (numbering of Kabat) adjacent to CDR3 in the EDB-L19 heavy chain variable region was mutated to an arginine (R) to generate EDB-(K94R) VH (SEQ ID NO: 21) and was then fused to a human IgG1 constant region to generate EDB-(K94R) HC (SEQ ID NO: 23). The K94R glycation mutation was also introduced within the EDB-(K290C) and EDB-(H16-K222R) heavy chains engineered for site-specific conjugation to generate EDB-(K94R-K290C) HC (SEQ ID NO: 25) and EDB-(K94R-H16-K222R) HC (SEQ ID NO: 29), respectively.

Example 2

Characterization of EDB Antibody Variant Binding Properties

Binding Affinity Analysis

Surface plasmon resonance (SPR) was used to characterize binding kinetics of the anti-EDB antibody variants to recombinant human, cynomolgus monkey and rat 7-EDB-89 (SEQ ID NO: 34, SEQ ID NO: 35 and SEQ ID NO: 36, respectively) and to confirm that binding properties of the anti-EDB antibodies having the K94R glycation mutation were fully retained. Binding is detected by surface SPR of laser light refracting from the surface. Analysis of the signal kinetics on-rate (ka) and off-rate (kd), allows the discrimination between non-specific and specific interactions.

An anti-human IgG antibody (GE Healthcare) was covalently amine coupled onto all 4 flow cells of a CM5 carboxymethylated dextran coated sensor chip to a density of about 10,000 resonance units (RUs) following the manufacturer's protocol and then each anti-EDB antibody variant was captured to a level of approximately 60-90 RUs. The running and sample buffer used was HBS-EP+ buffer (0.01M HEPES, 0.15M NaCl, 3 mM EDTA, and 0.05% v/v surfactant P20 pH7.4). A 3-fold serial dilution series of 7-EDB-89 ranging in concentration from 600 nM to 11.1 nM was injected over the surface at a flow rate of 50 μL/minute for a 60 second association and 120 second dissociation. The surface was then regenerated with a 30 second pulse of 3M MgCl$_2$, a 30 second pulse of an ionic regeneration buffer (0.46M KSCN, 1.83 M MgCl$_2$, 0.92 M urea, and 1.83 M guanidine-HCl pH7.4) and then equilibrated with a 30 second pulse of HBS-EP+ running buffer. All SPR assays were performed at 25° C. with a data collection rate of 1 Hz using a BIACORE® (Cytiva; surface plasmon resonance (SPR) system) T200 instrument (GE Healthcare). The resulting sensorgrams were double referenced (Myszka, D. G., J. Mol. Recognit., 12:279-284, 1999) using both a control surface and buffer injections. The rate constants were determined by fitting the data to a 1:1 Langmuir model with BIACORE® (Cytiva; surface plasmon resonance (SPR) system) T200 evaluation software v2.0 and the equation $K_D=k_d/k_a$. Each experiment was run in duplicate and the average $K_D$ was determined. As shown in Table 5, the EDB-L19 and EDB-(K94R) antibodies exhibit comparable binding to human 7-EDB-89. t½=half-life, Rmax=maximum response, RU=resonance units.

TABLE 5

Binding properties of EDB-L19 and EDB-(K94R) antibodies.

| 7-EDB-89 | Antibody | ka (1/Ms) | kd(1/s) | t½ (s) | Rmax (RU) | Chi2/Rmax | $K_D$ (nM) |
|---|---|---|---|---|---|---|---|
| Human (1) | EDB-L19 | 5.03E+05 | 1.16E−01 | 5.97 | 61.7 | 0.24% | 230 |
| Human (2) | EDB-L19 | 4.86E+05 | 1.13E−01 | 6.13 | 61.5 | 0.20% | 232 |
| | | | | | | | 231 ± 1.4 Avg ± SD |
| Human (1) | EDB-(K94R) | 5.39E+05 | 1.24E−01 | 5.59 | 36.4 | 0.08% | 230 |
| Human (2) | EDB-(K94R) | 5.02E+05 | 1.13E−01 | 6.13 | 35.1 | 0.17% | 226 |
| | | | | | | | 228 ± 2.8 Avg ± SD |

Further, the binding affinities of EDB-L19 and EDB-(κK183C-K94R-K290C) antibodies to human, cynomolgus monkey and rat 7-EDB-89 were determined. As show in Table 6, the binding affinities of the EDB-L19 and EDB-(κK183C-K94R-K290C) were antibodies were similar. As show in Table 7, the binding affinities of EDB-(κK183C-K94R-K290C) antibody to human, cynomolgus monkey and rat 7-EDB-89 were comparable confirming cross-species reactivity was retained after engineering EDB-L19 antibody to enable site-specific conjugation and removal of putative glycation site.

TABLE 6

Binding properties of anti-EDB antibodies 7-EDB-89.

| | EDB-L19 antibody | | | EDB-(κK183C-K94R-K290C) | | |
|---|---|---|---|---|---|---|
| 7-EDB-89 | ka (1/Ms) | kd (1/s) | KD (nM) | ka (1/Ms) | kd (1/s) | KD (nM) |
| Human | 6.15E+05 | 9.75E−02 | 159 | 1.40E+06 | 3.12E−01 | 223 |
| Monkey | 5.60E+05 | 1.05E−01 | 188 | ND | ND | ND |
| Rat | 5.08E+05 | 1.07E−01 | 210 | ND | ND | ND |

TABLE 7

Binding properties of EDB-(κK183C-K94R-K290C) antibody to 7-EDB-89.

| 7-EDB-89 | Antibody | ka (1/Ms) | kd(1/s) | t½ (s) | Rmax (RU) | Chi2/Rmax | $K_D$ (nM) |
|---|---|---|---|---|---|---|---|
| Human | EDB-(κK183C-K94R-K290C) | 3.42E+05 | 1.16E−01 | 6.0 | 67.0 | 0.20% | 340.0 |

TABLE 7-continued

Binding properties of EDB-(κK183C-K94R-K290C) antibody to 7-EDB-89.

| 7-EDB-89 | Antibody | ka (1/Ms) | kd(1/s) | t½ (s) | Rmax (RU) | Chi2/Rmax | $K_D$ (nM) |
|---|---|---|---|---|---|---|---|
| Cyno monkey | EDB-(κK183C-K94R-K290C) | 3.30E+05 | 1.19E−01 | 5.8 | 62.6 | 0.29% | 361.5 |
| Rat | EDB-(κK183C-K94R-K290C) | 2.98E+05 | 1.23E−01 | 5.7 | 62.1 | 0.31% | 412.5 |

Competitive Binding by ELISA

Binding properties of EDB-(K94R) and EDB-(κK183C-K94R-K290C) antibodies were further evaluated using a competition ELISA with biotinylated EDB-L19 to confirm binding to EDB was fully maintained. Human 7-EDB-89 (SEQ ID NO: 34) was immobilized (100 ng/well) onto a 96-well ELISA plate and 20 ng/mL biotinylated EDB-L19 antibody was added to compete with varying concentrations of the modified anti-EDB antibody samples and binding was detected using an anti-Streptavidin-HRP antibody (Southern Biotech, Birmingham, AL).

Figure 1A:
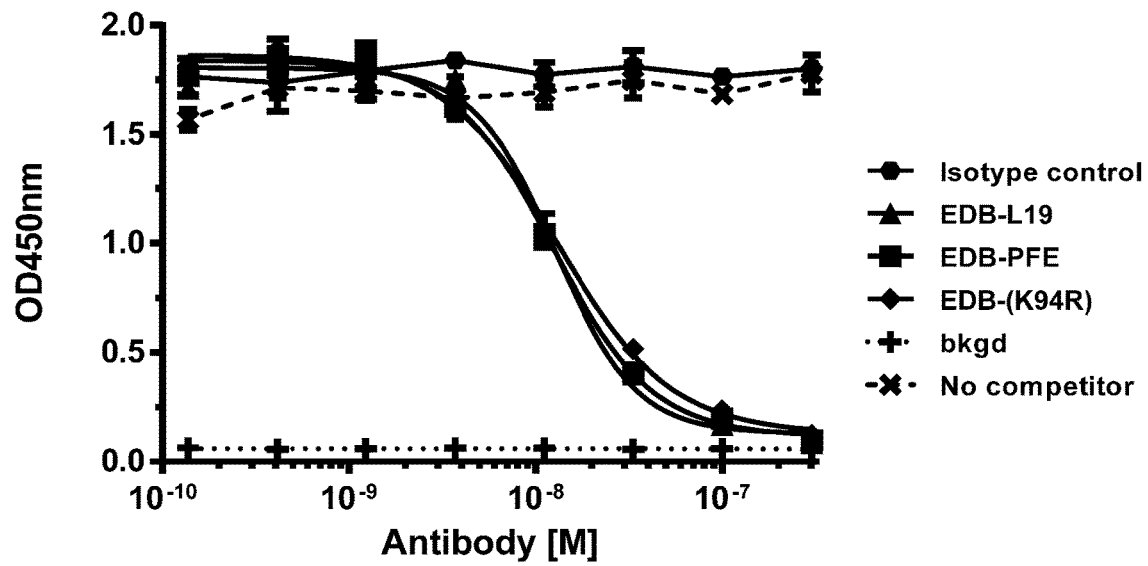
FIGS. 1A and 1B show binding properties of [A] EDB-L19, EDB-PFE and EDB-(K94R) antibodies; and [B] EDB-(K94R) and EDB-(κK183C-K94R-290C) antibodies.
Figure 1B:
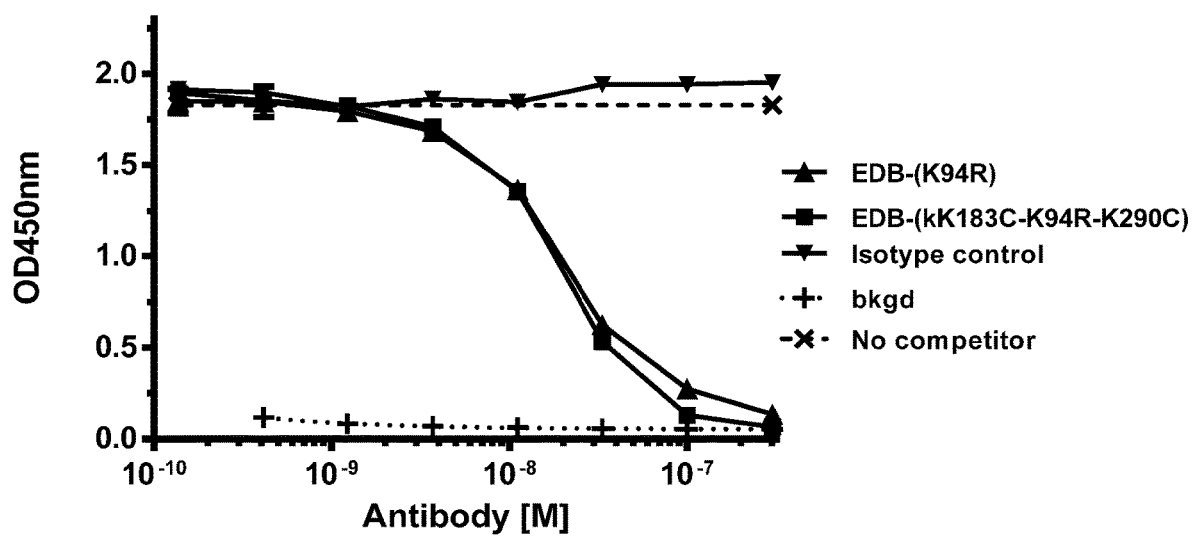

As shown in FIG. 1A and Table 8, the EDB-L19 and EDB-(K94R) antibodies had similar half maximal inhibition concentration values. FIG. 1B and Table 9 show that the EDB-(K94R) and EDB-(κK183C-K94R-K290C) antibodies also had similar half maximal inhibition concentration values. This indicates that the EDB-(K94R) and EDB-(κK183C-K94R-K290C) modified antibodies retained EDB binding properties and that the (K94R) modification of the heavy chain and/or the introduction of reactive engineered cysteines for site-specific conjugation did not alter binding to EDB.

TABLE 8

Competition with bioEDB-L19 for binding to human 7-EDB-89.

| Antibody | IC50 [nM] |
|---|---|
| EDB-L19 | 12.7 |
| EDB-(K94R) | 13.1 |

TABLE 9

Competition with bioEDB-L19 for binding to human 7-EDB-89.

| Antibody | $IC_{50}$ [nM] |
|---|---|
| EDB-(K94R) | 19.7 |
| EDB-(κK183C-K94R-K290C) | 19.0 |

Avidity Analysis

The affinity for EDB-L19 antibody binding EDB was determined to be a low binding interaction at ~230 nM. Therefore, SPR was used to investigate whether avidity impacted binding to differential target levels within the tumor microenvironment. Varying densities of human 7-EDB-89 (SEQ ID NO: 34) were covalently amine coupled onto individual flow cells of a CM5 carboxymethylated dextran coated sensor chip. The running and sample buffer was as described above for the binding affinity analysis. A 3-fold serial dilution series of EDB-L19 antibody ranging in concentration from 6 nM to 0.074 nM was injected at a flow rate of 50 μL/minute for a 110 second association and 900 second dissociation. The surface was then regenerated with two 30 second pulse of an ionic regeneration buffer (0.46M KSCN, 1.83 M $MgCl_2$, 0.92 M urea, and 1.83 M guanidine-HCl pH7.4) and then equilibrated with a 30 second pulse of HBS-EP+ running buffer. Each experiment was run in duplicate and the average ka, kd and $K_D$ was determined.

As shown in Table 10, the results showed that as the level of immobilized human 7-EDB-89 increased, the off-rates (kd) slowed and subsequent affinities were increased. The apparent $K_D$ values were proportional to the immobilization levels of human 7-EDB-89 and confirmed that EDB-L19 antibody binds EDB with a large avidity component.

TABLE 10

Apparent $K_D$ Values of EDB Antibody Binding EDB.

| Analyte | Ligand | ka (1/Ms) | kd(1/s) | t½ (min) | Rmax (RU) | Chi2/Rmax | KD (pM) |
|---|---|---|---|---|---|---|---|
| EDB-L19 | 7-EDB-89 High: 650 RU | 4.34E+06 | 2.06E−04 | 3364.1 | 194.8 | 4.77% | 47.4 |
| EDB-L19 | 7-EDB-89 High: 650 RU | 4.42E+06 | 1.72E−04 | 4029.1 | 187.7 | 0.73% | 38.8 |
| | AVG ± STD | 4.38E+06 | 1.89E−04 | | | | 43.1 ± 6.08 |

TABLE 10-continued

Apparent $K_D$ Values of EDB Antibody Binding EDB.

| Analyte | Ligand | ka (1/Ms) | kd(1/s) | t½ (min) | Rmax (RU) | Chi2/Rmax | KD (pM) |
|---|---|---|---|---|---|---|---|
| EDB-L19 | 7-EDB-89 Med: 90 RU | 4.46E+06 | 8.83E−04 | 784.8 | 38.9 | 2.20% | 198 |
| EDB-L19 | 7-EDB-89 Med: 90 RU | 2.71E+06 | 4.53E−04 | 1529.8 | 40.6 | 2.54% | 167 |
| | AVG ± STD | 3.59E+06 | 6.68E−04 | | | | 182.5 ± 21.9 |
| EDB-L19 | 7-EDB-89 Low: 50 RU | 2.02E+06 | 1.13E−03 | 613.3 | 27.5 | 9.49% | 557 |
| EDB-L19 | 7-EDB-89 Low: 50 RU | 2.81E+06 | 7.65E−04 | 905.9 | 23.6 | 2.06% | 272 |
| | AVG ± STD | 2.42E+06 | 9.48E−04 | | | | 414.5 ± 201.5 |

Polyreactivity of Anti-EDB Antibodies

Polyreactivity has been associated with rapid clearance in vivo (Hotzel et al. mAbs 4(6):753-760, 2012) and undesirable protein-protein interactions (Xu et al. Protein Eng Des Sel 26(10): 663-670 (2013). A DNA and Insulin direct binding ELISA has been shown to correlate with known pharmacokinetics (PK) of clinically validated antibodies. Serial dilutions of antibodies starting at 10 ng/mL in quadruplicate were assessed in a low stringency assay for binding to either DNA or Insulin that was directly coated onto an ELISA plate.

As shown in Table 11, both the EDB-(K94R) and the EDB-(κK183C-K94R-K290C) antibodies have very low polyreactivity scores that are comparable or better than the negative control which has optimal PK properties. Further, the polyreactivity scores were significantly lower than the positive control antibody having poor PK and resulting in rapid clearance.

TABLE 11

Polyreactivity Scores of anti-EDB antibodies.

| | Polyreactivity Score | |
|---|---|---|
| Antibody | DNA | Insulin |
| Negative Control | 4.805 | 5.027 |
| Positive Control | 15.741 | 12.171 |
| EDB-(K94R) | 0.429 | 2.725 |
| EDB-(κK183C-K94R-K290C) | 0.412 | 4.267 |

FcRn Chromatography

FcRn chromatography was utilized to investigate potential charge-mediated influence of the introduction of reactive engineered cysteines into a wild type IgG1 constant region on FcRn-dependent pharmacokinetics. Evaluation of antibodies using FcRn column methodology has demonstrated that the elution time exhibited a positive correlation with human and non-human primate clearance (Schoch A. et al. PNAS, 2015, Vol. 112). FcRn affinity columns were prepared according to Schlothauer et al., MAbs 5(4): 576-586, 2013. Next, 50 µg of EDB-(κK183C-K94R-K290C) antibody or EDB-(κK183C-K94R-K290C)-vc-0101 ADC was injected and then eluted by a linear pH gradient (30 CV) from pH 5.5-8.8 within 60 minutes using 20 mM MES, 150 mM NaCl, pH5.5 and 20 mM Tris, 150 mM NaCl, pH 8.8 as eluents.

As shown in Table 12, the FcRn column relative elution time of the EDB-(κK183C-K94R-K290C) antibody and EDB-(κK183C-K94R-K290C)-vc-0101 ADC were consistent with acceptable PK parameters. These data demonstrate that the incorporation of reactive engineered cysteine residue K290 into the IgG1 constant region does not impact FcRn binding.

TABLE 12

FcRn column relative elution time.

| Antibody or ADC | FcRn Relative Elution time (min) | Peak Width at 50% Height |
|---|---|---|
| EDB-(κK183C-K94R-K290C) | 0.62 | 1.19 |
| EDB-(κK183C-K94R-K290C)-vc-0101 | 2.00 | 1.57 |

Example 3

Bioconjugation of EDB ADCs

Anti-EDB antibodies of the present invention were conjugated to drugs/payloads via linkers to generate EDB ADCs. The conjugation method used was either conventional conjugation (i.e. via random cysteine residues) or site-specific conjugation (i.e., via engineered cysteine residues or engineered glutamine residues). Table 13 shows the conjugation methods used for various EDB ADCs.

Method A: Conventional Conjugation Via Cysteine Residues

Anti-EDB antibody at 27 mg/ml in PBS, pH7.2 was reduced with 2.3 to 2.6 times (m/m) of TCEP at 37° C. for 2 hours and then conjugated. Molar ratio was generally at 2.5 times but optimized depending on the amount of antibody conjugate to achieve an optimal final average DAR of about 4.0. The partially reduced antibody conjugated with 6 to 7 times (m/m) of linker-payload in PBS with 10% DMA at 25° C. for 1 hour. Excess linker-payload was quenched with L-cysteine at 25° C. for 15 minutes. The crude ADC was dialyzed overnight in PBS at 4-6° C.

The crude ADC was purified by size exclusion chromatography (SEC) on SUPERDEX® 200 (Cytiva; gel filtration media) in PBS and collected monomer peak was either stored at 4-6° C. or dialyzed in 20 mM histidine, 8.5% sucrose, pH 5.8; sterile filtered and frozen at −70° C. Negative control huNeg-8.8 antibody was conjugated by the same method.

Method B: Site-Specific Conjugation Via Engineered Cysteine Residues

Two grams anti-EDB antibody, generated with reactive engineered cysteine residues, at 27.2 mg/ml in PBS, pH7.2 was reduced with 15 times (m/m) of TCEP at 37° C. for 7 hours and desalted on SEPHADEX® G-25 (Cytiva; gel filtration media) in PBS to remove excess TCEP. The inter-chain cysteines were oxidized with 30 times DHA (m/m) at 4-6° C. overnight. DHA was removed by desalting on SEPHADEX® G-25 (Cytiva; gel filtration media) in PBS. For ADC having a higher degree of glutathione capping, instead of the preferred cysteine capping of the site-specific cysteine, 100 times TCEP (m/m) was used for reduction.

The reduced and oxidized antibody was conjugated with 9 times (m/m) of linker-payload in PBS with 10% DMA at 25° C. for 2 hours. Excess linker-payload was quenched with 9 times (m/m) of L-cysteine at 25° C. for 15 minutes. The crude ADC was dialyzed overnight in PBS at 4-6° C.

The crude ADC was purified by SEC on SUPERDEX® 200 (Cytiva; gel filtration media) in PBS and collected monomer peak was dialyzed in 20 mM histidine, 8.5% sucrose, pH 5.8; sterile filtered and frozen at −70° C. Negative control huNeg-8.8 antibody was conjugated by the same method.

Method C: Site-Specific Conjugation Via Engineered Glutamine Residues

Anti-EDB antibody, generated with reactive engineered glutamine residues, was dialyzed in the reaction buffer; 100 mM phosphate, 200 mM NaCl, pH 7.0. 20 mg/ml of antibody was conjugated to linker-payload (10 times m/m) at room temperature for 15 hours, using 1 unit of commercial purified transglutaminase (TG) per mg of antibody, with mixing, in 100 mM potassium phosphate, 200 mM NaCl, 10% DMSO. The crude ADC was centrifuged and the supernatant was purified by SEC.

The crude ADC was purified by SEC on SUPERDEX® 200 (Cytiva; gel filtration media) in PBS, collected monomer peak was and dialyzed in 20 mM histidine, 8.5% sucrose, pH 5.8; sterile filtered and frozen at −70° C. Negative control huNeg-8.8 antibody was conjugated by the same method.

Method D: Conventional Conjugation Via Cysteine Residues Using Disulfide Linkers Anti-EDB antibody at 27 mg/ml in PBS, pH7.2 was partially reduced using 5 times (m/m) of TCEP at 37° C. for 2 hours and desalted using a SEPHADEX® G-25 (Cytiva; gel filtration media) SEC.

The partially reduced antibody was conjugated with 12-15 times (m/m) of reduced linker-payload in 67 mM HEPES, pH7.0 with 0.7 mM DTPA and 7% DMA at 25° C. for 15 minutes. Excess linker-payload was quenched with 20 times NEM (m/m) at 25° C. for 15 minutes.

The crude ADC was purified by SEC on SUPERDEX® 200 (Cytiva; gel filtration media) in PBS with 50 mM DHA and 50 mM DTPA, and collected monomer peak which was stored at 4-6° C. A negative control was conjugate by the same method.

TABLE 13
Structures of various EDB ADCs (X represents an antibody).
| ADC# | ADC | Structure | Method |
|---|---|---|---|
| ADC1 | EDB-L19-vc-0101 | 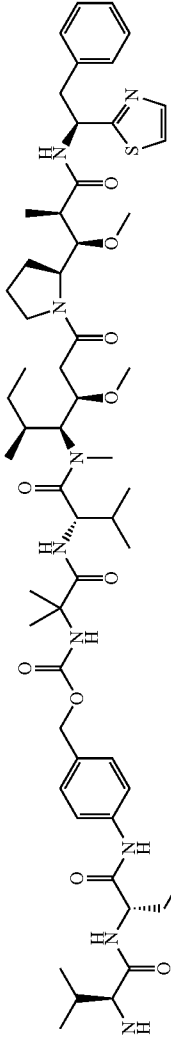 | A |
| ADC2 | EDB-(κK183C-K290C)-vc-0101 | 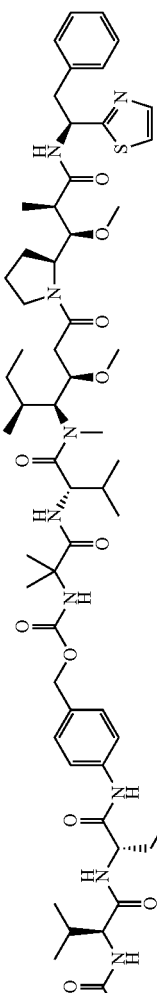 | B |
| ADC3 | EDB-(K94R)-vc-0101 | 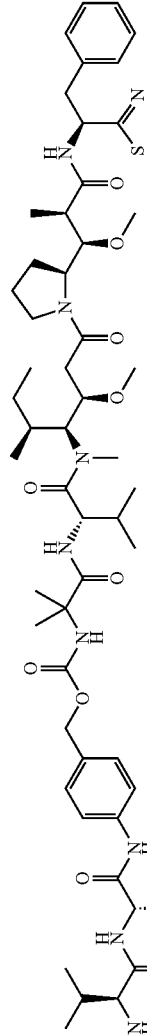 | A |

TABLE 13-continued

Structures of various EDB ADCs (X represents an antibody).

| ADC# | ADC | Structure | Method |
|---|---|---|---|
| ADC4 | EDB-(κK183C-K94R-K290C)-vc-0101 | 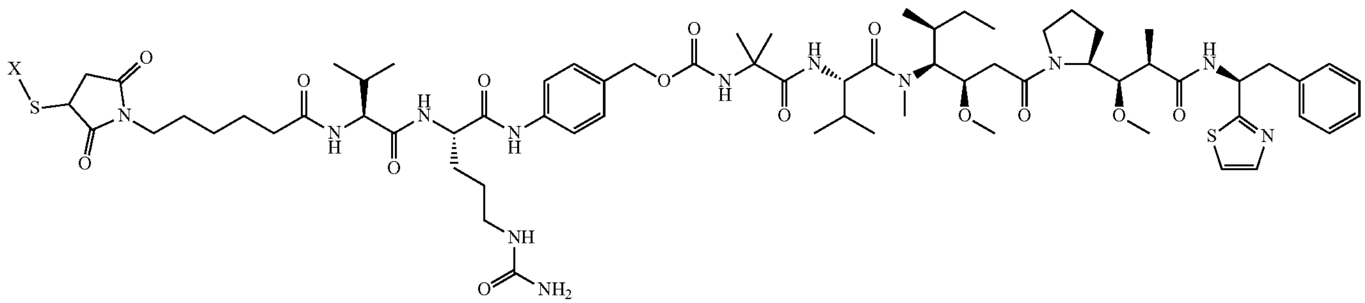 | B |
| ADC5 | EDB-L19-diS-DM1 | 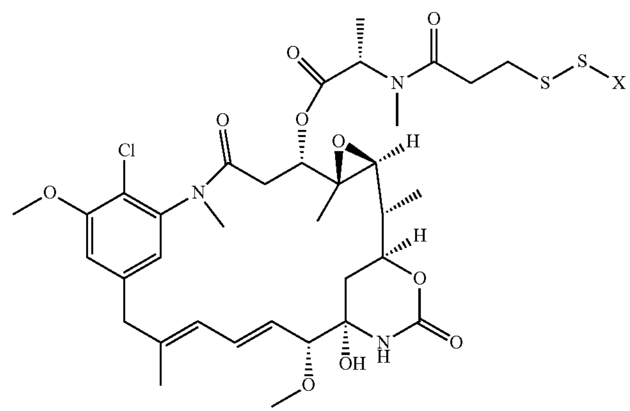 | D |
| ADC6 | EDB-L19-diS-C₂OCO-1569 | 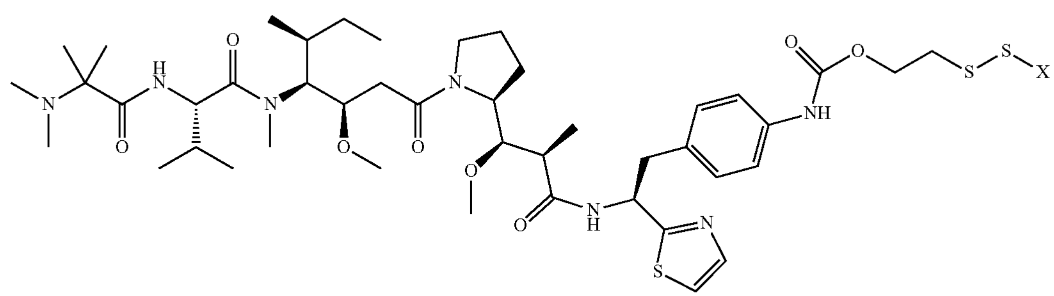 | D |

TABLE 13-continued

Structures of various EDB ADCs (X represents an antibody).

| ADC# | ADC | Structure | Method |
|---|---|---|---|
| ADC7 | EDB-L19-vc-9411 | 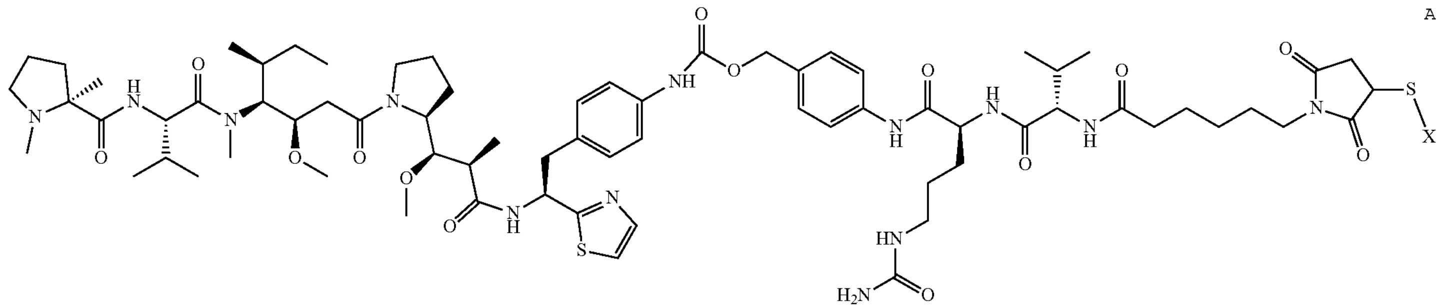 | A |
| ADC8 | EDB-diS-L19-4574 | 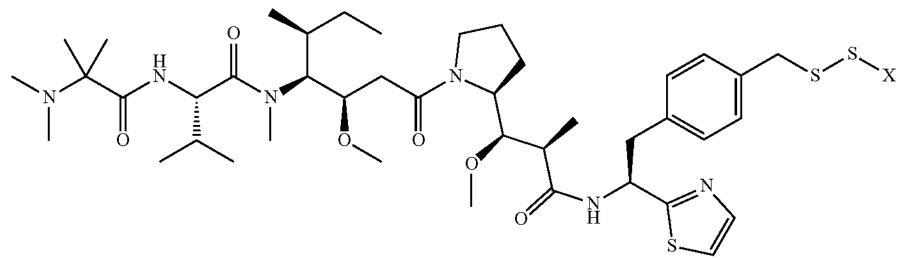 | D |

TABLE 13-continued
Structures of various EDB ADCs (X represents an antibody).
| ADC# | ADC | Structure | Method |
|---|---|---|---|
| ADC9 | EDB-(H16-K222R)-AcLys-vc-CPI-8314 | 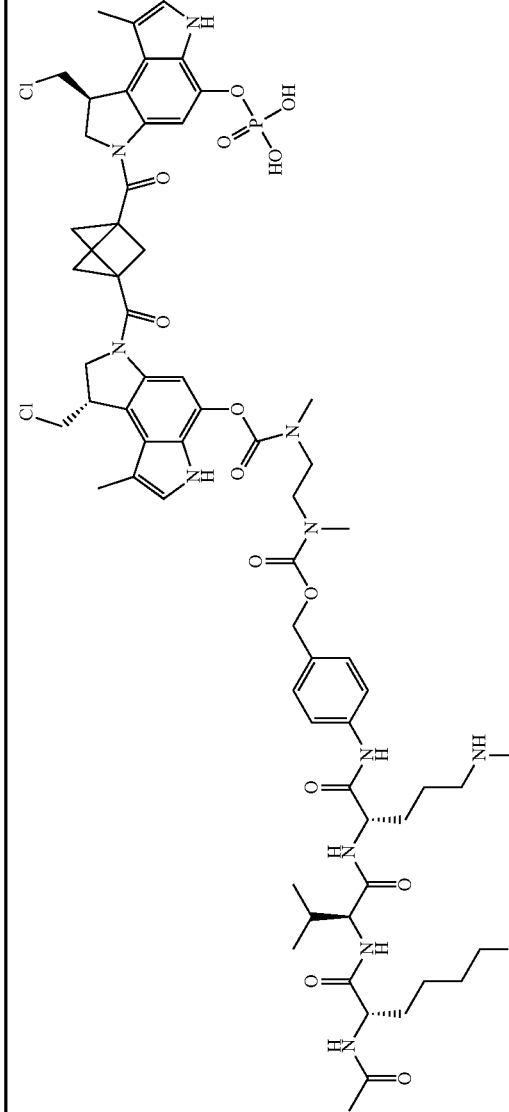 | C |
| ADC10 | EDB-L19-vc-1569 | 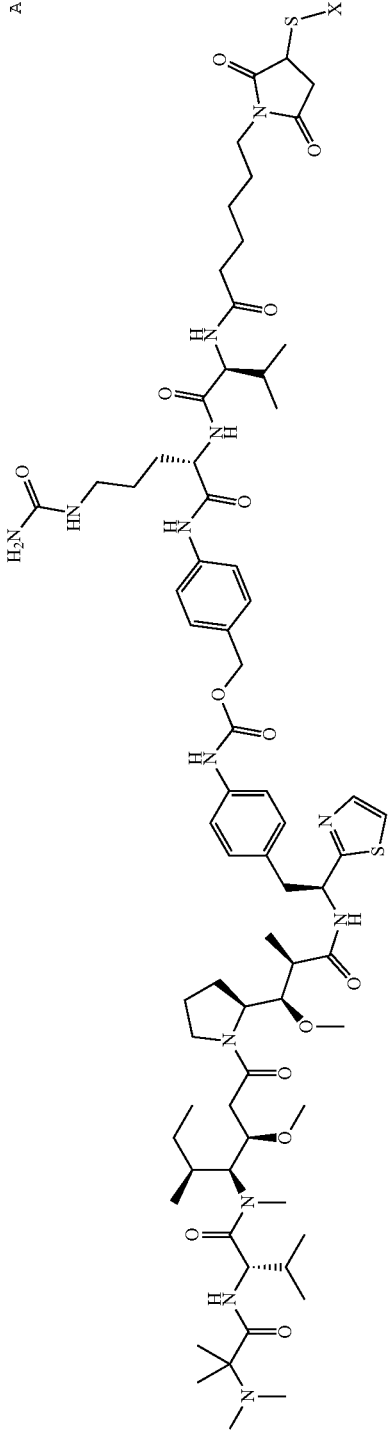 | A |

Example 4

Characterization of EDB ADCs

The EDB ADCs of the present invention were characterized using a combination of size-exclusion chromatography (SEC), LC-MS and hydrophobic interaction chromatography (HIC). The average drug:antibody ratio (DAR) was determined by a mass spectrometry (MS). Table 14 provides analytic characteristics of various EDB ADCs.

LC-MS: Column=Waters BEH300-C4, 2.1×100 mm (P/N=186004496); Instrument=ACQUITY® UPLC (Waters Technologies Corporation, ultra performance liquid chromatography instrument) with an SQD2 mass spec detector; Flow rate=0.7 mL/min; Temperature=80° C.; Buffer A=water+0.1% formic acid; Buffer B=acetonitrile+0.1% formic acid. The gradient runs from 3% B to 95% B over 2 minutes, holds at 95% B for 0.75 min, and then re-equilibrates at 3% B. The sample is reduced with TCEP or DTT immediately prior to injection. The eluate is monitored by LCMS (400-2000 daltons) and the protein peak is deconvoluted using MaxEnt1. DAR is reported as a weight average loading as has been previously described.

SEC: Column: SUPERDEX® 200 (Cytiva; gel filtration media) (5/150 GL); Mobile phase: Phosphate buffered saline containing 2% acetonitrile, pH 7.4; Flow rate=0.25 mL/min; Temperature=ambient; Instrument: Agilent 1100 HPLC.

HIC: Column: TSKGel Butyl NPR, 4.6 mm×3.5 cm (P/N=S0557-835); Buffer A=1.5 M ammonium sulfate containing 10 mM phosphate, pH 7; Buffer B=10 mM phosphate, pH 7+20% isopropyl alcohol; Flow rate=0.8 mL/min; Temperature=ambient; Gradient=0% B to 100% B over 12 minutes, hold at 100% B for 2 minutes, then re-equilibrate at 100% A; Instrument: Agilent 1100 HPLC.

Example 5

EDB+ FN Expression

To conduct a broad investigation of cancer indications for EDB ADC based therapy, EDB+ FN expression was analyzed at the protein and mRNA level in human tumors and PDX models.

RNA-Seq Analysis of EDB+ FN Expression

RNA-Seq data was analyzed from 10660 individual tumor samples collected as part of The Cancer Genome Atlas (TCGA) project (National Cancer Institute at HIH, Bethesda, MD) expanding 31 tumor types. The isoform level expression data were obtained from OmicSoft software (Cary, NC). EDB+ FN expression was calculated as the summation of expression levels of the isoforms of fibronectin (FN1) which harbor EDB. The expression levels were measured by fragment per kilobase of transcript per million reads (FPKM) and the summary statistics of EDB+ FN expression levels for each tumor type is shown in Table 15. Generally, the gene is considered expressed if the FPKM is about 1 or higher.

Table 15 shows the RNA-Seq analysis of EDB+ FN in human tumors. EDB+ FN expression is demonstrated in a broad range of human tumor indications, including but not limited to, thyroid carcinoma, sarcoma, breast carcinoma, pancreatic adenocarcinoma, glioblastoma, cholangiocarcinoma, lung adenocarcinoma, renal carcinoma, melanoma, uterine carcinosarcoma, mesothelioma, lung squamous cell carcinoma, rectum and colon adenocarcinoma, liver hepatocellular carcinoma, colon carcinoma, ovariam serous cystadenocarcinoma, and bladder carcinoma.

TABLE 14

Analytical characteristics of EDB ADCs.

| ADC# | ADC | Isolated yield (%) | HPLC-HIC retention time | Observed Δ mass for HC | DAR (LC/MS Method) | DAR (HIC Method) |
|---|---|---|---|---|---|---|
| ADC1 | EDB-L19-vc-0101 | 64 | 8.7 | 1342 | 3.4 | 3.4 |
| ADC2 | EDB-(κK183C-K290C)-vc-0101 | 63 | 8.9 | 1341 | 3.8 | 4.0 |
| ADC3 | EDB-(K94R)-vc-0101 | 65 | 8.6 | 1342 | 3.7 | 4.1 |
| ADC4 | EDB-(κK183C-K94R-K290C)-vc-0101 | 71 | 8.9 | 1341 | 3.8 | 3.9 |
| ADC5 | EDB-L19-diS-DM1 | 80 | 8.9 | 738 | 4.4 | 4.9 |
| ADC6 | EDB-L19-diS-C$_2$OCO-1569 | 84 | 6.4 | 889.6 | 4.4 | 4.7 |
| ADC7 | EDB-L19-vc-9411 | 80 | 8.3 | 1397 | 5.3 | 4.9 |
| ADC8 | EDB-L19-diS-4574 | 75 | 6.5 | 816 | 5.2 | 5.2 |
| ADC9 | EDB-(H16-K222R)-AcLys-vc-CPI-8314 | 78 | 5.2 | 1343 | 2.0 | 1.7 |
| ADC10 | EDB-L19-vc-1569 | 82 | 7.4 | 1385 | 4.3 | 4.2 |

TABLE 15

RNA-Seq analysis of EDB+ FN in TCGA samples.

| Tumor type/disease | Medium Value (FPKM) | Upper Quantile | Lower Quantile | Maximum Value |
|---|---|---|---|---|
| Thyroid carcinoma | 216.69 | 628.03 | 14.20 | 3541.43 |
| Sarcoma | 96.86 | 226.41 | 22.20 | 1450.21 |
| Breast invasive carcinoma | 36.92 | 77.75 | 14.77 | 1062.56 |
| Pancreatic adenocarcinoma | 35.08 | 67.03 | 14.02 | 549.68 |
| Glioblastoma multiforme | 28.74 | 56.74 | 11.76 | 1171.19 |
| Cholangiocarcinoma | 27.77 | 55.99 | 10.34 | 458.05 |
| Lung adenocarcinoma | 23.31 | 49.16 | 10.85 | 1105.41 |
| Kidney renal clear cell carcinoma | 22.91 | 39.34 | 11.49 | 346.83 |
| Skin Cutaneous Melanoma | 22.13 | 54.48 | 7.89 | 2131.95 |
| Uterine Carcinosarcoma | 21.08 | 56.70 | 7.28 | 185.43 |
| Mesothelioma | 20.13 | 52.36 | 3.64 | 205.08 |
| Lung squamous cell carcinoma | 19.13 | 42.86 | 8.75 | 1004.73 |
| Rectum adenocarcinoma | 15.69 | 33.20 | 6.02 | 221.89 |
| Liver hepatocellular carcinoma | 13.29 | 37.22 | 4.32 | 472.23 |
| Colon adenocarcinoma | 12.24 | 27.77 | 3.87 | 275.90 |
| Head and Neck squamous cell carcinoma | 11.37 | 32.52 | 3.47 | 1111.18 |
| Ovarian serous cystadenocarcinoma | 11.25 | 27.51 | 5.00 | 425.09 |
| Bladder Urothelial Carcinoma | 10.03 | 29.64 | 2.28 | 467.12 |
| Testicular Germ Cell Tumors | 8.68 | 72.28 | 2.94 | 1395.34 |
| Prostate adenocarcinoma | 5.92 | 11.03 | 2.74 | 648.96 |
| Kidney Chromophobe | 5.21 | 8.07 | 1.71 | 1788.92 |
| Pheochromocytoma and Paraganglioma | 4.95 | 12.24 | 2.06 | 118.84 |
| Thymoma | 3.58 | 27.15 | 0.30 | 1173.35 |
| Brain Lower Grade Glioma | 3.19 | 6.94 | 1.53 | 163.17 |
| Adrenocortical carcinoma | 2.40 | 4.87 | 0.52 | 112.69 |
| Uterine Corpus Endometrial Carcinoma | 2.20 | 7.36 | 0.49 | 172.08 |
| Uveal Melanoma | 1.81 | 3.72 | 0.89 | 16.59 |
| Cervical squamous cell carcinoma & endocervical adenocarcinoma | 1.79 | 6.34 | 0.56 | 258.49 |
| Kidney renal papillary cell carcinoma | 1.76 | 6.80 | 0.64 | 2291.27 |
| Lymphoid Neoplasm Diffuse Large B-cell Lymphoma | 0.34 | 1.11 | 0.12 | 51.63 |
| Acute Myeloid Leukemia | 0.00 | 0.13 | 0.00 | 5.84 |

Figure 2:
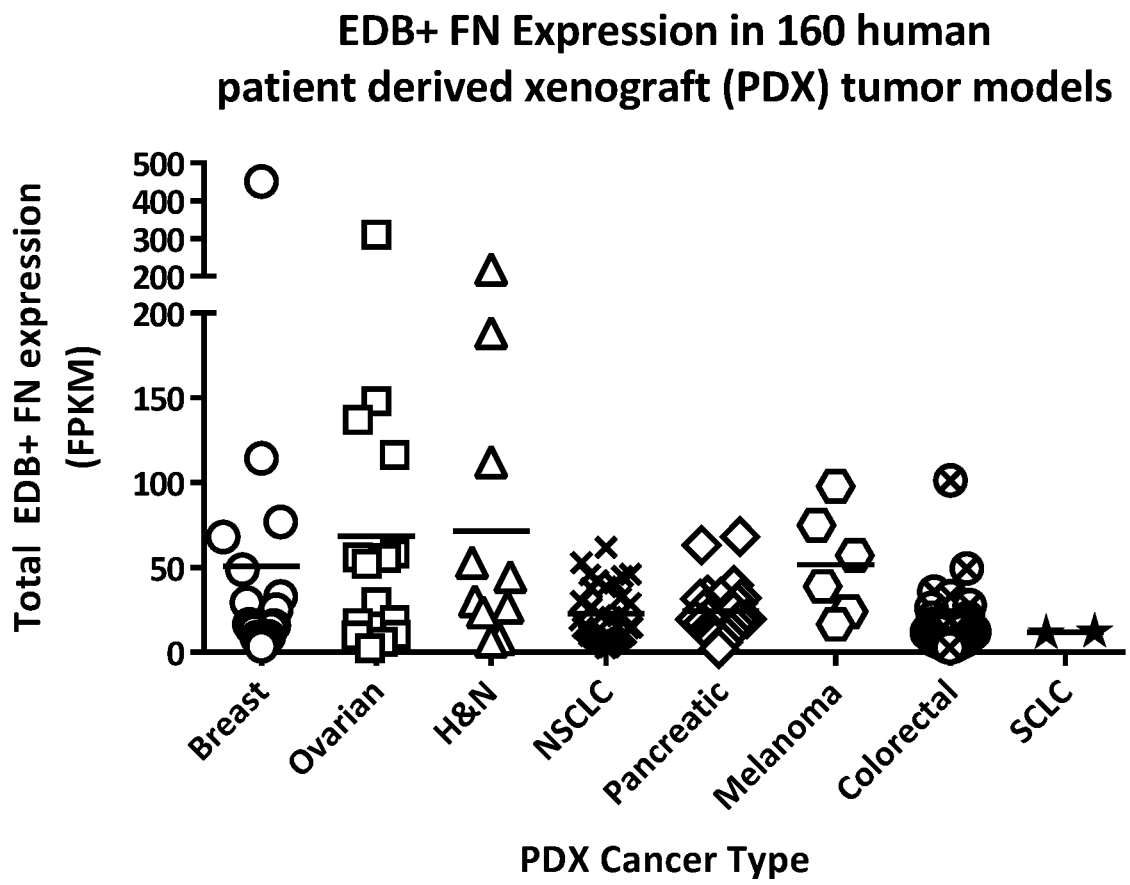
FIG. 2 shows EDB+ FN expression using RNA-Seq analysis in human patient derived xenograft (PDX) cancer models.

Gene expression quantification was performed on the RNA-Seq data of 160 Pfizer internal patient derived xenograft (PDX) models from breast cancer, ovarian cancer, head & neck cancer, colorectal cancer, melanoma, pancreatic, non-small cell lung cancer (NSCLC) and small cell lung cancer using RSEM program. See Li et al., BMC Bioinformatics, 12:323, 2011. EDB+ FN expression was calculated as the summation of expression levels of the isoforms of fibronectin (FN1) which harbor EDB. As shown in FIG. 2, EDB+ FN was expressed at varying levels (all samples had levels >1) across all tumor types analyzed. Data represented as fragment per kilobase of transcript per million reads (FPKM).

Immunohistochemistry (IHC) Detection of EDB+ FN Expression

EDB+ FN protein expression in human cancer was validated by IHC using EDB-L19 antibody in frozen sections. Eight micron fresh frozen tissue sections that were embedded in TISSUE-TEK® O.C.T. Compound (Sakura Finetek, slide preparation formulation) were fixed for 4 minutes in a 3:1 mixture of acetone to 100% ethanol and then dipped in 10% neutral buffered formalin for 20 seconds. Slides were rinsed in TBS. Endogenous peroxidase activity was inactivated with Peroxidazed 1 (Biocare Medical) for 10 minutes. Non-specific protein interactions were blocked for 10 minutes with Background Punisher (Biocare Medical). EDB-L19 antibody or isotype negative control huNeg-8.8 antibody was pre-complexed with rabbit anti-human IgG (Jackson ImmunoResearch) at a final concentration of 3 µg/ml and 0.5 µg/ml respectively, for 1 hour at room temperature. The pre-complexed mixture was incubated with excess whole human IgG (Jackson ImmunoResearch) for 15 minutes at room temperature and was added to the slides for 1 hour. Sections were washed in TBS and incubated with SIGNALSTAIN® Boost Rabbit HRP (Cell Signaling Technologies, modification-specific antibodies and reagents) modification-specific antibodies and reagents for 30 minutes. Chromogenic signal was developed with DAB+ (Dako) for 5 minutes, and subsequently quenched with distilled $H_2O$. Slides were briefly counterstained with CAT Hematoxylin (Biocare Medical), washed in water, dehydrated in graded alcohols, cleared in xylene, and cover-slipped with PERMOUNT® Mounting Medium (Fisher-Chemicals, mounting medium for microscope slides) mounting medium for microscope slides. Analysis of expression was performed and confirmed.

As shown in Table 16, EDB+ FN protein was expressed at moderate to high levels across the all human cancer indications profiled, including head and neck carcinoma (data not shown), pancreatic carcinoma, non-small cell lung carcinoma (NSCLC), ovarian carcinoma and breast carcinoma. Expression in all tumors was dominantly stromal (including fibroblastic and that associated with the vasculature), though some staining of tumor cells was also observed.

TABLE 16

EDB+ FN protein expression in human cancer assessed by IHC assay.

| Tumor type | # patient samples | % samples with EDB+ FN stromal positivity | |
|---|---|---|---|
| | | Negative/Low | Moderate/High |
| Pancreatic | 20 | 30 | 70 |
| Lung | 15 | 0 | 100 |
| Breast | 12 | 8 | 92 |
| Ovarian | 10 | 0 | 100 |

Example 6

IN Vitro Binding of EDB ADCs

To assess the relative binding of anti-EDB antibodies and EDB ADCs to EDB, MaxiSorp 96-well plates were coated with 0.5 or 1 µg/ml of human 7-EDB-89 (SEQ ID NO: 34) in PBS and incubated overnight at 4° C. with gentle shaking. Plates were then emptied, washed with 200 µl PBS and blocked with 100 µl of Blocking Buffer (ThermoScientific) for 3 hours at room temperature. Blocking buffer was removed, wells were washed with PBS and incubated with 100 µl of anti-EDB antibodies or EDB ADCs which were serially diluted (4-fold) in ELISA Assay Buffer (EAB; 0.5% BSA/0.02% Tween-20/PBS). The first column of the plate was left empty and the last column of the plate was filled with EAB as blank controls. The plate was incubated at room temperature for 3 hours. Reagents were removed and plate washed with 200 µl of 0.03% Tween-20 in PBS (PBST). Anti-human IgG-Fc-HRP (Thermo/Pierce) diluted 1:5000 in EAB was added as 100 µl to the wells and incubated for 15 minutes at room temperature. The plate was washed with 200 µl of PBST, then 100 µl of BIOFX® TMB (Fisher, HRP substrate) was added and the color allowed to develop for 4 minutes at room temperature. The reaction was stopped with 100 µl of 0.2 N sulfuric acid and absorbance at 450 nm was read on a Victor plate reader (Perkin Elmer, Waltham, MA).

Figure 3A:
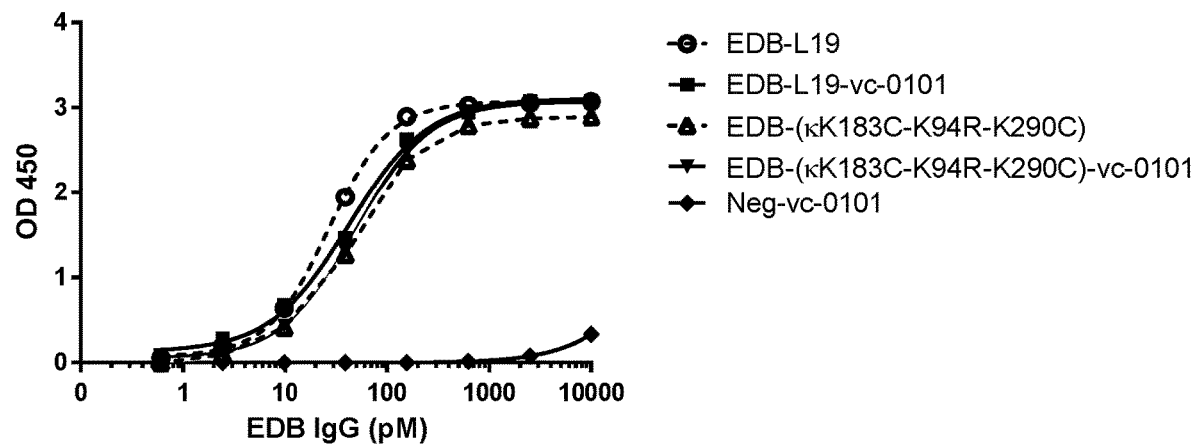
FIGS. 3A and 3B show ELISA binding curves for [A] EDB-L19 antibody and EDB-L19-vc-0101 ADC, and EDB-(κK183C-K94R-290C) antibody and EDB-(κK183C-
Figure 3B:
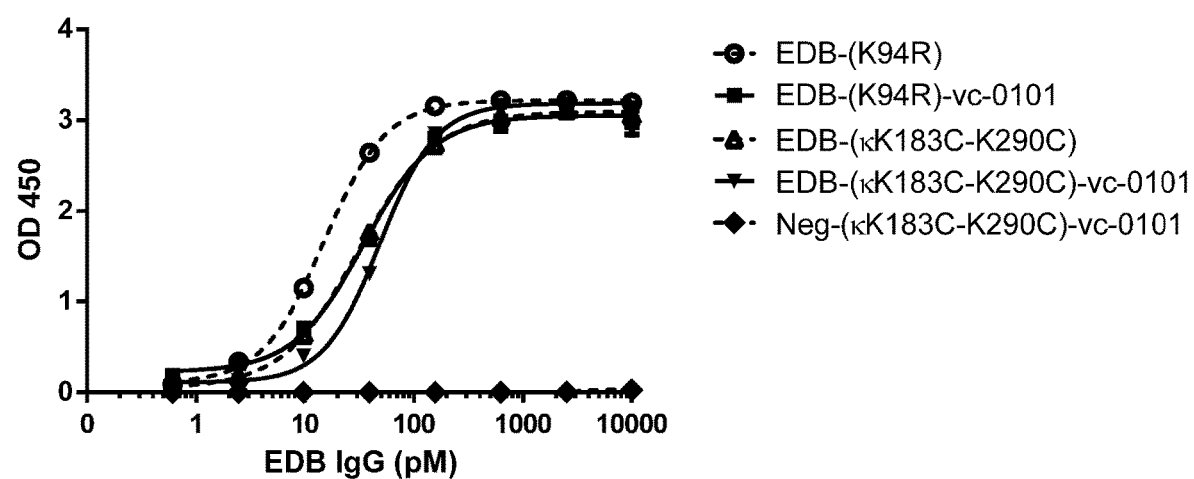

Table 17 provides the relative binding of anti-EDB antibodies and EDB ADCs to human 7-EDB-89 protein fragment bound to a 96-well plate in ELISA format. All antibodies and ADCs targeting EDB bound to the target protein with similar affinity in the range of 19 pM to 58 pM. In contrast, non-EDB targeting antibodies and ADCs have high $EC_{50}$ values >10,000 pM. Representative ELISA binding curves are illustrated in FIGS. 3A and 3B.

TABLE 17

Anti-EDB antibody and ADC binding to human EDB.

| ADC or Antibody # | ADC or Antibody Name | Avg $EC_{50}$ (pM) | SD |
|---|---|---|---|
| Ab1 | EDB-L19 | 27.0 | — |
| ADC1 | EDB-L19-vc-0101 | 37.8 | 12.8 |
| ADC11 | Neg-vc-0101 | >10,000 | — |
| Ab2 | EDB-(κK183C-K290C) | 30.2 | 1.6 |
| ADC2 | EDB-(κK183C-K290C)-vc-0101 | 58.4 | 17.0 |
| ADC12 | Neg-(κK183C-K290C)-vc-0101 | >10,000 | ND |
| Ab3 | EDB-(K94R) | 15.0 | — |
| ADC3 | EDB-(K94R)-vc-0101 | 37.1 | 14.6 |
| Ab4 | EDB-(κK183C-K94R-K290C) | 44.8 | 8.7 |
| ADC4 | EDB-(κK183C-K94R-K290C)-vc-0101 | 56.7 | 13.5 |
| ADC5 | EDB-L19-diS-DM1 | 21.3 | — |
| ADC6 | EDB-L19-diS-$C_2$OCO-1569 | 30.7 | — |
| ADC7 | EDB-L19-vc-9411 | 37.5 | — |
| ADC15 | Neg-vc-9411 | >10,000 | — |
| ADC8 | EDB-L19-diS-4574 | 31.9 | — |
| Ab5 | EDB-(H16-K222R) | 19.3 | — |
| ADC9 | EDB-(H16-K222R)-AcLys-vc-CPI-8314 | 39.4 | 2.5 |
| ADC17 | Neg-(H16-K222R)-AcLys-vc-CPI-8314 | >10,000 | — |

Mean $EC_{50}$ ± standard deviation and number (n) of determinations.
ND = not determined.

Example 7

In Vitro Cytotoxicity of EDB ADCs

Cell Culture

WI38-VA13 are SV40-transformed human lung fibroblasts obtained from ATCC and maintained in MEM Eagles media (Cell-Gro), supplemented with 10% FBS, 1% MEM non-essential amino acids, 1% sodium pyruvate, 100 units/ml penicillin-streptomycin, and 2 mM GLUTAMAX® (Gibco; glutamine substitute). HT29 are derived from human colorectal carcinoma (ATCC) and maintained in DMEM media supplemented with 10% FBS and 1% glutamine.

EDB+ FN Transcript Detection

For gene expression and transcript analysis of EDB+ FN, adherent proliferating WI38-VA13 and HT29 cells were dissociated from cell-culture flasks with TRYPLE® Express (Gibco, cell dissolution buffer). The RNEASY® Mini Kit (Qiagen, RNA purification kit) was used to purify total RNA from the collected cell pellets. The residual DNA was removed by RNase-Free DNase Set (Qiagen) during RNA purification. High Capacity RNA-to-cDNA Kit (Applied Biosystems) was used for reverse transcription of total RNA to cDNA. The cDNA was analyzed by quantitative real-time PCR using TAQMAN® Universal Master Mix II (Roche; DNA amplification kit), with UNG (Applied Biosystems). EDB+ FN signal was detected by TAQMAN® (Roche, DNA amplification kit) primer Hs01565271_m1 and normalized with the average of both signals from ACTB (TaqMan primer Hs99999903_m1) and GAPDH (TaqMan primer Hs99999905_m1). All primers were from ThermoFisher Scientific. Data from a representative experiment is shown.

EDB+ FN Protein Detection by Western Blotting

For detection of EDB+ FN by western blotting, adherent proliferating WI38-VA13 and HT29 cells were harvested by cell scraping. Cell lysates were prepared in Cell Lysis Buffer (Cell Signaling Technology) with protease inhibitors and phcOmplete ULTRA Tablets, Mini, EDTA-free osphatase inhibitors. Tumor lysate was prepared in either RIPA Lysis Buffer or 2× Cell Lysis Buffer (Cell Signaling Technology) with protease inhibitors and phcOmplete ULTRA Tablets, Mini, EDTA-free osphatase inhibitors. Protein lysates were analyzed by SDS-PAGE and followed by western blotting. Proteins were transferred to nitrocellulose membrane and then blocked with 5% milk/TBS, followed by incubation with EDB-L19 antibody and anti-GAPDH antibody (Cell Signaling Technology) overnight at 4° C. After washing, the anti-EDB blot was incubated with ECL HRP-linked anti-human IgG secondary antibody (GE Healthcare) for 1 hour at room temperature. After washing, the EDB+ FN signal was developed by Pierce ECL 2 Western Blotting Substrate (Thermo Scientific) and detected by X-ray films. The anti-GAPDH blot was incubated with ALEXA FLUOR® 680 (Molecular Probes, Inc.; fluorescent chemicals and biomolecule labeling kits) conjugated anti-rabbit IgG secondary antibody (Invitrogen) in blocking buffer for 1 hour at room temperature. After washing, the GAPDH signal was detected by LI-COR ODYSSEY® (Li-Cor, optical measuring instrument) Imaging System. Densitometric analysis of EDB+ FN western blots was conducted using the Bio-Rad GS-800 Calibrated Imaging Densitometer and quantified using Quantity One version 4.6.9 software. Data from a representative experiment is shown.

FIG. 4 shows EDB+ FN expression by western blot in WI38-VA13 and HT29 cells. EDB+ FN is expressed in the WI38-VA13 cell line and the HT29 colon carcinoma cell line is negative when grown in vitro.

EDB+ FN Protein Detection by Flow Cytometry

EDB-L19 antibody was used to measure the expression of EDB+ FN on the cell surface of WI38-VA13 or HT29 cells by flow cytometry. Cells were dissociated by non-enzymatic cell dissociation buffer (Gibco) and incubated with cold flow buffer (FB, 3% BSA/PBS+Ca+Mg) on ice for blocking. Cells were then incubated with primary antibodies on ice in FB. After the incubation, cells were washed with cold PBS–Ca–Mg and then incubated with viability stain (Biosciences) to discriminate live and dead cells, according to the manufacture's procedure. The signals were analyzed on a BD Fortessa flow cytometer and data were analyzed using BD FACS DIVA software. Data from a representative experiment is shown.

Table 18 summarizes the results from western blot, qRT-PCR and flow cytometry. The data demonstrates that WI38-VA13 is EDB+ FN positive and HT29 is EDB+ FN negative.

TABLE 18

Characterization of EDB+ FN expression in WI38 VA13 and HT29 cells

| Cell Line | qRT-PCR ($2^{(-ddC(t))}$) | Western (normalized density (OD/mm2)) | Flow cytometric binding (MFI-GeoMean (EDB+ FN unstained)) |
|---|---|---|---|
| WI38-VA13 | 0.224247 | 475.397 | 4480 |
| HT29 | 0.000049 | 0.093 | 2 |

In Vitro Cytotoxicity Assays

Proliferating WI38-VA13 or HT29 cells were harvested from culture flasks with non-enzymatic cell dissociation buffer and cultured overnight in 96-well plates (Corning) at 1000 cells/well in a humidified chamber (37° C., 5% CO2). The next day, cells were treated with EDB ADCs or isotype control non-EDB-binding ADCs by adding 50 µl of 3× stocks in duplicate at 10 concentrations. In some experiments, cells were plated at 1500 cells/well and treated the same day. Cells were then incubated with EDB ADCs or isotype control non-EDB-binding ADCs for four days. On harvest day, 50 µl of Cell Titer Glo (Promega) was added to the cells and incubated 0.5 hours at room temperature. Luminescence was measured on a Victor plate reader (Perkin Elmer, Waltham, MA). Relative cell viability was determined as a percentage of untreated control wells. $IC_{50}$ values were calculated using four-parameter logistic model #203 with XLfit v4.2 (IDBS).

Table 19 shows the $IC_{50}$ (ng/ml of antibody) of the EDB ADC treatments in cytotoxicity assays performed on WI38-VA13 (EDB+ FN positive tumor cell line) and HT29 colon carcinoma cells (EDB+ FN negative tumor cell line). The EDB ADCs induced cell death in the EDB+ FN expressing cell line. The $IC_{50}$ values were similar for all EDB ADCs having vc-0101 linker-payload, in the range of approximately 184 ng/ml to 216 ng/ml (EDB-L19-vc-0101, EDB-(κK183C–K290C)-vc-0101, EDB-(K94R)-vc-0101, EDB-(κK183C-K94R-K290C)-vc-0101). The negative control vc-0101 ADCs were substantially less potent, with $IC_{50}$ values approximately 70- to 200-fold higher than EDB-vc-0101 ADCs. All vc-0101 ADCs had 46- to 83-fold higher $IC_{50}$ values in the EDB+ FN negative tumor cell line, HT29. Therefore, EDB ADCs were dependent on EDB+ FN expression for their in vitro cytotoxicity.

Other auristatin-based EDB ADCs with "vc" protease-cleavable linkers, EDB-L19-vc-9411 and EDB-L19-vc-1569, also showed potent cytotoxicity in WA38-VA13 cells with high selectivity of about 50- to 180-fold compared with the corresponding negative control ADCs and selectivity of about 25- to 140-fold compared with the non-expressing cell line. The EDB-L19-diS-DM1 ADC had similar potency as the vc-0101 ADCs, however much lower selectivity compared with the negative control ADC (about 3-fold) and with HT29 cells (about 0.9-fold).

TABLE 19

In vitro cytotoxicity of EDB ADCs and control non-EDB-binding ADCs.

| ADC # | ADC Name | WI38-VA13 Avg $IC_{50}$ | SD | n | HT29 Avg $IC_{50}$ | SD | n |
|---|---|---|---|---|---|---|---|
| ADC1 | EDB-L19-vc-0101 | 184 | 143 | 23 | 15,346 | 4448 | 5 |
| ADC11 | Neg-vc-0101 | 19,585 | 6762 | 16 | 10,731 | 8193 | 24 |
| ADC2 | EDB-(κK183C-K290C)-vc-0101 | 198 | 176 | 6 | 9,276 | 83 | 2 |
| ADC12 | Neg-(κK183C-K290C)-vc-0101 | >40,000 | ND | 4 | 21,913 | 2635 | 2 |
| ADC3 | EDB-(K94R)-vc-0101 | 184 | 138 | 7 | 10,577 | 2065 | 2 |
| ADC4 | EDB-(κK183C-K94R-K290C)-vc-0101 | 216 | 94 | 6 | 15,584 | 58 | 3 |
| ADC5 | EDB-L19-diS-DM1 | 268 | 150 | 8 | 237 | 180 | 2 |
| ADC13 | Neg-diS-DM1 | 879 | 82 | 5 | ND | ND | ND |
| ADC6 | EDB-L19-diS-C2OCO-1569 | 21 | 8 | 6 | 5 | 3 | 2 |
| ADC14 | Neg-diS-C2OCO-1569 | 36 | 6 | 3 | ND | ND | ND |
| ADC7 | EDB-L19-vc-9411 | 46 | 22 | 3 | 1,153 | — | 1 |
| ADC15 | Neg-vc-9411 | 2,514 | 260 | 3 | 1,243 | — | 1 |
| ADC8 | EDB-L19-diS-4574 | 487 | 406 | 4 | 429 | 228 | 2 |
| ADC16 | Neg-diS-4574 | 1,279 | — | 1 | ND | ND | ND |
| ADC9 | EDB-(H16-K222R)-AcLys-vc-CPI-8314 | 34 | 30 | 5 | 3,449 | — | 1 |
| ADC17 | Neg-AcLys-vc-CPI-8314 | 2,656 | 876 | 3 | 15,110 | 15,408 | 2 |

TABLE 19-continued

In vitro cytotoxicity of EDB ADCs and control non-EDB-binding ADCs.

| | | WI38-VA13 | | | HT29 | | |
|---|---|---|---|---|---|---|---|
| ADC # | ADC Name | Avg $IC_{50}$ | SD | n | Avg $IC_{50}$ | SD | n |
| ADC10 | EDB-L19-vc-1569 | 40 | 11 | 2 | 5,702 | — | 1 |
| ADC18 | Neg-vc-1569 | 7283 | — | 1 | ND | ND | ND |

Mean $IC_{50}$ ± standard deviation and number (n) of determinations.
ND = not determined.

As shown in Table 20, the unconjugated payloads were highly potent in both cell lines, independent of EDB+ FN expression, indicating that these cells are sensitive to the cytotoxic agents used as ADC payloads.

TABLE 20

In vitro cytotoxicity potency of various unconjugated compounds.

| | WI38-VA13 | | | HT29 | | |
|---|---|---|---|---|---|---|
| Payload Name | Avg $IC_{50}$ (nM) | SD | n | Avg $IC_{50}$ (nM) | SD | n |
| Payload-1569 | 0.269 | 0.134 | 7 | 0.074 | 0.080 | 3 |
| Payload-DM1 | 3.06 | 2.77 | 5 | 2.63 | 2.30 | 8 |
| Payload-0101 | 0.392 | 0.326 | 12 | 0.090 | 0.043 | 14 |
| Payload-0326 | <0.001 | ND | 2 | 0.049 | 0.028 | 2 |
| Payload-4574 | 3.54 | 1.14 | 2 | 3.65 | 1.89 | 2 |
| Payload-9411 | 0.519 | 0.144 | 2 | 0.197 | 0.177 | 3 |
| Payload-Cemadotin | 24.2 | 2.14 | 2 | 43.8 | — | 1 |

Mean $IC_{50}$ ± standard deviation and number (n) of determinations.
ND = not determined.

Example 8

In Vivo Efficacy of EDB ADCs

EDB ADCs were evaluated in cell line xenograft (CLX), patient derived xenograft (PDX) and syngeneic tumor models. Expression of EDB+ FN was detected using an immunohistochemical (IHC) assay as previously described herein.

To generate CLX models, $8 \times 10^6$ to $10 \times 10^6$ cells of H-1975, HT29, or Ramos tumor lines were implanted into female athymic nude mice subcutaneously. Ramos and H-1975 cells for inoculation were suspended in 50% and 100% MATRIGEL® (BD Biosciences, biological call culture substrate), respectively. For the Ramos model, the animals received whole body irradiation (4 Gy) before cell inoculation to facilitate the establishment of tumors. When the average tumor volume reached approximately 160 to 320 mm 3, the animals were randomized into treatment groups, with 8-10 mice in each group. ADCs or vehicle (PBS) were administered intravenously on day 0 and then the animals were dosed once every 4 days for 4 to 8 doses. Tumors were measured once or twice weekly and tumor volume was calculated as volume (mm 3)=(width×width×length)/2. The body weight of animals was monitored for 4 to 9 weeks and no animal weight loss was observed in any treatment groups.

To generate PDX models, tumors were collected from donor animals and tumor fragments approximately 3×3 mm were implanted subcutaneously into the flank of female athymic nude mice (for PDX-NSX-11122 model) or NOD SCID mice (for PDX-PAX-13565 and PDX-PAX-12534 models) by using a 10 gage trocar. When average tumor volume reached approximately 160 to 260 mm 3 the mice were randomized into treatment groups, with 7-10 mice in each group. ADCs or vehicle (PBS) dosing regime and administration route as well as tumor measurement procedures are the same as described above for CLX models. The body weight of animals was monitored for 5 to 14 weeks and no animal weight loss was observed in any treatment groups. Tumor growth inhibition is plotted as an average of tumor size ±SEM.

Expression of EDB+ FN

As shown in Table 21, expression of EDB+ FN in the H-1975, HT29 and Ramos CLX models, PDX-NSX-11122, PDX-PAX-13565 and PDX-PAX-12534 PDX models and EMT-6 syngeneic syngeneic tumor models was measured by binding of EDB-L19 antibody and subsequent detection in IHC assay. The CLX HT-29 was a moderate expressing CLX however was negative when examined in vitro due to the predominance of protein expression in the CLX being derived from the tumor stroma.

TABLE 21

Expression of EDB+ FN

| Efficacy Model | Tumor Type | EDB+ FN Overall Expression |
|---|---|---|
| PDX-NSX-11122 | NSCLC PDX | High |
| EMT-6 | Syngeneic mouse mammary carcinoma (breast) | High |
| PDX-PAX-13565 | Pancreatic adenocarcinoma PDX | Moderate/High |
| H-1975 | NSCLC CLX | Moderate/High |
| HT29 | Colorectal cancer CLX | Moderate |
| Ramos | Burkitt's lymphoma CLX | Moderate |
| PDX-PAX-12534 | Pancreatic adenocarcinoma PDX | Low/Moderate |

PDX-NSX-11122 NSCLC PDX

Figure 5A:
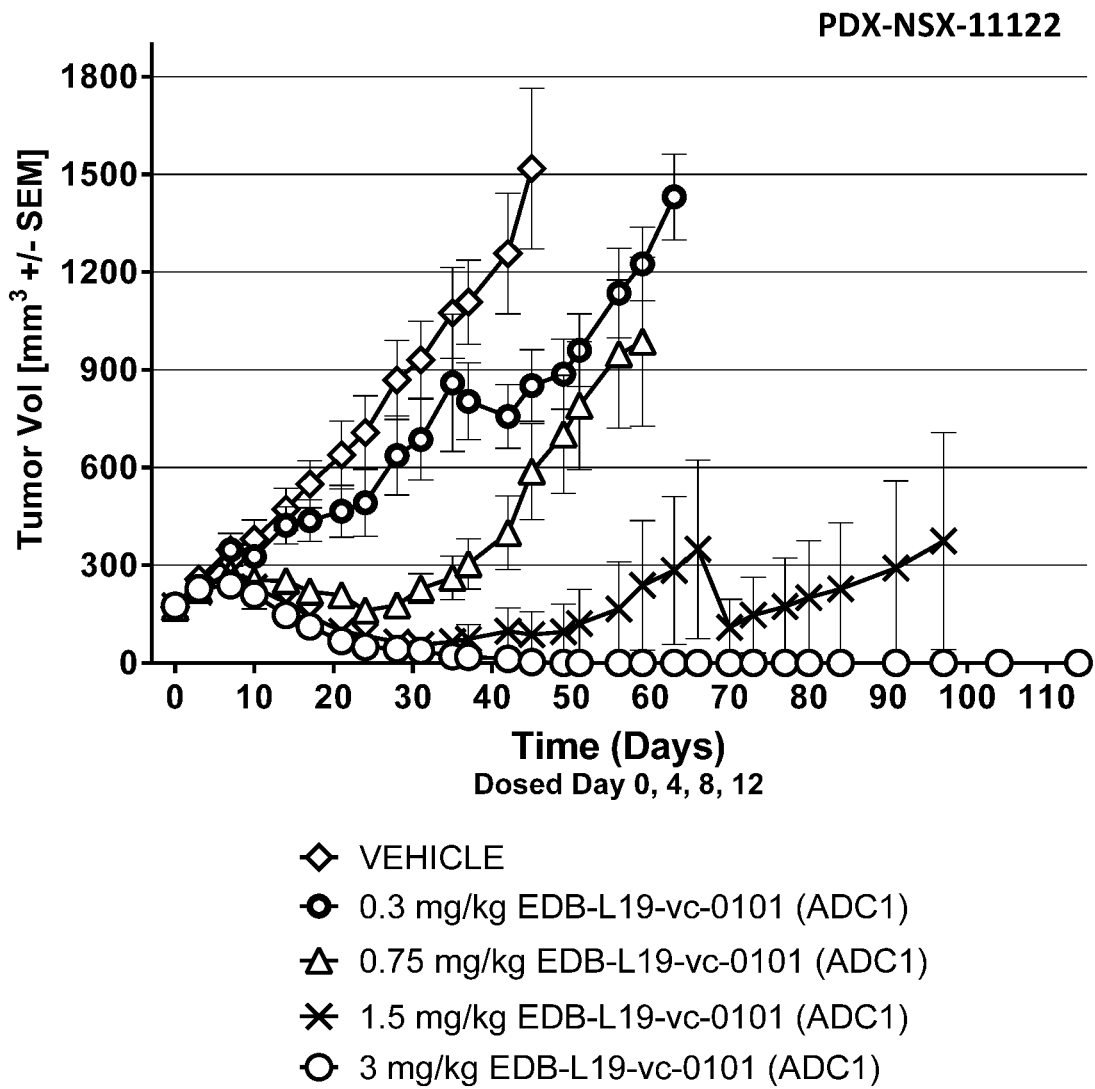

The effects of various ADCs were evaluated in PDX-NSX-11122, a NSCLC PDX model of human cancer that expresses high levels of EDB+ FN. FIG. 5A shows the anti-tumor activity for EDB-L19-vc-0101 at 0.3, 0.75, 1.5 and 3 mg/kg. The data demonstrates that EDB-L19-vc-0101 showed tumor regression in a dose dependent manner at 3 mg/kg and 1.5 mg/kg.

Figure 5B:
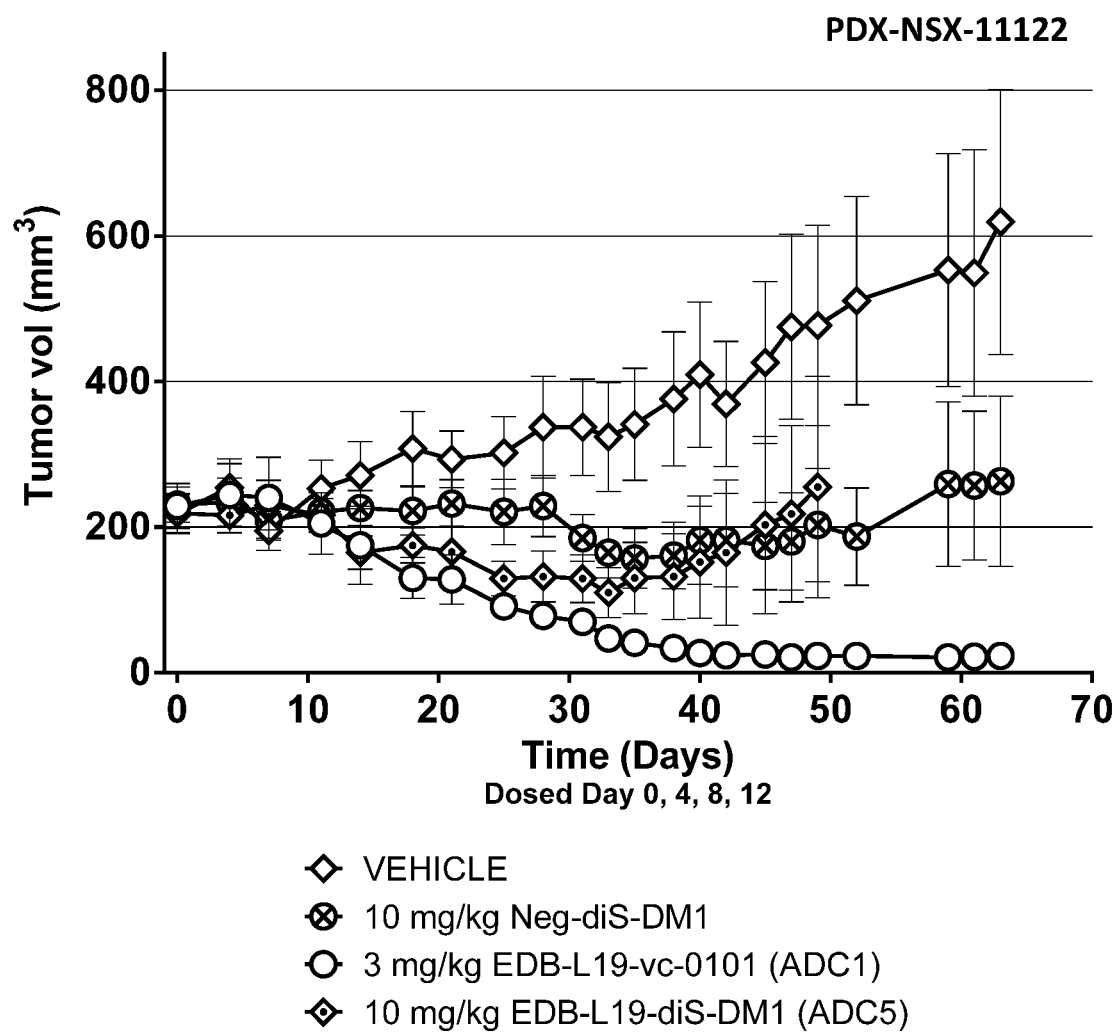
Figure 5C:
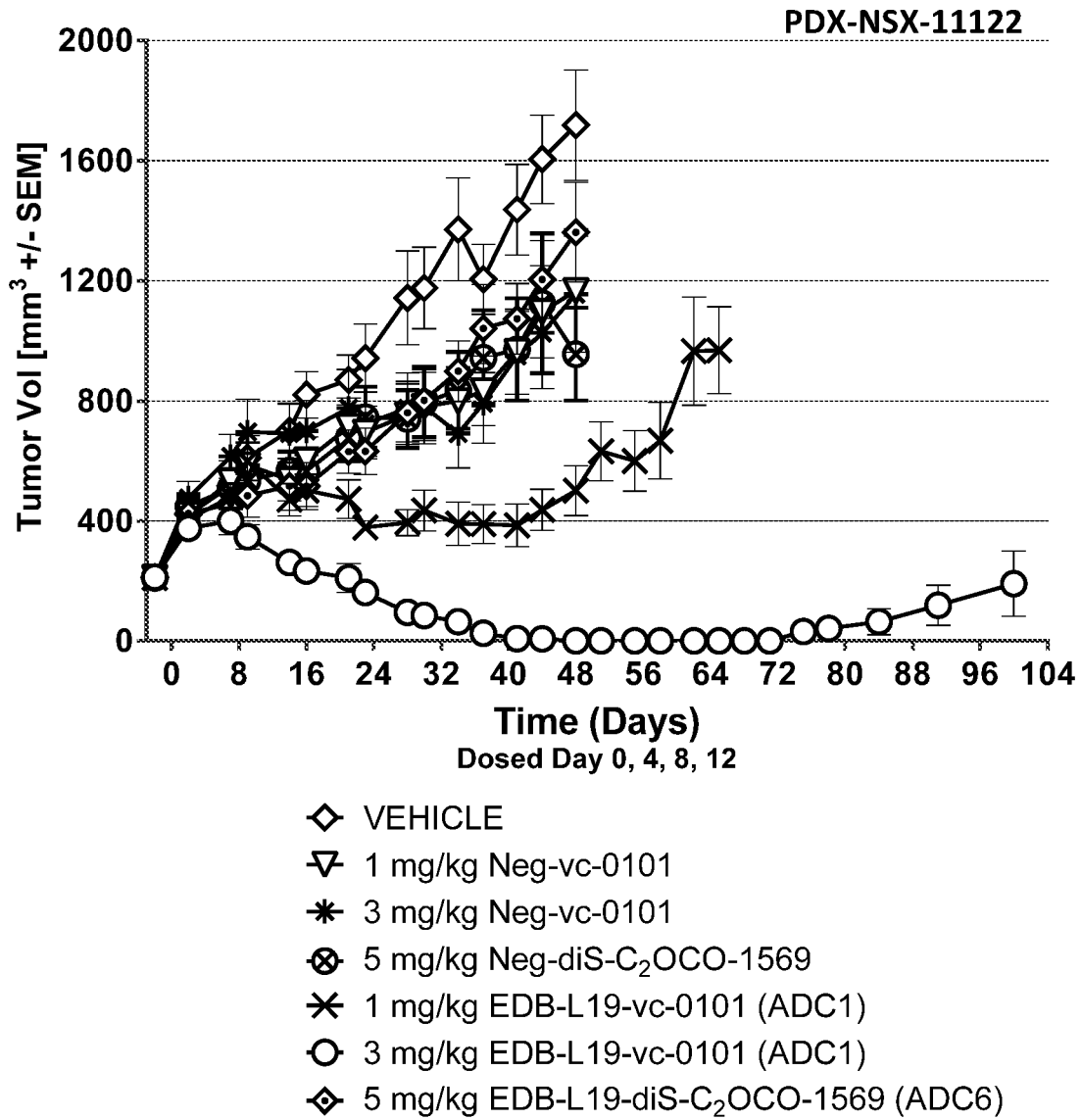

Anti-tumor efficacy of vc-linked ADCs was compared to disulfide-linked ADCs. FIGS. 5B and 5C show the anti-tumor activity of EDB-L19-vc-0101 at 3 mg/kg as compared to 10 mg/kg of disulfide linked EDB-L19-diS-DM1 and EDB-L19-vc-0101 at 1 and 3 mg/kg as compared to 5 mg/kg of disulfide linked EDB-L19-diS-$C_2$OCO-1569, respectively. As shown in FIGS. 5B and 5C, EDB-L19-vc-0101 demonstrated greater efficacy as compared to isotype negative control ADCs and ADCs that were generated using a disulfide linker, EDB-L19-diS-DM1 and EDB-L19-dis-C2OCO-1569. Further, animals bearing tumors that were treated with EDB-L19-vc-0101 had delayed tumor growth at 1 mg/kg and complete regressions at 3 mg/kg. The data demonstrates that EDB-L19-vc-0101 (ADC1) inhibits growth of PDX-NSX-11122 NSCLC xenografts in a dose-dependent manner.

Figure 5D:
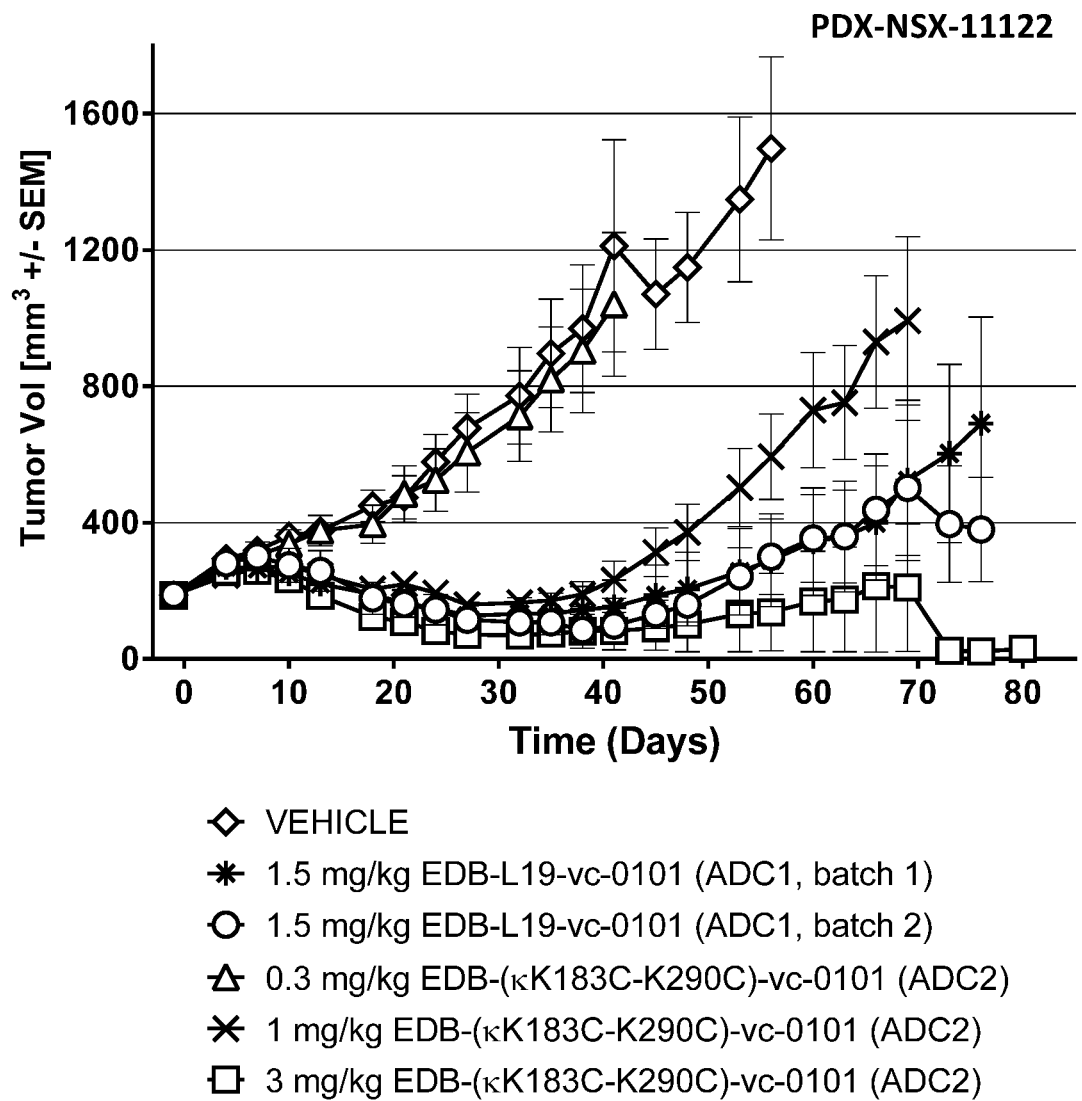

The activity of site-specific and conventionally conjugated ADCs was evaluated. FIG. 5D shows the anti-tumor efficacy of the site-specific conjugated EDB-(κK183C+K290C)-vc-0101 compared to the conventionally conjugated EDB-L19-vc-0101 at the doses of 0.3, 1 and 3 mg/kg and 1.5 mg/kg, respectively. The dose-level based efficacy was comparable and the EDB-(κK183C+K290C)-vc-0101 led to tumor regression in a dose dependent manner.

Figure 5E:
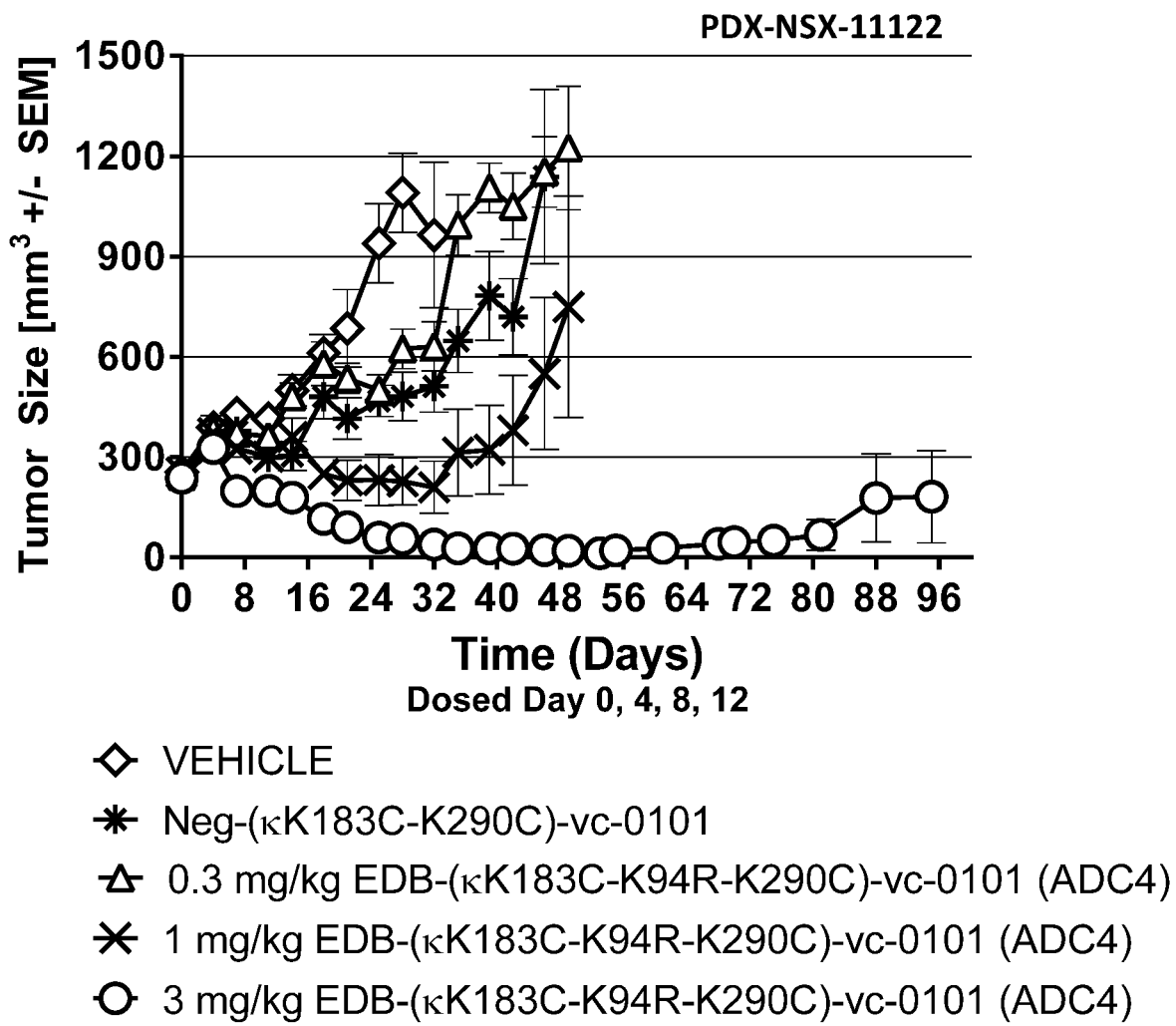
Figure 5F:
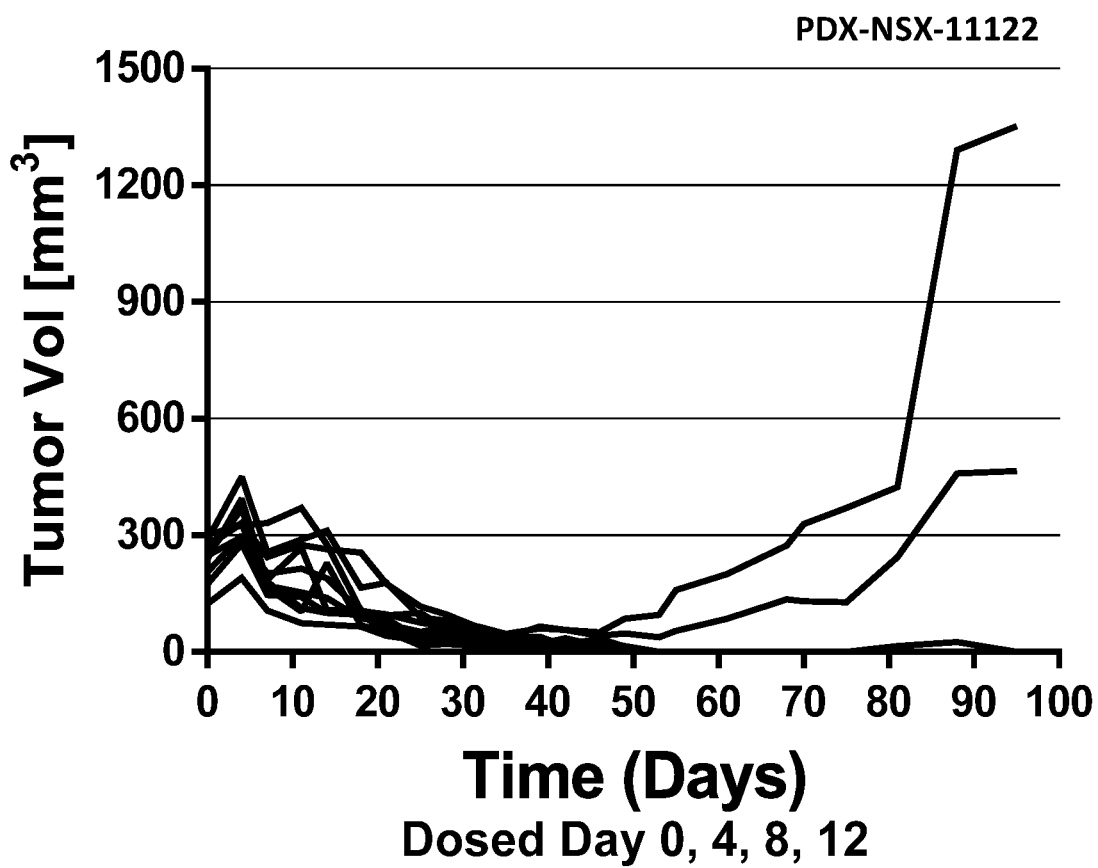

The activity of vc-0101 EDB ADCs having various mutations was assessed. FIG. 5E shows the anti-tumor efficacy of site-specific conjugated EDB-(κK183C-K94R-K290C)-vc-0101 at the doses of 0.3, 1 and 3 mg/kg. EDB-(κK183C-K94R-K290C)-vc-0101 induced tumor regression at 1 and 3 mg/kg. FIG. 5F shows the tumor growth inhibition curves for the 10 individual tumor bearing mice in the EDB-(κK183C-K94R-K290C)-vc-0101 group dosed at 3 mg/kg of FIG. 5E. The tumor regressions in the 3 mg/kg group were complete and durable in 8 of 10 mice (80%) at the end of the study (95 days).

H-1975 NSCLC CLX

Figure 6A:
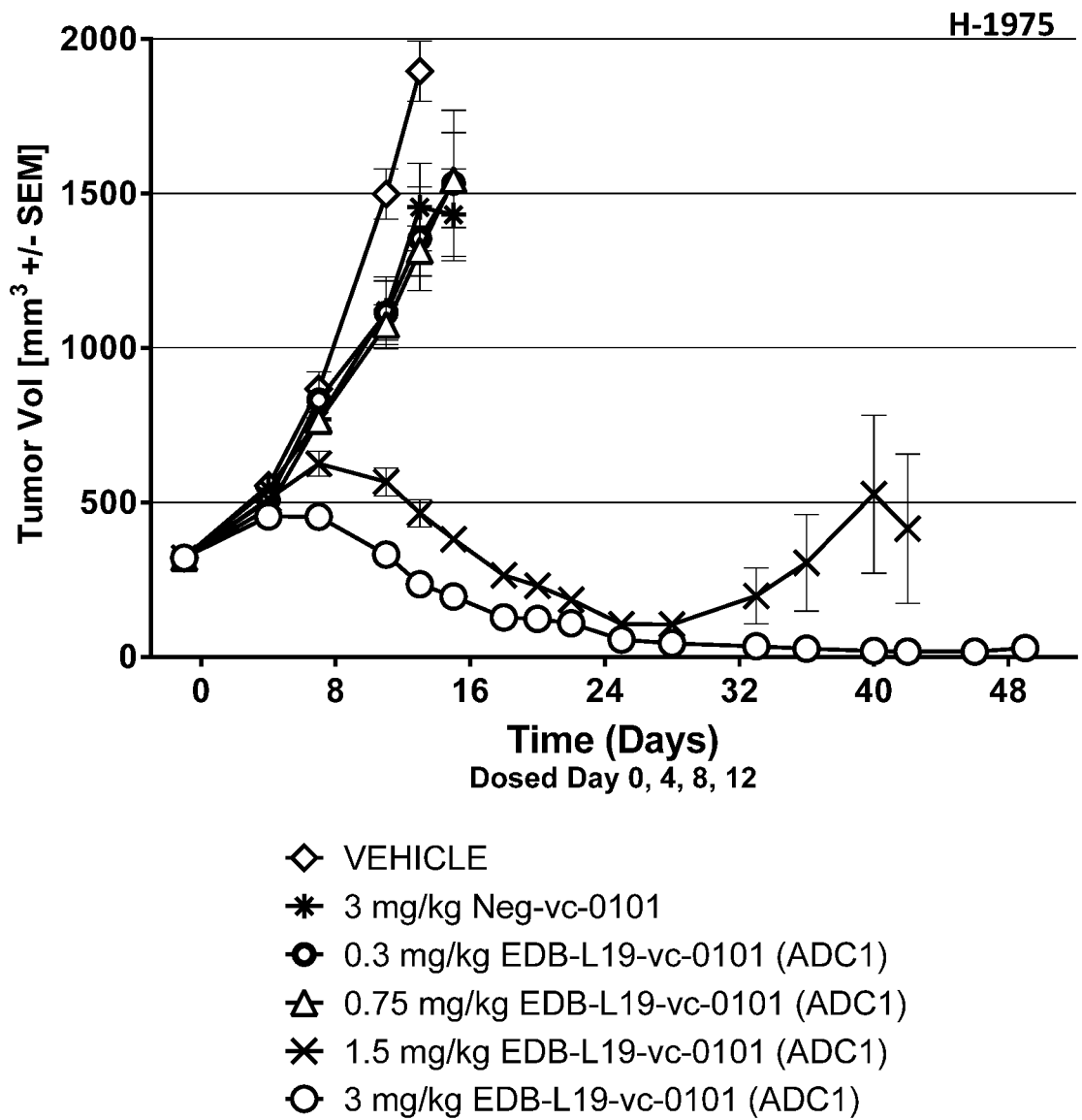
Figure 6B:
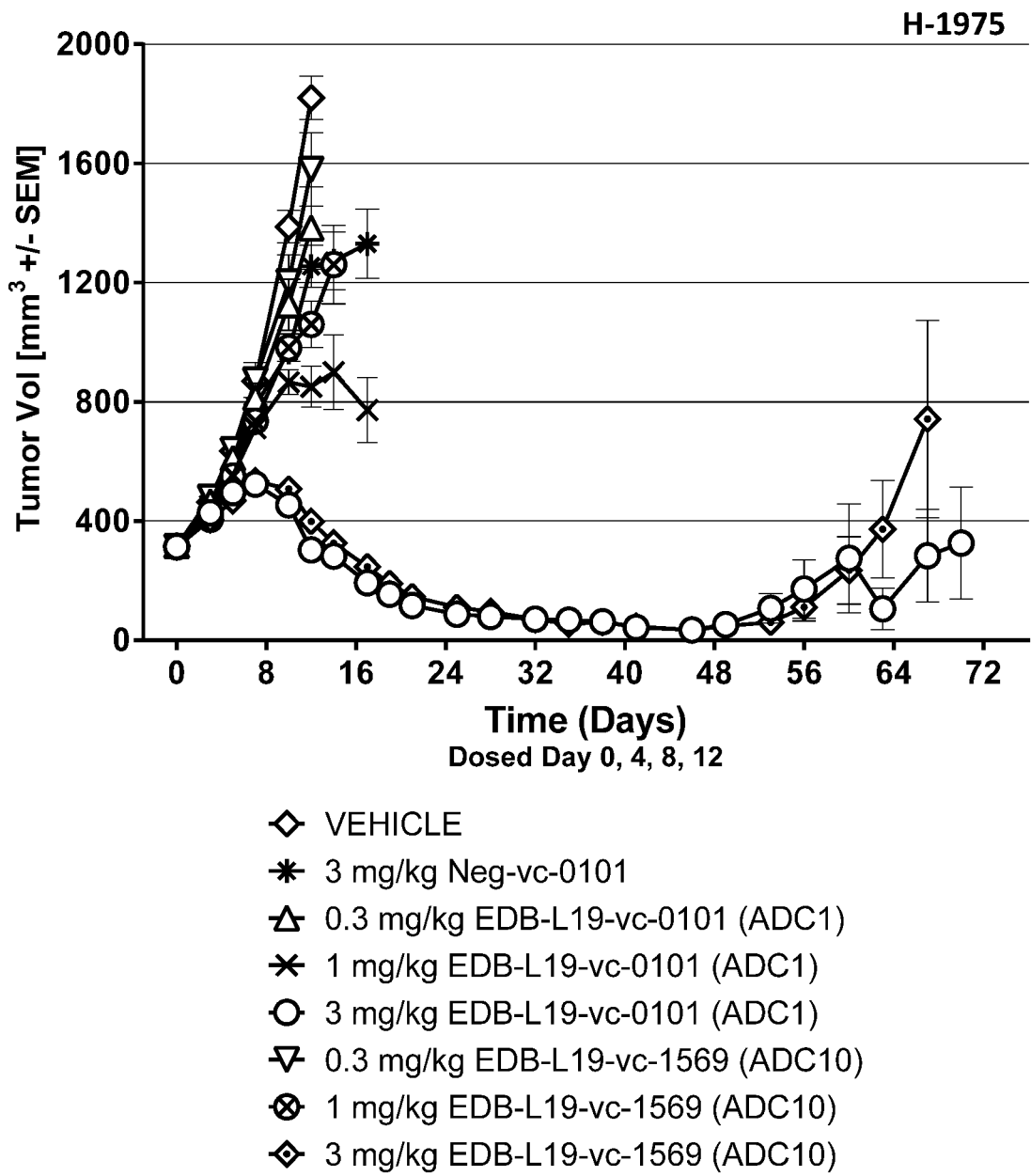

The effects of various vc-linked auristatin and CPI ADCs were evaluated in H-1975, a moderate to high EDB+ FN expressing NSCLC CLX model of human cancer. FIG. 6A shows EDB-L19-vc-0101 assessed for anti-tumor activity at 0.3, 0.75, 1.5 and 3 mg/mg. The data demonstrates that EDB-L19-vc-0101 showed tumor regression in a dose dependent manner at 3 mg/kg, and at as low as 1.5 mg/kg. FIG. 6B shows EDB-L19-vc-0101 and EDB-L19-vc-1569 were evaluated for anti-tumor activity at 0.3, 1 and 3 mg/kg. The data demonstrates that EDB-L19-vc-0101 and EDB-L19-vc-1569 showed tumor regression in a dose dependent manner.

Figure 6C:
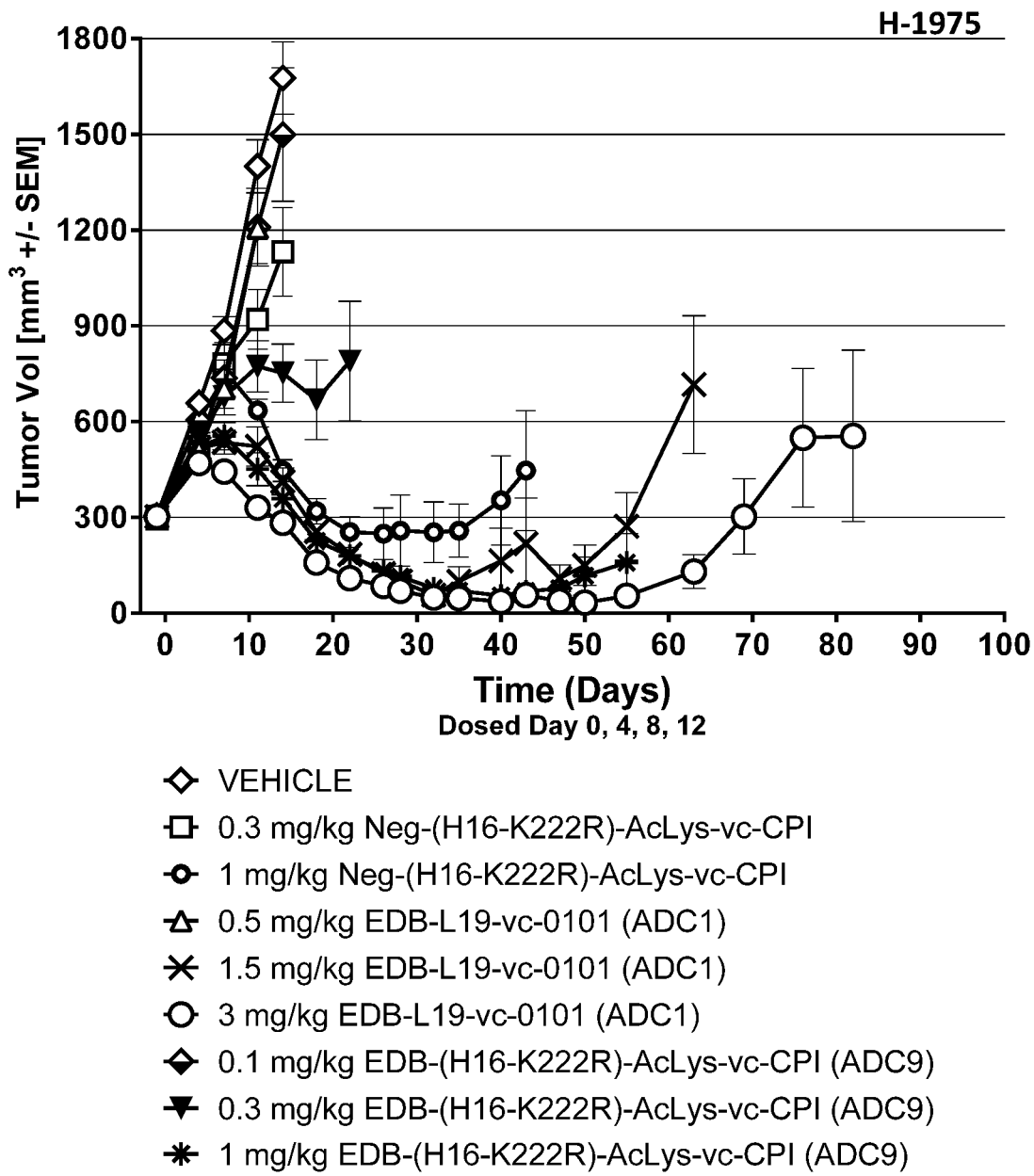

The anti-tumor activity of vc-linked auristatin ADCs were compared to CPI ADCs. As shown in FIG. 6C, EDB-L19-vc-0101 and EDB-(H16-K222R)-AcLys-vc-CPI-8314 were assessed at 0.5, 1.5 and 3 mg/kg and 0.1, 0.3 and 1 mg/kg, respectively. EDB-L19-vc-0101 and EDB-(H16-K222R)-AcLys-vc-CPI-8314 both showed tumor regression at the highest doses evaluated.

Figure 6D:
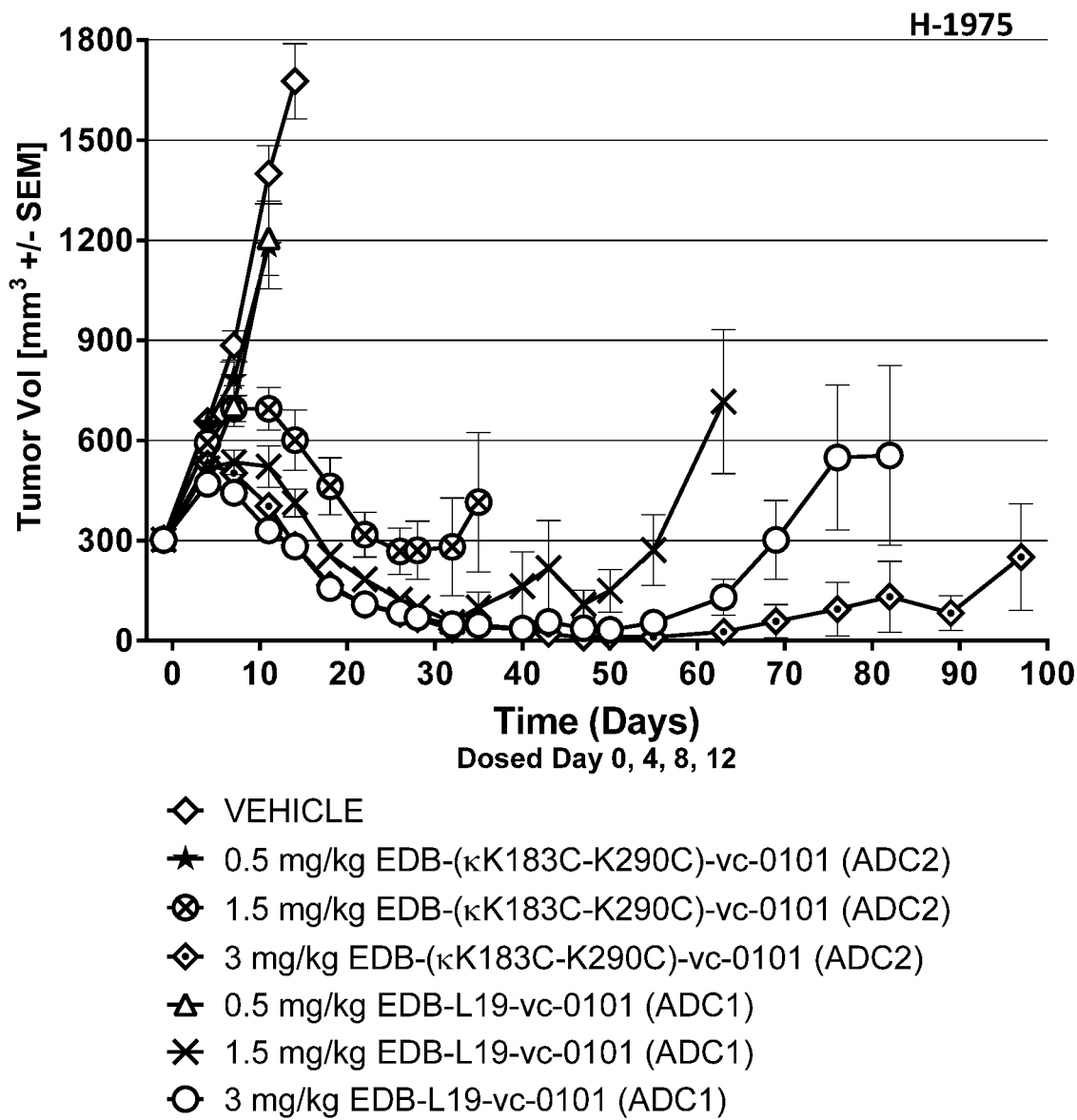

The activity of site-specific and conventionally conjugated EDB ADCs was evaluated. FIG. 6D shows the anti-tumor efficacy of the site-specific conjugated EDB-(κK183C+K290C)-vc-0101 compared to conventionally conjugated EDB-L19-vc-0101 at the doses of 0.5, 1.5 and 3 mg/kg. The dose-level based efficacy was comparable and the EDB-(κK183C+K290C)-vc-0101 led to tumor regression in a dose dependent manner.

Figure 6E:
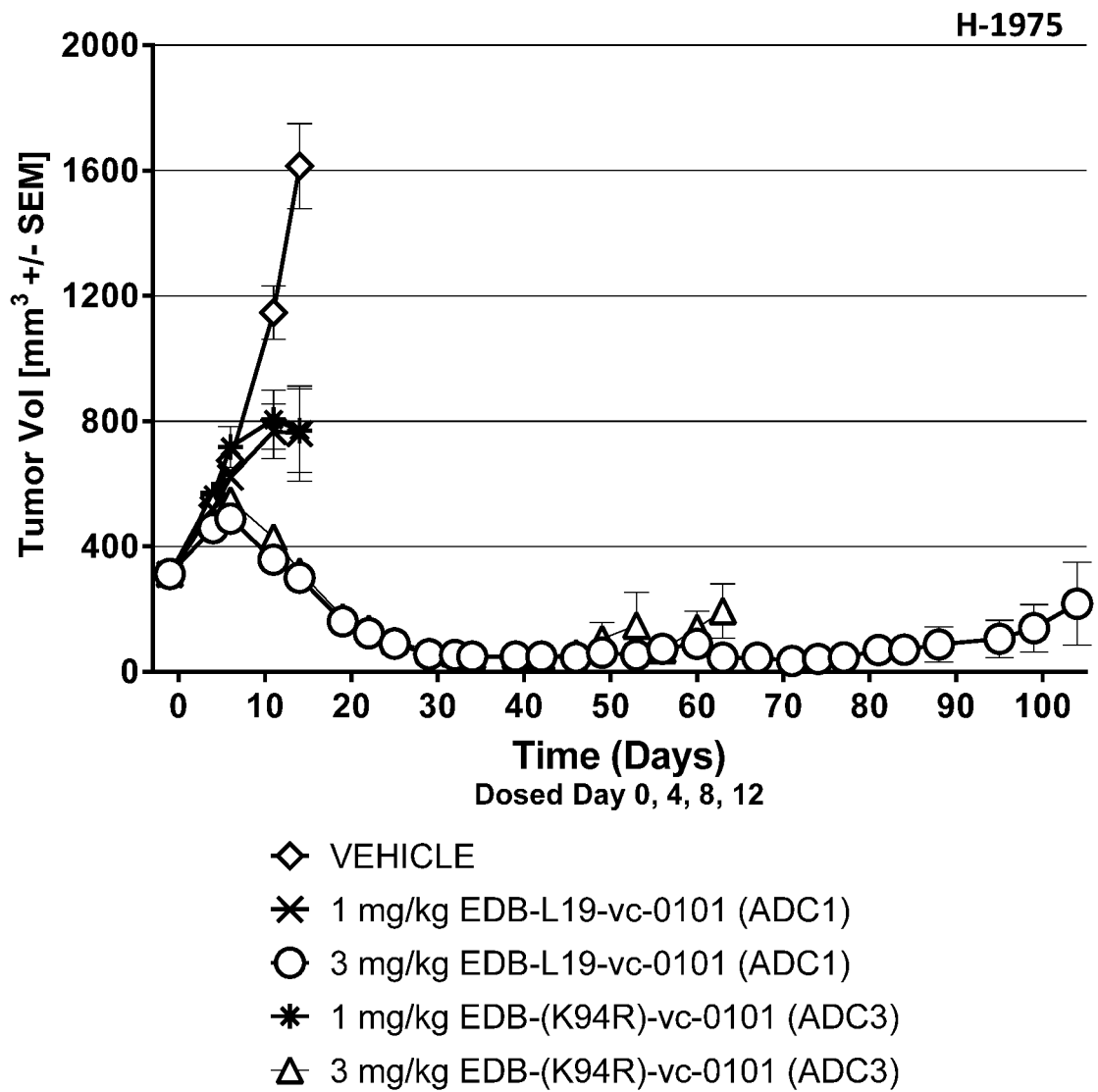
Figure 6F:
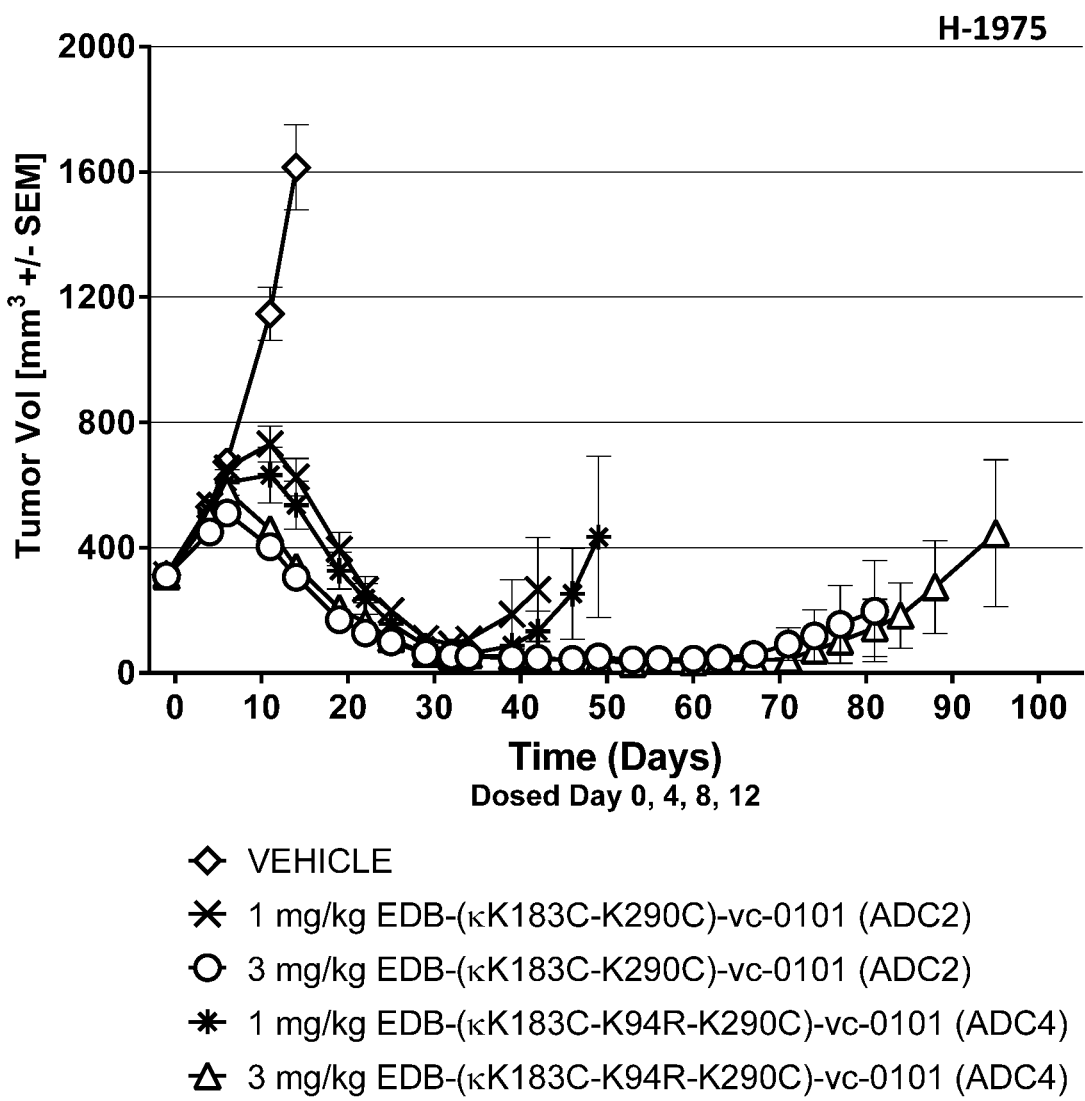

The activity of vc-0101 EDB ADCs having various mutations was assessed. FIG. 6E shows the anti-tumor efficacy of EDB-L19-vc-0101 and EDB-(K94R)-vc-0101 at 1 and 3 mg/kg. FIG. 6F shows the anti-tumor efficacy of site-specific EDB-(κK183C+K290C)-vc-0101 and EDB-(κK183C-K94R-K290C)-vc-0101 at 1 and 3 mg/kg. The 4 ADCs demonstrated similar efficacy in the H-1975 model irrespective of whether they contained the κK183C–K290C and/or K94R mutations. In addition, all ADCs tested resulted in robust anti-tumor efficacy including tumor regressions at 3 mg/kg. These data demonstrate that the introduction of the κK183C-K290C and/or K94R mutations did not negatively impact the efficacy of the ADCs.

HT29 Colon CLX

The effects of various vc-linked auristatin ADCs were evaluated in HT29, a moderate EDB+ FN expressing colon CLX model of human cancer. As shown in FIG. 7, EDB-L19-vc-0101 and EDB-L19-vc-9411 were tested for anti-tumor activity at 3 mg/kg. Both EDB-L19-vc-0101 and EDB-L19-vc-9411 showed tumor regression at the 3 mg/kg dose over time.

PDX-PAX-13565 and PDX-PAX-12534 Pancreatic PDXs

The anti-tumor efficacy of EDB-L19-vc-0101 was evaluated in human pancreatic PDX models. As shown in FIG. 8A, EDB-L19-vc-0101 was assessed at 0.3, 1 and 3 mg/kg in PDX-PAX-13565, a moderate to high EDB+ FN expressing pancreatic PDX. As shown in FIG. 8B, EDB-L19-vc-0101 was assessed at 0.3, 1 and 3 mg/kg in PDX-PAX-12534, a low to moderate EDB+ FN expressing pancreatic PDX. EDB-L19-vc-0101 demonstrated tumor regression in a dose dependent manner in both pancreatic PDX models evaluated.

Ramos Lymphoma CLX

The anti-tumor efficacy of EDB-L19-vc-0101 was evaluated in Ramos, a moderate EDB+FN expressing lymphoma CLX model. EDB-L19-vc-0101 was assessed for anti-tumor activity at 1 and 3 mg/kg. As shown in FIG. 9, EDB-L19-vc-0101 showed tumor regression at the 3 mg/kg dose in a dose dependent manner.

EMT-6 Breast Syngeneic Model

The anti-tumor efficacy of EDB-(κK183C-K94R-K290C)-vc-0101 was evaluated in EMT-6, a mouse syngeneic breast carcinoma model in an immunocompetent background. As shown in FIG. 10A, EDB-(κK183C-K94R-K290C)-vc-0101 demonstrated tumor growth inhibition at 4.5 mg/kg. The tumor growth inhibition was plotted as an average of tumor size in eleven tumor bearing animals ±SEM. FIG. 10B shows the tumor growth inhibition curves for the 11 individual tumor bearing mice in the EDB-(κK183C-K94R-K290C)-vc-0101 group dosed at 4.5 mg/kg. The tumor regressions in the 4.5 mg/kg group were complete and durable in 9 of 11 mice (82%) at the end of the study (34 days).

Ovarian

The activity of EDB-(κK183C-K94R-K290C)-vc-0101 was examined in ovarian and breast carcinoma human PDX models which express EDB+ FN. Activity has been observed at 3 mg/kg and 10 mg/kg dose levels (data not shown).

Example 9

Pharmacokinetics (PK)

Exposure of conventionally conjugated EDB-L19-vc-0101 and site-specific conjugated EDB-(κK183C-K94R-K290C)-vc-0101 conjugated antibody drug conjugates were determined after an intravenous (IV) bolus dose administration of either 5 or 6 mg/kg in cynomolgus monkeys, respectively. Concentrations of total antibody (total Ab; measurement of both conjugated mAb and unconjugated mAb), ADC (mAb that is conjugated to at least one drug molecule) were measured using ligand binding assays (LBA) and concentrations of the released payload 0101 were measured using mass spectrometry. Quantitation of total Ab and ADC concentrations was achieved by ligand binding assay (LBA) using the GYROLAB® (Gyros AB) immunoassay workstation with fluorescence detection. The Biotinylated capture protein used was a sheep anti-hIgG and the detection antibody was ALEXA FLUOR® 647 (Molecular Probes, Inc., fluorescent chemicals and biomolecule labeling kits) goat anti-hIgG for total antibody or ALEXA FLUOR® 647 (Molecular Probes, Inc., fluorescent chemicals and biomolecule labeling kits) anti-0101 mAb for ADC (data was processed by the Watson v 7.4 LIMS system). In vivo samples were prepared for unconjugated payload analysis using protein precipitation and injected onto an AB Sciex API5500 (QTRAP) mass spectrometer using positive Turbo IonSpray electrospray ionization (ESI) and multiple reaction monitoring (MRM) mode. The transitions of 743.6→188.0 and 751.6→188.0 were used for the analyte and deuterated internal standard, respectively. Data acquisition and processing were carried out with Analyst software version 1.5.2 (Applied Biosystems/MDS Sciex, Canada).

The pharmacokinetics of total Ab, ADC and released payload from EDB-L19-vc-0101 ADC (at 5 mg/kg) and EDB-(κK183C-K94R-K290C)-vc-0101 ADC (6 mg/kg) dosed cynomolgus monkeys are shown in Table 22. Exposure of the site-specific conjugated EDB-(κK183C-K94R-K290C)-vc-0101 ADC showed both increased exposure (~2.3× increase as measured by dose normalized AUC) and increased conjugation stability when compared to the conventional conjugate. Conjugation stability was assessed by both the higher ADC/Ab ratio (84% versus 75%) and by the lower released payload exposure (dose normalized AUC; 0.0058 versus 0.0082 μg*h/mL) for the site-specific conjugated EDB-(κK183C-K94R-K290C)-vc-0101 ADC compared to the conventional EDB-L19-vc-0101 ADC, respectively. NA=not applicable.

TABLE 22

Summary of pharmacokinetics in non-human primates.

| ADC | Dose (mg/kg) | Analyte | $C_{max}$ (μg/mL) | $AUC_{0-504}$ (μg*hr/mL) | Terminal $T_{1/2}$ (day) | AUC/ Dose | ADC/Ab (%) |
|---|---|---|---|---|---|---|---|
| EDB-L19-vc-0101 (ADC1) | 5 | Ab | 114 ± 27 | 6907 ± 1997 | 5.1 ± 2.2 | 1381 ± 399 | — |
| | | ADC | 110 ± 31 | 5190 ± 1453 | 4.6 ± 1.0 | 1038 ± 291 | 75 ± 2 |
| | | Payload | 0.00053 ± 0.00025 | 0.0411 ± 0.0160 | NA | 0.0082 ± 0.0032 | — |
| EDB-(κK183C-K94R-K290C)-vc-0101 (ADC4) | 6 | Ab | 164 ± 36 | 17600 ± 3045 | 6.4 ± 1.3 | 2933 ± 507 | — |
| | | ADC | 156 ± 30 | 14567 ± 2122 | 5.9 ± 1.1 | 2428 ± 354 | 84 ± 3 |
| | | Payload | 0.00024 ± 0.00021 | 0.0349 ± 0.0030 | NA | 0.0058 ± 0.0005 | — |

Example 10

Thermal Stability Assessment for EDB ADCs

Differential Scanning calorimetry (DCS) was used to determine the thermal stability of the anti-EDB antibody variants and corresponding conventional and site-specific conjugated EDB ADCs. Samples formulated in PBS-CMF pH 7.2 were dispensed into the sample tray of a MicroCal VP-Capillary DSC with Autosampler (GE Healthcare BioSciences, Piscataway, NJ), equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, MA) was used to fit the data to an MN2-State Model with an appropriate number of transitions.

As shown in Table 23, various anti-EDB antibodies and EDB ADCs, using both site-specific and conventional conjugation technology, were evaluated and exhibited favorable thermal stability as determined by the first melting transition (Tm1)>65° C. These results demonstrate that the EDB-(κK183C-K94R-K290C antibody and κK183C-K94R-K290C-vc-0101 ADC incorporating engineered cysteine residues were thermally stable.

TABLE 23

Thermal Stability of EDB Antibody Variants and EDB ADCs

| | $T_m1$ | $T_m2$ | $T_m3$ |
|---|---|---|---|
| ADCs | | | |
| EDB-L19-vc-0101 | 66.00 ± 0.15 | 80.97 ± 0.25 | 84.11 ± 0.06 |
| EDB-(K94R)-vc-0101 | 65.61 ± 0.14 | 80.24 ± 0.22 | 83.43 ± 0.05 |
| EDB-(κK183C-K94R-K290C)-vc-0101 | 66.00 ± 0.10 | 80.24 ± 0.43 | 83.27 ± 0.10 |
| Antibodies | | | |
| EDB-(κK183C-K94R-K290C) | 75.28 ± 0.12 | 81.56 ± 0.37 | 84.24 ± 0.12 |
| EDB-L19 | 72* | 82* | 85* |

*Values determined in a different experiment from others reported in table

Example 11

Toxicity Studies

The nonclinical safety profile of conventional conjugated EDB-L19-vc-0101 and site-specific conjugated EDB-(κK183C-K94R-K290C)-vc-0101 was characterized in exploratory repeat-dose (Q3Wx3) studies in Wistar-Han rats and cynomolgus monkeys. The rat and cynomolgus monkey were considered pharmacologically relevant nonclinical species for toxicity evaluation due to 100% protein sequence homology with human EDB, as well as similar binding affinity of the antibodies EDB-L19 and EDB-(κK183C-K94R-K290C) to rat, human and monkey by BIACORE® (Cytiva; surface plasmon resonance (SPR) assay), as demonstrated in Example 2.

EDB-L19-vc-0101 was evaluated in Wistar Han rats and cynomolgus monkeys up to 10 and 5 mg/kg/dose, respectively, and EDB-(κK183C-K94R-K290C)-vc-0101 was evaluated in cynomolgus monkeys up to 12 mg/kg/dose. Rats or monkeys were dosed intravenously once every 3 weeks (on Days 1, 22 and 43) and were euthanized on Day 46 (3 days after the 3$^{rd}$ dose). Animals were evaluated for clinical signs, changes in body weight, food consumption, clinical pathology parameters, organ weights, and macroscopic and microscopic observations. No mortality or significant changes in clinical condition of animals were noted in these studies.

There was no indication of target-dependent toxicity in EDB+ FN expressing tissues/organs in rats and monkeys. In both species, the major toxicity was reversible myelosuppression with associated hematological changes. In monkeys, marked transient neutropenia was seen with conventionally conjugated EDB-L19-vc-0101 at 5 mg/kg/dose while only minimal effects on neutrophil counts were seen with site-specific conjugated EDB-(κK183C-K94R-K290C)-vc-0101 at 6 mg/kg/dose, as shown in Table 24 and FIG. 11. Points represent mean and error bars represent ±1 standard deviation (SD) from the mean.

The data demonstrates significant alleviation of myelosuppression by site-specific conjugation. The toxicity profile of EDB-L19-vc-0101 and EDB-(κK183C-K94R-K290C)-vc-0101 was consistent with target-independent effects of these conjugates and the highest non-severely toxic doses (HNSTD) for EDB-L19-vc-0101 and EDB-(κK183C-K94R-K290C)-vc-0101 were determined to be ≥5 mg/kg/dose and ≥12 mg/kg/dose, respectively.

TABLE 24

Absolute neutrophil counts in cynomolgus monkeys over the study duration.

| Day | 0 mg/kg (vehicle) | | EDB-L19-vc-0101 (5 mg/kg) | | EDB-(κK183C-K94R-K290C)-vc-0101 (6 mg/kg) | |
| --- | --- | --- | --- | --- | --- | --- |
| | Animal #1 | Animal #2 | Animal #1 | Animal #2 | Animal #1 | Animal #2 |
| −7 | 3.26 | 2.9 | 8.48 | 4.67 | 2.41 | 7.42 |
| 7 | 3.54 | 2.52 | 7.08 | 2.29 | 3.96 | 4.3 |
| 10 | 3.16 | 6.83 | 0.11 | 0.82 | 2.66 | 1.56 |
| 15 | 3.06 | 1.98 | 11.41 | 3.65 | 1.37 | 1.44 |
| 31 | 3.87 | 4.17 | 0.39 | 2.07 | 1.91 | 2.22 |
| 38 | 3.09 | 5.63 | 16.17 | 2.73 | 1.97 | 1.13 |
| 45 | 3.53 | 2.07 | 13.02 | 1.83 | 1.4 | 3.78 |

Example 12

IO Combinations

As cancer cells die, they release antigens that are taken up and presented by dendritic cells (DCs). Because of the mutations in these tumor cells some of these antigens include cancer neoepitopes which have the potential to be presented by the mature DCs to T cells, thereby activating them and inducing anti-tumor targeting. However, negative regulatory mechanisms are upregulated in cancer patients. For example, signaling through checkpoints such as the PD-1/PD-L1 pathways may limit the recognition of the neoepitopes and activation of T cells.

Payloads conjugated to antibodies in the ADC format may participate to engage the dendritic cell maturation pathways resulting in increased tumor antigen cross presentation, which allows for T cell priming and increased tumor T cell targeting. The EDB ADCs of the present invention, comprising various payloads such as Payload-0101, were utilized to improve immune recognition of tumor neoantigens by creating immunogenic tumor environments. These environments become responsive to immune-oncology agents that block the negative regulatory pathways, when the EDB ADC and immune-oncology agent is given in combination.

Data from efficacy studies of EMT6 syngeneic tumors treated with EDB-L19-vc-0101 suggests an effector response to Payload-0101 was induced. Increased infiltration of CD3+ T cells was observed in EDB-L19-vc-0101 treated tumors vs. vehicle controls. Additionally, increased expression of PDL1 in treated tumors was observed, suggesting IFNγ release due to the increased effector T cell response.

Combining EDB ADCs with agents that target immunomodulatory pathways, such as anti-PDL1 antagonist antibodies or anti-41BB agonist antibodies, will likely improve anti-tumor efficacy and provide more durable responses.

Example 13

Biomarker/Mechanism of Action

NSCLC PDX model PDX-NSX-11122 was developed in nude mice as previously described. EDB-(K94R)-vc-0101, EDB-(κK183C-K94R-K290C)-vc-0101, and Neg-vc-0101 ADC, were administered by tail vein injection at 3 mg/kg (4 animals per timepoint per group). At 96 hours after a single administration, animals were anaesthetized and were perfused with saline. Following saline perfusion, tumors were removed and prepared for measurement of antibody and ADC via ligand binding assay (LBA), or were prepared for immunohistochemistry (IHC).

Ligand Binding Assay (LBA)

For LBA assays, 5× buffer was added to the tumor samples. The tissue extraction reagent (Invitrogen) contained 1% protease inhibitor (Sigma), (v/w) with a final dilution of 6× (µg/mL homogenate→Tg/g tissue). Stainless steel beads were added and the tissue was homogenize using a Mini-Beadbeater-96 (BioSpec). The homogenate (~100-300 µL depending on sample size) was transferred to an appropriate vial (Marsh tube) and centrifuge at 14000 rpm for 10 minutes (4° C.). The centrifuged homogenate was diluted (MRD) with Super Block™ for analysis according to analytical protocol.

As shown in Table 25, ligand binding assays were used to determine mean total antibody and ADC plasma concentrations (µg/mL) tumor concentrations (µg/g) following the single dose administration of EDB ADCs. The data demonstrates that EDB-(K94R)-vc-0101 and EDB-(κK183C-K94R-K290C)-vc-0101 were detected at the site of the tumor at increased levels as measured by total antibody and ADC as compared to the Neg-vc-0101. Furthermore, there was a decreased plasma to tumor ratio for both the ADC and the total antibody observed for EDB-(K94R)-vc-0101 and EDB-(κK183C-K94R-K290C)-vc-0101 compared to Neg-vc-0101 indicating the increased efficiency of tumor specific targeting of EDB targeting ADCs.

TABLE X

Mean total Ab and ADC plasma and tumor concentrations in NSCLC PDX.

| ADC | Modality | Plasma at 96 hours (µg/mL) | Tumor at 96 hours (µg/g) | Plasma/Tumor ratio |
| --- | --- | --- | --- | --- |
| EDB-(K94R)-vc-0101 | Total Ab | 13.1 ± 3.7 | 10.2 ± 2.6 | 1.3 |
| | ADC | 12.0 ± 4.0 | 8.93 ± 1.77 | 1.3 |
| EDB-(κK183C-K94R-K290C)-vc-0101 | Total Ab | 10.3 ± 2.4 | 7.17 ± 2.40 | 1.4 |
| | ADC | 8.19 ± 2.03 | 6.01 ± 1.96 | 1.4 |
| Neg-vc-0101 | Total Ab | 24.2 ± 6.6 | 4.74 ± 0.84 | 5.1 |
| | ADC | 20.2 ± 5.8 | 3.67 ± 0.80 | 5.5 |

Immunohistochemistry (IHC)

For immunohistochemical detection of ADC distribution and downstream biomarkers of response, samples were fixed in 10% neutral buffered formalin for 48 hours. After fixation, samples were embedded in paraffin and sectioned at 5 µM. Cut paraffin section were deparaffinized in xylene substitute and rehydrated with graded alcohols to distilled water. Antigens were retrieved in: 10 mM Citrate buffer pH 6.0

(Invitrogen) for phospho-Histone H3 and cleaved caspase 3 detection or Borg Decloaker buffer pH 9.5 (Biocare Medical) for anti-human IgG detection and anti-0101 detection in a pressure cooker (Electron Microscopy Sciences) and cooled to room temperature. Endogenous peroxidase was blocked with 3% hydrogen peroxide for 10 minutes. Non-specific protein interactions were blocked with Protein block (DAKO) for 20 minutes. Tissue sections were incubated with primary antibody for 1 hour at room temperature. Primary antibodies were: 0.3 µg/mL anti-human Pan IgG antibody (Epitomics); 10 µg/mL anti-0101 Ab; 0.13 µg/mL anti-phospho Histone H3 (pHH3, Cell Signaling Technologies); 1.3 µg/mL anti-Cleaved Caspase 3 (Cell Signaling Technologies). To avoid mouse on mouse detection, anti-0101 isotype antibodies were labeled with ALEXA FLUOR® 488 using ALEXA FLUOR® 488 (Molecular Probes, Inc., fluorescent chemicals and biomolecule labeling kits) protein labeling kit (Life Technologies). Unlabeled primary antibodies were detected with SIGNALSTAIN® Boost reagent (Cell Signaling Technologies, HRP (Cell Signaling Technologies, modification-specific antibodies and reagents) for 30 minutes at room temperature. ALEXA FLUOR® 488 (Molecular Probes, Inc., fluorescent chemicals and biomolecule labeling kits) labeled primary antibodies were detected with 1 µg/ml rabbit anti-ALEXA FLUOR® 488 (Life Technologies) for 45 minutes at room temperature, followed by incubation with SIGNALSTAIN® Boost reagent (Cell Signaling Technologies, modification-specific antibodies and reagents) for 30 minutes at room temperature. DAB+ (3',3'-Diaminobenzidine; Dako) was used to develop color for 5 minutes. Sections were briefly counterstained in hematoxylin, washed in water, dehydrated in graded alcohols, cleared in xylene substitute, and cover-slipped with PERMOUNT® Mounting Medium (Fisher-Chemicals, mounting medium for microscope slides).

At 96 hours after a single dose, both the conventional EDB-(K94R)-vc-0101 and site-specific conjugated EDB-(κK183C-K94R-K290C)-vc-0101 were similarly detected by anti-human IgG IHC in the PDX-NSX-11122 PDX model. An increase in pHH3 positive cells, a marker of mitotic arrest, was observed in tumors treated with both EDB-(K94R)-vc-0101 and EDB-(κK183C-K94R-K290C)-vc-0101 compared to those treated with the negative control ADC (Neg-vc-0101). The majority of the cells harboring the pHH3 mitotic arrest marker were neoplastic cells, suggesting the bystander effect. Cleaved caspase 3 stain indicated increased apoptosis in those tumors treated with EDB-(K94R)-vc-0101 (and EDB-(κK183C-K94R-K290C)-vc-0101 compared to the tumors treated with the negative control ADC (Neg-vc-0101).

---

SEQUENCE LISTING

```
Sequence total quantity: 57
SEQ ID NO: 1              moltype = AA  length = 116
FEATURE                   Location/Qualifiers
REGION                    1..116
                          note = Synthetic peptide sequence
source                    1..116
                          mol_type = protein
                          organism = synthetic construct
SEQUENCE: 1
EVQLLESGGG LVQPGGSLRL SCAASGFTFS SFSMSWVRQA PGKGLEWVSS ISGSSGTTYY  60
ADSVKGRFTI SRDNSKNTLY LQMNSLRAED TAVYYCAKPF PYFDYWGQGT LVTVSS      116

SEQ ID NO: 2              moltype = DNA  length = 348
FEATURE                   Location/Qualifiers
misc_feature              1..348
                          note = Synthetic nucleotide sequence
source                    1..348
                          mol_type = other DNA
                          organism = synthetic construct
SEQUENCE: 2
gaggtgcagc tgttggagtc tgggggaggc ttggtacagc ctggggggtc cctgagactc  60
tcctgtgcag cctctggatt caccttagc agttttcga tgagctgggt ccgccaggct  120
ccagggaagg ggctggagtg ggtctcatct attagtggta gttcgggtac cacatactac  180
gcagactccg tgaagggccg gttcaccatc tccagagaca attccaagaa cacgctgtat  240
ctgcaaatga acagcctgag agccgaagac acggccgtat attactgtgc gaaaccgttt  300
ccgtattttg actactgggg ccagggaacc ctggtcaccg tctcgagt              348

SEQ ID NO: 3              moltype = AA  length = 5
FEATURE                   Location/Qualifiers
REGION                    1..5
                          note = Synthetic peptide sequence
source                    1..5
                          mol_type = protein
                          organism = synthetic construct
SEQUENCE: 3
SFSMS                                                              5

SEQ ID NO: 4              moltype = AA  length = 7
FEATURE                   Location/Qualifiers
REGION                    1..7
                          note = Synthetic peptide sequence
source                    1..7
                          mol_type = protein
                          organism = synthetic construct
SEQUENCE: 4
GFTFSSF                                                            7
```

```
SEQ ID NO: 5              moltype = AA   length = 17
FEATURE                   Location/Qualifiers
REGION                    1..17
                          note = Synthetic peptide sequence
source                    1..17
                          mol_type = protein
                          organism = synthetic construct
SEQUENCE: 5
SISGSSGTTY YADSVKG                                                        17

SEQ ID NO: 6              moltype = AA   length = 6
FEATURE                   Location/Qualifiers
REGION                    1..6
                          note = Synthetic peptide sequence
source                    1..6
                          mol_type = protein
                          organism = synthetic construct
SEQUENCE: 6
SGSSGT                                                                     6

SEQ ID NO: 7              moltype = AA   length = 7
FEATURE                   Location/Qualifiers
REGION                    1..7
                          note = Synthetic peptide sequence
source                    1..7
                          mol_type = protein
                          organism = synthetic construct
SEQUENCE: 7
PFPYFDY                                                                    7

SEQ ID NO: 8              moltype = AA   length = 446
FEATURE                   Location/Qualifiers
REGION                    1..446
                          note = Synthetic peptide sequence
source                    1..446
                          mol_type = protein
                          organism = synthetic construct
SEQUENCE: 8
EVQLLESGGG LVQPGGSLRL SCAASGFTFS SFSMSWVRQA PGKGLEWVSS ISGSSGTTYY          60
ADSVKGRFTI SRDNSKNTLY LQMNSLRAED TAVYYCAKPF PYFDYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKKVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSRDELTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPGK                                             446

SEQ ID NO: 9              moltype = DNA   length = 1338
FEATURE                   Location/Qualifiers
misc_feature              1..1338
                          note = Synthetic nucleotide sequence
source                    1..1338
                          mol_type = other DNA
                          organism = synthetic construct
SEQUENCE: 9
gaggtgcagc tgttggagtc tgggggaggc ttggtacagc ctgggggtc cctgagactc           60
tcctgtgcag cctctggatt cacctttagc agttttcga tgagctgggt ccgccaggct          120
ccagggaagg ggctggagtg ggtctcatct attagtggta gttcgggtac cacatactac         180
gcagactccg tgaagggccg gttcaccatc tccagagaca attccaagaa cacgctgtat         240
ctgcaaatga acagcctgag agccgaagac acggccgtat attactgtgc gaaaccgttt         300
ccgtattttg actactgggg ccagggaacc ctggtcaccg tctcgagtgc gtcgaccaag         360
ggcccatcgg tcttccccct ggcaccctcc tccaagagca cctctggggg cacagcggcc         420
ctgggctgcc tggtcaagga ctacttcccc gaaccggtga cggtgtcgtg gaactcaggc         480
gccctgacca gcggcgtgca caccttcccg gctgtcctac agtcctcagg actctactcc         540
ctcagcagcg tggtgaccgt gccctccagc agcttgggca cccagaccta catctgcaac         600
gtgaatcaca agcccagcaa caccaaggtg gacaagaaag ttgagcccaa atcttgtgac         660
aaaactcaca catgcccacc gtgcccagca cctgaactcc tggggggacc gtcagtcttc         720
ctcttccccc caaaacccaa ggacaccctc atgatctccc ggacccctga ggtcacatgc         780
gtggtggtgg acgtgagcca cgaagaccct gaggtcaagt tcaactggta cgtggacggc         840
gtggaggtgc ataatgccaa gacaaagccg cgggaggagc agtacaacag cacgtaccgt         900
gtggtcagcg tcctcaccgt cctgcaccag gactggctga atggcaagga gtacaagtgc         960
aaggtctcca acaaagccct cccagccccc atcgagaaaa ccatctccaa agccaaaggg        1020
cagccccgag aaccacaggt gtacaccctg cccccatccc gggatgagct gaccaagaac        1080
caggtcagcc tgacctgcct ggtcaaaggc ttctatccca gcgacatcgc cgtggagtgg        1140
gagagcaatg ggcagccgga gaacaactac aagaccacgc ctcccgtgct ggactccgac        1200
ggctccttct tcctctacag caagctcacc gtggacaaga gcaggtggca gcaggggaac        1260
gtcttctcat gctccgtgat gcatgaggct ctgcacaacc actacacgca gaagagcctc        1320
tccctgtctc cgggtaaa                                                     1338
```

```
SEQ ID NO: 10            moltype = AA   length = 108
FEATURE                  Location/Qualifiers
REGION                   1..108
                         note = Synthetic peptide sequence
source                   1..108
                         mol_type = protein
                         organism = synthetic construct
SEQUENCE: 10
EIVLTQSPGT LSLSPGERAT LSCRASQSVS SSFLAWYQQK PGQAPRLLIY YASSRATGIP   60
DRFSGSGSGT DFTLTISRLE PEDFAVYYCQ QTGRIPPTFG QGTKVEIK               108

SEQ ID NO: 11            moltype = DNA   length = 324
FEATURE                  Location/Qualifiers
misc_feature             1..324
                         note = Synthetic nucleotide sequence
source                   1..324
                         mol_type = other DNA
                         organism = synthetic construct
SEQUENCE: 11
gaaattgtgt taacgcagtc tccaggcacc ctgtctttgt ctccagggga aagagccacc   60
ctctcctgca gggccagtca gagtgttagc agcagctttt tagcctgggg ccagcagaaa  120
cctggccagg ctcccaggct cctcatctat tatgcatcca gcagggccac tggcatccca  180
gacaggttca gtggcagtgg gtctgggaca gacttcactc tcaccatcag cagactggag  240
cctgaagatt ttgcagtgta ttactgtcag cagacgggtc gtattccgcc gacgttcggc  300
caagggacca aggtggaaat caaa                                         324

SEQ ID NO: 12            moltype = AA   length = 12
FEATURE                  Location/Qualifiers
REGION                   1..12
                         note = Synthetic peptide sequence
source                   1..12
                         mol_type = protein
                         organism = synthetic construct
SEQUENCE: 12
RASQSVSSSF LA                                                       12

SEQ ID NO: 13            moltype = AA   length = 7
FEATURE                  Location/Qualifiers
REGION                   1..7
                         note = Synthetic peptide sequence
source                   1..7
                         mol_type = protein
                         organism = synthetic construct
SEQUENCE: 13
YASSRAT                                                              7

SEQ ID NO: 14            moltype = AA   length = 9
FEATURE                  Location/Qualifiers
REGION                   1..9
                         note = Synthetic peptide sequence
source                   1..9
                         mol_type = protein
                         organism = synthetic construct
SEQUENCE: 14
QQTGRIPPT                                                            9

SEQ ID NO: 15            moltype = AA   length = 215
FEATURE                  Location/Qualifiers
REGION                   1..215
                         note = Synthetic peptide sequence
source                   1..215
                         mol_type = protein
                         organism = synthetic construct
SEQUENCE: 15
EIVLTQSPGT LSLSPGERAT LSCRASQSVS SSFLAWYQQK PGQAPRLLIY YASSRATGIP   60
DRFSGSGSGT DFTLTISRLE PEDFAVYYCQ QTGRIPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 16            moltype = DNA   length = 645
FEATURE                  Location/Qualifiers
misc_feature             1..645
                         note = Synthetic nucleotide sequence
source                   1..645
                         mol_type = other DNA
                         organism = synthetic construct
SEQUENCE: 16
gaaattgtgt taacgcagtc tccaggcacc ctgtctttgt ctccagggga aagagccacc   60
```

```
ctctcctgca gggccagtca gagtgttagc agcagctttt tagcctggta ccagcagaaa    120
cctggccagg ctcccaggct cctcatctat tatgcatcca gcagggccac tggcatccca    180
gacaggttca gtggcagtgg gtctgggaca gacttcactc tcaccatcag cagactggag    240
cctgaagatt ttgcagtgta ttactgtcag cagacgggtc gtattccgcc gacgttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                   645

SEQ ID NO: 17          moltype = AA  length = 445
FEATURE                Location/Qualifiers
REGION                 1..445
                       note = Synthetic peptide sequence
source                 1..445
                       mol_type = protein
                       organism = synthetic construct
SEQUENCE: 17
EVQLLESGGG LVQPGGSLRL SCAASGFTFS SFSMSWVRQA PGKGLEWVSS ISGSSGTTYY     60
ADSVKGRFTI SRDNSKNTLY LQMNSLRAED TAVYYCAKPF PYFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 18          moltype = DNA  length = 1335
FEATURE                Location/Qualifiers
misc_feature           1..1335
                       note = Synthetic nucleotide sequence
source                 1..1335
                       mol_type = other DNA
                       organism = synthetic construct
SEQUENCE: 18
gaggtgcagc tgttggagtc tgggggaggc ttggtacagc ctggggggtc cctgagactc     60
tcctgtgcag cctctggatt cacctttagc agtttttcga tgagctgggt ccgccaggct    120
ccagggaagg ggctggagtg ggtctcatct attagtggta gttgggtac cacatactac    180
gcagactccg tgaagggccg gttcaccatc tccagagaca attccaagaa cacgctgtat    240
ctgcaaatga acagcctgag agccgaagac acggccgtat attactgtgc gaaaccgttt    300
ccgtatttg actactgggg ccaggaacc ctggtcaccg tctcgagtgc gtcgaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca cacctccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtccc cgggt                                                   1335

SEQ ID NO: 19          moltype = AA  length = 445
FEATURE                Location/Qualifiers
REGION                 1..445
                       note = Synthetic peptide sequence
source                 1..445
                       mol_type = protein
                       organism = synthetic construct
SEQUENCE: 19
EVQLLESGGG LVQPGGSLRL SCAASGFTFS SFSMSWVRQA PGKGLEWVSS ISGSSGTTYY     60
ADSVKGRFTI SRDNSKNTLY LQMNSLRAED TAVYYCAKPF PYFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTCP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 20          moltype = DNA  length = 1335
FEATURE                Location/Qualifiers
```

```
misc_feature         1..1335
                     note = Synthetic nucleotide sequence
source               1..1335
                     mol_type = other DNA
                     organism = synthetic construct
SEQUENCE: 20
gaggtgcagc tgttggagtc tgggggaggc ttggtacagc ctgggggtc  cctgagactc    60
tcctgtgcag cctctggatt cacctttagc agttttcga  tgagctgggt ccgccaggct   120
ccagggaagg ggctggagtg ggtctcatct attagtggta gttcgggtac cacatactac   180
gcagactccg tgaagggccg gttcaccatc tccagagaca attccaagaa cacgctgtat   240
ctgcaaatga acagcctgag agccgaagac acggccgtat attactgtgc gaaccgtttt   300
ccgtattttg actactgggg ccagggaacc ctggtcaccg tctcgagtgc gtcgaccaag   360
ggcccatcgg tcttcccct  ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacatgcccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag caagctcacc gtggacaaga gcaggtggca gcaggggaac  1260
gtcttctcat gctccgtgat gcatgaggct ctgcacaacc actacacgca gaagagcctc  1320
tccctgtccc cgggt                                                   1335

SEQ ID NO: 21         moltype = AA  length = 116
FEATURE               Location/Qualifiers
REGION                1..116
                      note = Synthetic peptide sequence
source                1..116
                      mol_type = protein
                      organism = synthetic construct
SEQUENCE: 21
EVQLLESGGG LVQPGGSLRL SCAASGFTFS SFSMSWVRQA PGKGLEWVSS ISGSSGTTYY    60
ADSVKGRFTI SRDNSKNTLY LQMNSLRAED TAVYYCARPF PYFDYWGQGT LVTVSS       116

SEQ ID NO: 22         moltype = DNA  length = 348
FEATURE               Location/Qualifiers
misc_feature          1..348
                      note = Synthetic nucleotide sequence
source                1..348
                      mol_type = other DNA
                      organism = synthetic construct
SEQUENCE: 22
gaggtgcagc tgttggagtc tgggggaggc ttggtacagc ctgggggtc  cctgagactc    60
tcctgtgcag cctctggatt cacctttagc agttttcga  tgagctgggt ccgccaggct   120
ccagggaagg ggctggagtg ggtctcatct attagtggta gttcgggtac cacatactac   180
gcagactccg tgaagggccg gttcaccatc tccagagaca attccaagaa cacgctgtat   240
ctgcaaatga acagcctgag agccgaagac acggccgtat attactgtgc gagaccgttt   300
ccgtattttg actactgggg ccagggaacc ctggtcaccg tctcgagt              348

SEQ ID NO: 23         moltype = AA  length = 445
FEATURE               Location/Qualifiers
REGION                1..445
                      note = Synthetic peptide sequence
source                1..445
                      mol_type = protein
                      organism = synthetic construct
SEQUENCE: 23
EVQLLESGGG LVQPGGSLRL SCAASGFTFS SFSMSWVRQA PGKGLEWVSS ISGSSGTTYY    60
ADSVKGRFTI SRDNSKNTLY LQMNSLRAED TAVYYCARPF PYFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 24         moltype = DNA  length = 1335
FEATURE               Location/Qualifiers
misc_feature          1..1335
                      note = Synthetic nucleotide sequence
source                1..1335
                      mol_type = other DNA
```

```
                        organism = synthetic construct
SEQUENCE: 24
gaggtgcagc tgttggagtc tgggggaggc ttggtacagc ctgggggtc cctgagactc    60
tcctgtgcag cctctggatt cacctttagc agttttcga tgagctgggt ccgccaggct   120
ccagggaagg ggctggagtg ggtctcatct attagtggta gttcgggtac acatactac   180
gcagactccg tgaagggccg gttcaccatc tccagagaca attccaagaa cacgctgtat   240
ctgcaaatga acagcctgag agccgaagac acggccgtat attactgtgc gagaccgttt   300
ccgtattttg actactgggg ccagggaacc ctggtcaccg tctcgagtgc gtcgaccaag   360
ggcccatcgg tcttcccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag caagctcacc gtggacaaga gcaggtggca gcaggggaac  1260
gtcttctcat gctccgtgat gcatgaggct ctgcacaacc actacacgca gaagagcctc  1320
tccctgtccc cgggt                                                   1335

SEQ ID NO: 25           moltype = AA   length = 445
FEATURE                 Location/Qualifiers
REGION                  1..445
                        note = Synthetic peptide sequence
source                  1..445
                        mol_type = protein
                        organism = synthetic construct
SEQUENCE: 25
EVQLLESGGG LVQPGGSLRL SCAASGFTFS SFSMSWVRQA PGKGLEWVSS ISGSSGTTYY    60
ADSVKGRFTI SRDNSKNTLY LQMNSLRAED TAVYYCARPF PYFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTCP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 26           moltype = DNA   length = 1335
FEATURE                 Location/Qualifiers
misc_feature            1..1335
                        note = Synthetic nucleotide sequence
source                  1..1335
                        mol_type = other DNA
                        organism = synthetic construct
SEQUENCE: 26
gaggtgcagc tgttggagtc tgggggaggc ttggtacagc ctgggggtc cctgagactc    60
tcctgtgcag cctctggatt cacctttagc agttttcga tgagctgggt ccgccaggct   120
ccagggaagg ggctggagtg ggtctcatct attagtggta gttcgggtac acatactac   180
gcagactccg tgaagggccg gttcaccatc tccagagaca attccaagaa cacgctgtat   240
ctgcaaatga acagcctgag agccgaagac acggccgtat attactgtgc gagaccgttt   300
ccgtattttg actactgggg ccagggaacc ctggtcaccg tctcgagtgc gtcgaccaag   360
ggcccatcgg tcttcccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacatgcccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag caagctcacc gtggacaaga gcaggtggca gcaggggaac  1260
gtcttctcat gctccgtgat gcatgaggct ctgcacaacc actacacgca gaagagcctc  1320
tccctgtccc ccgga                                                   1335

SEQ ID NO: 27           moltype = AA   length = 445
FEATURE                 Location/Qualifiers
REGION                  1..445
                        note = Synthetic peptide sequence
```

```
source                  1..445
                        mol_type = protein
                        organism = synthetic construct
SEQUENCE: 27
EVQLLESGGG LVQPGGSLRL SCAASGFTFS SFSMSWVRQA PGKGLEWVSS ISGSSGTTYY    60
ADSVKGRFTI SRDNSKNTLY LQMNSLRAED TAVYYCAKPF PYFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD RTHTCPPCPA PELLGGPSVF   240
LFPPKPKDTL MISRTPEVTC VVVDVSHEDP EVKFNWYVDG VEVHNAKTKP RELLQGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 28           moltype = DNA  length = 1335
FEATURE                 Location/Qualifiers
misc_feature            1..1335
                        note = Synthetic nucleotide sequence
source                  1..1335
                        mol_type = other DNA
                        organism = synthetic construct
SEQUENCE: 28
gaggtgcagc tgttggagtc tgggggaggc ttggtacagc ctggggggtc cctgagactc     60
tcctgtgcag cctctggatt cacctttagc agttttttcga tgagctgggt ccgccaggct   120
ccagggaagg ggctggagtg ggtctcatct attagtggta gttcgggtac acatactac     180
gcagactccg tgaagggccg gttcaccatc tccagagaca attccaagaa cacgctgtat    240
ctgcaaatga acagcctgag agccgaagac acggccgtat attactgtgc gaaaccgttt    300
ccgtattttg actactgggg ccagggaacc ctggtcaccg tctcgagtgc gtcgaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tagtgaccgt gccctccagc agcttgggca cccagaccta catctgcaac    600
gtgaatcaca agcccagcaa caccaaggtg gacaagaaag ttgagcccaa atcttgtgac    660
cgcactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggctgc tgcaggggag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtctc cgggt                                                    1335

SEQ ID NO: 29           moltype = AA  length = 445
FEATURE                 Location/Qualifiers
REGION                  1..445
                        note = Synthetic peptide sequence
source                  1..445
                        mol_type = protein
                        organism = synthetic construct
SEQUENCE: 29
EVQLLESGGG LVQPGGSLRL SCAASGFTFS SFSMSWVRQA PGKGLEWVSS ISGSSGTTYY    60
ADSVKGRFTI SRDNSKNTLY LQMNSLRAED TAVYYCARPF PYFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD RTHTCPPCPA PELLGGPSVF   240
LFPPKPKDTL MISRTPEVTC VVVDVSHEDP EVKFNWYVDG VEVHNAKTKP RELLQGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 30           moltype = DNA  length = 1335
FEATURE                 Location/Qualifiers
misc_feature            1..1335
                        note = Synthetic nucleotide sequence
source                  1..1335
                        mol_type = other DNA
                        organism = synthetic construct
SEQUENCE: 30
gaggtgcagc tgttggagtc tgggggaggc ttggtacagc ctggggggtc cctgagactc     60
tcctgtgcag cctctggatt cacctttagc agttttttcga tgagctgggt ccgccaggct   120
ccagggaagg ggctggagtg ggtctcatct attagtggta gttcgggtac acatactac     180
gcagactccg tgaagggccg gttcaccatc tccagagaca attccaagaa cacgctgtat    240
ctgcaaatga acagcctgag agccgaagac acggccgtat attactgtgc gagaccgttt    300
ccgtattttg actactgggg ccagggaacc ctggtcaccg tctcgagtgc gtcgaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
```

-continued

```
ctcagcagcg tagtgaccgt gccctccagc agcttgggca cccagaccta catctgcaac    600
gtgaatcaca agcccagcaa caccaaggtg gacaagaaag ttgagcccaa atcttgtgac    660
cgcactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agcaggggag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctatag caagctcacc gtggacaaga gcaggtggca gcaggggaac   1260
gtcttctcat gctccgtgat gcatgaggct ctgcacaacc actacacgca gaagagcctc   1320
tccctgtccc ccgga                                                    1335

SEQ ID NO: 31        moltype = AA  length = 215
FEATURE              Location/Qualifiers
REGION               1..215
                     note = Synthetic peptide sequence
source               1..215
                     mol_type = protein
                     organism = synthetic construct
SEQUENCE: 31
EIVLTQSPGT LSLSPGERAT LSCRASQSVS SSFLAWYQQK PGQAPRLLIY YASSRATGIP     60
DRFSGSGSGT DFTLTISRLE PEDFAVYYCQ QTGRIPPTFG QGTKVEIKRT VAAPSVFIFP    120
PSDEQLKSGT ASVVCLLNNF YPREAKVQWK VDNALQSGNS QESVTEQDSK DSTYSLSSTL    180
TLSCADYEKH KVYACEVTHQ GLSSPVTKSF NRGEC                               215

SEQ ID NO: 32        moltype = DNA  length = 645
FEATURE              Location/Qualifiers
misc_feature         1..645
                     note = Synthetic nucleotide sequence
source               1..645
                     mol_type = other DNA
                     organism = synthetic construct
SEQUENCE: 32
gaaattgtgt taacgcagtc tccaggcacc ctgtctttgt ctccagggga aagagccacc     60
ctctcctgca gggccagtca gagtgttagc agcagctttt tagcctggta ccagcagaaa    120
cctggccagg ctcccaggct cctcatctat tatgcatcca gcagggccac tggcatccca    180
gacaggttca gtggcagtgg gtctgggaca gacttcactc tcaccatcag cagactggag    240
cctgaagatt ttgcagtgta ttactgtcag cagacgggtc gtattccgcc gacgttcggc    300
caagggacca aggtggaaat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagct cgcagactac gagaaacac aaagtctacg cctgcgaagt cacccatcag    600
ggcctgagct cgcccgtcac aaagagcttc aacagggaga gtgt                     645

SEQ ID NO: 33        moltype = AA  length = 91
FEATURE              Location/Qualifiers
source               1..91
                     mol_type = protein
                     organism = Homo sapiens
SEQUENCE: 33
EVPQLTDLSF VDITDSSIGL RWTPLNSSTI IGYRITVVAA GEGIPIFEDF VDSSVGYYTV     60
TGLEPGIDYD ISVITLINGG ESAPTTLTQQ T                                    91

SEQ ID NO: 34        moltype = AA  length = 374
FEATURE              Location/Qualifiers
REGION               1..374
                     note = Synthetic peptide sequence
source               1..374
                     mol_type = protein
                     organism = synthetic construct
SEQUENCE: 34
VVTQLSPPTN LHLEANPDTG VLAVSWERST TPDITGYRIT TPTNGQQGN SLEEVVHADQ      60
SSCTFDNLSP GLEYNVSVYT VKDDKESVPI SDTIIPEVPQ LTDLSFVDIT DSSIGLRWTP    120
LNSSTIIGYR ITVVAAGEGI PIFEDFVDSS VGYYTVTGLE PGIDYDISVI TLINGGESAP    180
TTLTQQTAVP PPTDLRFTNI GPDTMRVTWA PPPSIDLTNF LVRYSPVKNE EDVAELSISP    240
SDNAVVLTNL LPGTEYVVSV SSVYEQHEST PLRGRQKTGL DSPTGIDFSD ITANSFTVHW    300
IAPRATITGY RIRHHPEHFS GRPREDRVPH SRNSITLTNL TPGTEYVVSI VALNGREESP    360
LLIGRSRSHH HHHH                                                      374

SEQ ID NO: 35        moltype = AA  length = 374
FEATURE              Location/Qualifiers
REGION               1..374
                     note = Synthetic peptide sequence
source               1..374
                     mol_type = protein
```

```
                        organism = synthetic construct
SEQUENCE: 35
VVTPLSPPTN LHLETNPDTG VLTVSWERST TPDITGYRIT TTPTNGQQGY SLEEVVHADQ    60
SSCTFDNLSP GLEYNVSVYT VKDDKESVPI SDTIIPEVPQ LTDLSFVDIT DSSIGLRWTP   120
LNSSTIIGYR ITVVAAGEGI PIFEDFVDSS VGYYTVTGLE PGIDYDISVI TLINGGESAP   180
TTLTQQTAVP PPTDLRFTNI GPDTMRVTWA PPPSIDLTNF LVRYSPVKNE EDVAELSISP   240
SDNAVVLTNL LPGTEYVVSV SSVYEQHEST PLRGRQKTGL DSPTGIDFSD ITANSFTVHW   300
IAPRATITGY RIRHHPEHMS GRPREDRVPP SRNSITLTNL TPGTEYVVSI VALNGREESP   360
LLIGRSRSHH HHHH                                                    374

SEQ ID NO: 36           moltype = AA  length = 374
FEATURE                 Location/Qualifiers
REGION                  1..374
                        note = Synthetic peptide sequence
source                  1..374
                        mol_type = protein
                        organism = synthetic construct
SEQUENCE: 36
VVTPLSPPTN LHLEANPDTG VLTVSWERST TPDITGYRIT TTPTNGQQGT ALEEVVHADQ    60
SSCTFENLNP GLEYNVSVYT VKDDKESAPI SDTVIPEVPQ LTDLSFVDIT DSSIGLRWTP   120
LNSSTIIGYR ITVVAAGEGI PIFEDFVDSS VGYYTVTGLE PGIDYDISVI TLINGGESAP   180
TTLTQQTAVP PPTDLRFTNI GPDTMRVTWA PPPSIELTNL LVRYSPVKNE EDVAELSISP   240
SDNAVVLTNL LPGTEYLVSV SSVYEQHESI PLRGRQKTGL DSPTGFDSSD VTANSFTVHW   300
VAPRAPITGY IIRHHAEHSA GRPRQDRVPP SRNSITLTNL NPGTEYIVTI IAVNGREESP   360
PLIGRSRSHH HHHH                                                    374

SEQ ID NO: 37           moltype = AA  length = 107
FEATURE                 Location/Qualifiers
REGION                  1..107
                        note = Synthetic peptide sequence
source                  1..107
                        mol_type = protein
                        organism = synthetic construct
SEQUENCE: 37
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 38           moltype = AA  length = 106
FEATURE                 Location/Qualifiers
REGION                  1..106
                        note = Synthetic peptide sequence
source                  1..106
                        mol_type = protein
                        organism = synthetic construct
SEQUENCE: 38
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTECS                 106

SEQ ID NO: 39           moltype = AA  length = 5
FEATURE                 Location/Qualifiers
REGION                  1..5
                        note = Synthetic peptide sequence
source                  1..5
                        mol_type = protein
                        organism = synthetic construct
SEQUENCE: 39
LLQGG                                                                5

SEQ ID NO: 40           moltype = AA  length = 4
FEATURE                 Location/Qualifiers
REGION                  1..4
                        note = Synthetic peptide sequence
source                  1..4
                        mol_type = protein
                        organism = synthetic construct
SEQUENCE: 40
LLQG                                                                 4

SEQ ID NO: 41           moltype = AA  length = 6
FEATURE                 Location/Qualifiers
REGION                  1..6
                        note = Synthetic peptide sequence
source                  1..6
                        mol_type = protein
                        organism = synthetic construct
SEQUENCE: 41
LSLSQG                                                               6

SEQ ID NO: 42           moltype = AA  length = 8
```

```
                        -continued

FEATURE          Location/Qualifiers
REGION           1..8
                 note = Synthetic peptide sequence
source           1..8
                 mol_type = protein
                 organism = synthetic construct
SEQUENCE: 42
GGGLLQGG                                                              8

SEQ ID NO: 43    moltype = AA  length = 5
FEATURE          Location/Qualifiers
REGION           1..5
                 note = Synthetic peptide sequence
source           1..5
                 mol_type = protein
                 organism = synthetic construct
SEQUENCE: 43
GLLQG                                                                 5

SEQ ID NO: 44    moltype = AA  length = 10
FEATURE          Location/Qualifiers
REGION           1..10
                 note = Synthetic peptide sequence
source           1..10
                 mol_type = protein
                 organism = synthetic construct
SEQUENCE: 44
GSPLAQSHGG                                                           10

SEQ ID NO: 45    moltype = AA  length = 7
FEATURE          Location/Qualifiers
REGION           1..7
                 note = Synthetic peptide sequence
source           1..7
                 mol_type = protein
                 organism = synthetic construct
SEQUENCE: 45
GLLQGGG                                                               7

SEQ ID NO: 46    moltype = AA  length = 6
FEATURE          Location/Qualifiers
REGION           1..6
                 note = Synthetic peptide sequence
source           1..6
                 mol_type = protein
                 organism = synthetic construct
SEQUENCE: 46
GLLQGG                                                                6

SEQ ID NO: 47    moltype = AA  length = 4
FEATURE          Location/Qualifiers
REGION           1..4
                 note = Synthetic peptide sequence
source           1..4
                 mol_type = protein
                 organism = synthetic construct
SEQUENCE: 47
GLLQ                                                                  4

SEQ ID NO: 48    moltype = AA  length = 8
FEATURE          Location/Qualifiers
REGION           1..8
                 note = Synthetic peptide sequence
source           1..8
                 mol_type = protein
                 organism = synthetic construct
SEQUENCE: 48
LLQLLQGA                                                              8

SEQ ID NO: 49    moltype = AA  length = 5
FEATURE          Location/Qualifiers
REGION           1..5
                 note = Synthetic peptide sequence
source           1..5
                 mol_type = protein
                 organism = synthetic construct
SEQUENCE: 49
LLQGA                                                                 5
```

```
SEQ ID NO: 50            moltype = AA  length = 7
FEATURE                  Location/Qualifiers
REGION                   1..7
                         note = Synthetic peptide sequence
source                   1..7
                         mol_type = protein
                         organism = synthetic construct
SEQUENCE: 50
LLQYQGA                                                                  7

SEQ ID NO: 51            moltype = AA  length = 6
FEATURE                  Location/Qualifiers
REGION                   1..6
                         note = Synthetic peptide sequence
source                   1..6
                         mol_type = protein
                         organism = synthetic construct
SEQUENCE: 51
LLQGSG                                                                   6

SEQ ID NO: 52            moltype = AA  length = 6
FEATURE                  Location/Qualifiers
REGION                   1..6
                         note = Synthetic peptide sequence
source                   1..6
                         mol_type = protein
                         organism = synthetic construct
SEQUENCE: 52
LLQYQG                                                                   6

SEQ ID NO: 53            moltype = AA  length = 7
FEATURE                  Location/Qualifiers
REGION                   1..7
                         note = Synthetic peptide sequence
source                   1..7
                         mol_type = protein
                         organism = synthetic construct
SEQUENCE: 53
LLQLLQG                                                                  7

SEQ ID NO: 54            moltype = AA  length = 5
FEATURE                  Location/Qualifiers
REGION                   1..5
                         note = Synthetic peptide sequence
source                   1..5
                         mol_type = protein
                         organism = synthetic construct
SEQUENCE: 54
SLLQG                                                                    5

SEQ ID NO: 55            moltype = AA  length = 5
FEATURE                  Location/Qualifiers
REGION                   1..5
                         note = Synthetic peptide sequence
source                   1..5
                         mol_type = protein
                         organism = synthetic construct
SEQUENCE: 55
LLQLQ                                                                    5

SEQ ID NO: 56            moltype = AA  length = 6
FEATURE                  Location/Qualifiers
REGION                   1..6
                         note = Synthetic peptide sequence
source                   1..6
                         mol_type = protein
                         organism = synthetic construct
SEQUENCE: 56
LLQLLQ                                                                   6
```

-continued

```
SEQ ID NO: 57          moltype = AA  length = 5
FEATURE                Location/Qualifiers
REGION                 1..5
                       note = Synthetic peptide sequence
source                 1..5
                       mol_type = protein
                       organism = synthetic construct
SEQUENCE: 57
LLQGR                                                                    5
```

What is claimed is:

1. An antibody-drug conjugate comprising:
   (a) an antibody, or antigen binding fragment thereof, that binds to extra domain B of fibronectin and that comprises:
      a heavy chain, the heavy chain comprising a constant region and a variable region, wherein the heavy chain variable region comprises SEQ ID NO:21; and
      a light chain, the light chain comprising a constant region and a variable region, wherein the light chain variable region comprises SEQ ID NO:10;
   (b) a linker; and
   (c) a drug.

2. The antibody-drug conjugate of claim 1, wherein the drug is a cytotoxic agent.

3. The antibody-drug conjugate of claim 1, wherein the antibody, or antigen binding fragment thereof, comprises at least one of the following:
   a cysteine at position 290 of the heavy chain constant region according to the numbering of the EU index;
   a cysteine at position 183 of the light chain constant region according to the numbering of the EU index.

4. The antibody-drug conjugate of claim 1, wherein the antibody comprises at least one of the following:
   a heavy chain comprising SEQ ID NO:25;
   a light chain comprising SEQ ID NO:31.

5. The antibody-drug conjugate of claim 1, wherein the linker is a cleavable linker.

6. The antibody-drug conjugate of claim 5, wherein the cleavable linker has the structure:

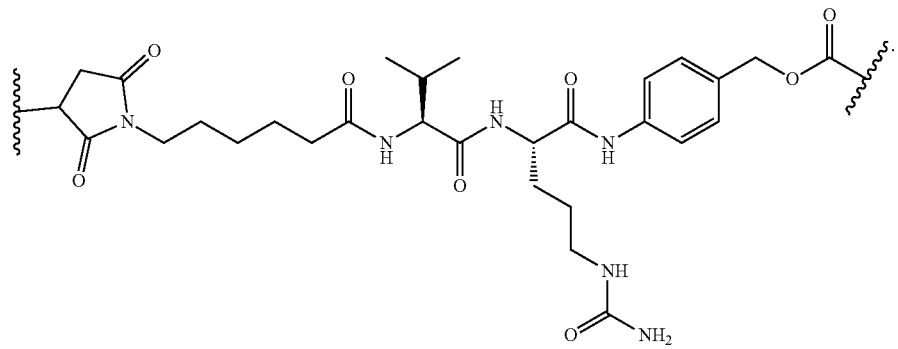 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

7. The antibody-drug conjugate of claim 2, wherein the cytotoxic agent is an auristatin.

8. The antibody-drug conjugate of claim 7, wherein the auristatin is auristatin 0101.

9. The antibody-drug conjugate of claim 2, wherein the cytotoxic agent has the structure:

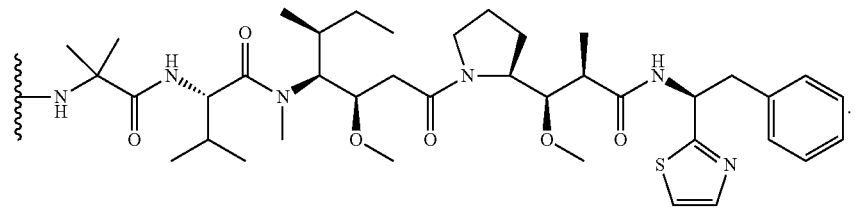 [SMILES: *NC(C)(C)C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)c1nccs1)OC)C(C)C]

10. The antibody-drug conjugate of claim 2, wherein the cytotoxic agent, the linker, and the antibody, or antigen binding fragment thereof, are linked to generate the structure:

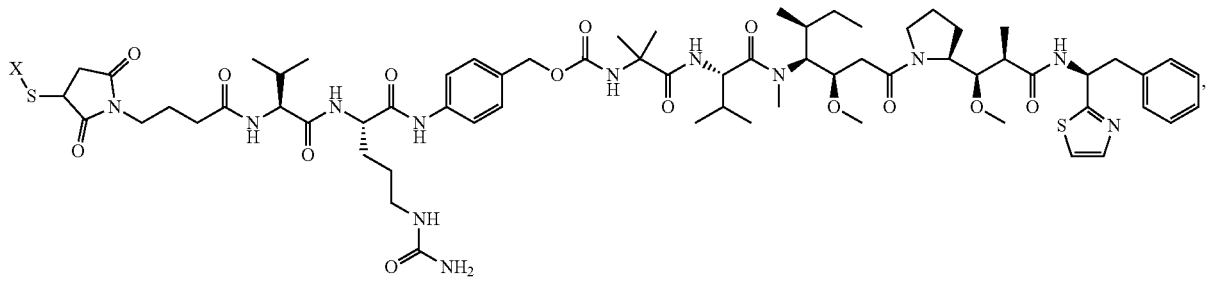

wherein:
X—S represents the antibody, or antigen binding fragment thereof, wherein S is the sulfur atom of at least one cysteine residue in the antibody, or antigen binding fragment thereof.

11. The antibody-drug conjugate of claim 1, wherein the drug is a detectable label or imaging agent.

12. The antibody-drug conjugate of claim 1, wherein the antibody, or antigen binding fragment thereof, further comprises:
a cysteine at position 290 of the heavy chain constant region according to the numbering of the EU index; and
a cysteine at position 183 of the light chain constant region according to the numbering of the EU index.

13. The antibody-drug conjugate of claim 1, wherein the antibody comprises:
a heavy chain comprising SEQ ID NO:25; and
a light chain comprising SEQ ID NO:31.

14. The antibody-drug conjugate of claim 5, wherein the cleavable linker is selected from the group consisting of:
vc having the structure

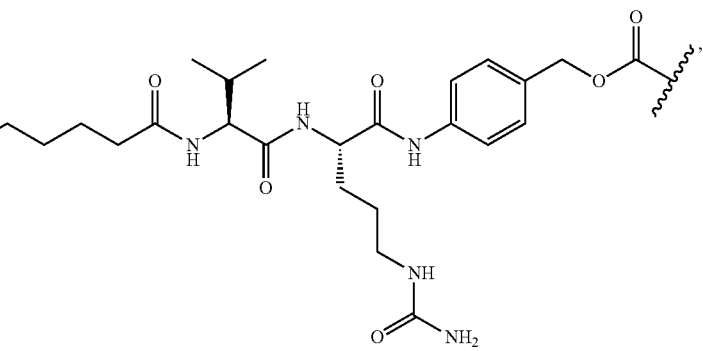

diS having the structure

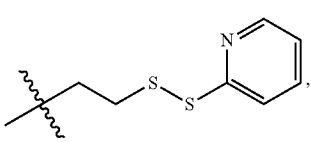 [SMILES: *CCSSc1ccccn1]

diS-C$_2$OCO having the structure
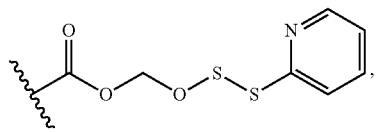 [SMILES: *C(=O)OCOSSc1ccccn1]
and
AcLys-vc having the structure
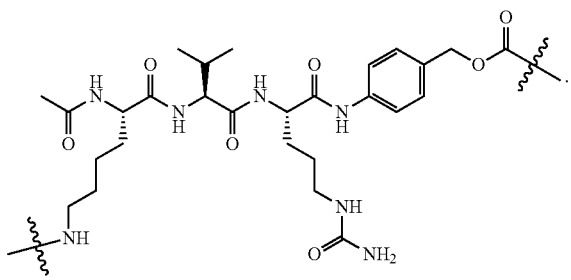 [SMILES: *NCCCC[C@H](NC(C)=O)C(=O)N[C@H](C(=O)N[C@@H](CCCNC(N)=O)C(=O)Nc1ccc(COC(*)=O)cc1)C(C)C]
15. The antibody-drug conjugate of claim 7, wherein the auristatin is selected from the group consisting of:
0101 having the structure
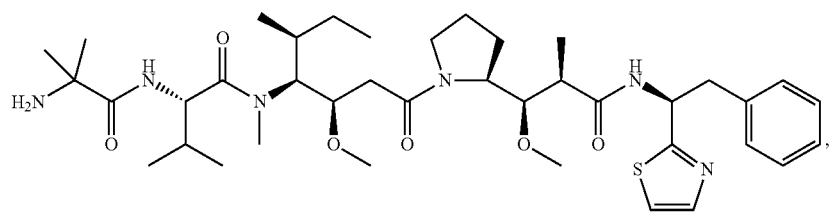 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]
1569 having the structure
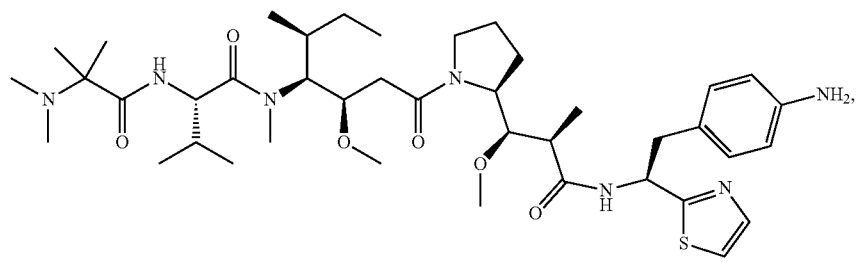 [SMILES: CC[C@H](C)[C@@H]([C@@H](CC(=O)N1CCC[C@H]1[C@H](OC)[C@@H](C)C(=O)N[C@@H](Cc1ccc(N)cc1)c1nccs1)OC)N(C)C(=O)[C@@H](NC(=O)C(C)(C)N(C)C)C(C)C]
9411 having the structure
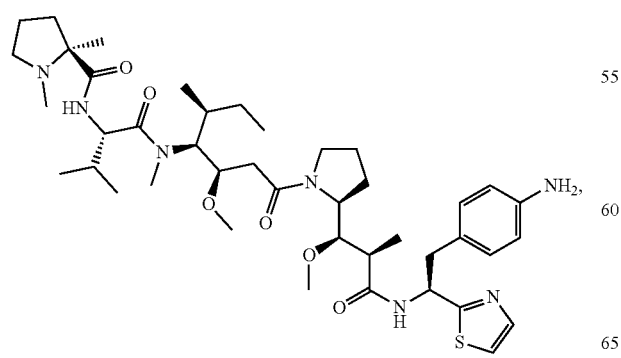

and
4574 having the structure

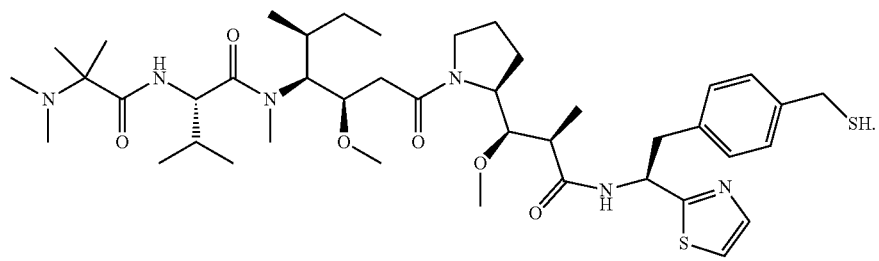 [SMILES: CC[C@H](C)[C@@H]([C@@H](CC(=O)N1CCC[C@H]1[C@H](OC)[C@@H](C)C(=O)N[C@@H](Cc1ccc(CS)cc1)c1nccs1)OC)N(C)C(=O)[C@@H](NC(=O)C(C)(C)N(C)C)C(C)C]

16. A composition comprising the antibody-drug conjugate of claim 1 and a pharmaceutically acceptable carrier.

17. A composition comprising a plurality of the antibody-drug conjugate of claim 1, wherein the composition has an average drug-to-antibody ratio (DAR) ranging from 3 to 5.

18. An antibody-drug conjugate comprising:
(a) an antibody, or antigen binding fragment thereof, that binds to extra domain B of fibronectin and that comprises a heavy chain comprising SEQ ID NO:25 and a light chain comprising SEQ ID NO: 31;
(b) a cleavable linker and a cytotoxic agent,
wherein the cleavable linker, the cytotoxic agent, and the antibody, or antigen binding fragment thereof, are linked to generate the structure:

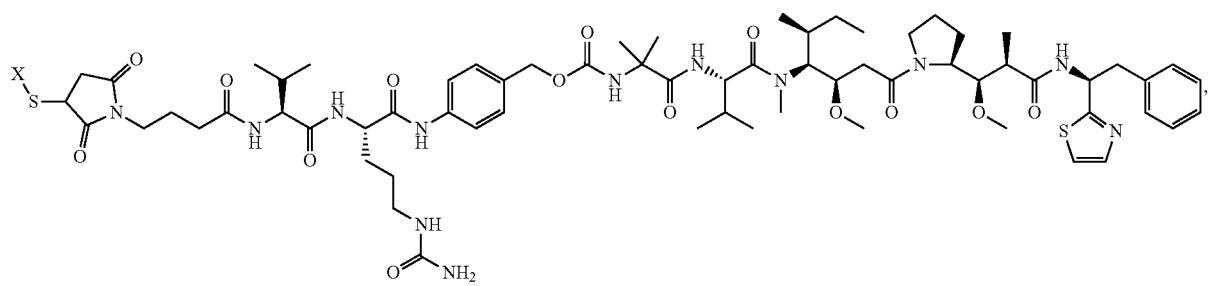

wherein:
X—S represents the antibody, or antigen binding fragment thereof, and S is the sulfur atom of at least one cysteine residue in the antibody, or antigen binding fragment thereof.

19. An antibody, or antigen binding fragment thereof, that binds to extra domain B of fibronectin, comprising:
a heavy chain, the heavy chain comprising a constant region and a variable region, wherein the heavy chain variable region comprises SEQ ID NO:21; and
a light chain, the light chain comprising a constant region and a variable region, wherein the light chain variable region comprises SEQ ID NO: 10.

20. The antibody, or antigen binding fragment thereof, of claim 19, comprising at least one of the following:
a cysteine at position 290 of the heavy chain constant region according to the numbering of the EU index;
a cysteine at position 183 of the light chain constant region according to the numbering of the EU index.

21. The antibody, or antigen binding fragment thereof, of claim 19, wherein the antibody, or antigen binding fragment thereof, comprises at least one of the following:

a heavy chain comprising SEQ ID NO:25;
a light chain comprising SEQ ID NO:31.

22. The antibody, or antigen binding fragment thereof, of claim 19, further comprising:
a cysteine at position 290 of the heavy chain constant region according to the numbering of the EU index; and
a cysteine at position 183 of the light chain constant region according to the numbering of the EU index.

23. The antibody, or antigen binding fragment thereof, of claim 19, wherein the antibody, or antigen binding fragment thereof, comprises:
a heavy chain comprising SEQ ID NO:25; and
a light chain comprising SEQ ID NO:31.

24. A composition comprising the antibody, or antigen binding fragment thereof, of claim 19 and a pharmaceutically acceptable carrier.

25. A composition comprising the antibody, or antigen binding fragment thereof, of claim 19 and further comprising a label conjugated directly or indirectly to the antibody.

* * * * *